United States Patent
Ichijo et al.

(10) Patent No.: US 10,689,394 B2
(45) Date of Patent: Jun. 23, 2020

(54) THIENO[2,3-B]PYRIDINE DERIVATIVE, QUINOLINE DERIVATIVE, AND USE THEREOF

(71) Applicant: The University of Tokyo, Tokyo (JP)

(72) Inventors: Hidenori Ichijo, Tokyo (JP); Kengo Homma, Tokyo (JP); Naomi Tsuburaya, Tokyo (JP); Tetsuo Nagano, Tokyo (JP); Takayoshi Okabe, Tokyo (JP); Hirotatsu Kojima, Tokyo (JP); Manabu Shimonishi, Tokyo (JP); Takao Fujisawa, Tokyo (JP); Norio Shiibata, Nagoya (JP); Tsunehiko Higuchi, Nagoya (JP); Seiichi Nakamura, Nagoya (JP); Hidehiko Nakagawa, Nagoya (JP); Shin-Ichi Ikeda, Nagoya (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 16/306,696

(22) PCT Filed: Jun. 14, 2017

(86) PCT No.: PCT/JP2017/021895
§ 371 (c)(1),
(2) Date: Jan. 25, 2019

(87) PCT Pub. No.: WO2017/217439
PCT Pub. Date: Dec. 21, 2017

(65) Prior Publication Data
US 2019/0177336 A1 Jun. 13, 2019

(30) Foreign Application Priority Data
Jun. 14, 2016 (JP) ................. 2016-117807

(51) Int. Cl.
*C07D 495/04* (2006.01)
*C07D 401/04* (2006.01)
(Continued)

(52) U.S. Cl.
CPC ........ *C07D 495/04* (2013.01); *A61K 31/4365* (2013.01); *A61P 21/00* (2018.01); *A61P 21/02* (2018.01); *C07D 401/04* (2013.01)

(58) Field of Classification Search
None
See application file for complete search history.

(56) References Cited

U.S. PATENT DOCUMENTS

2013/0129677 A1* 5/2013 Dai ...................... C07D 495/04
424/85.4

FOREIGN PATENT DOCUMENTS

| JP | 2007-151478 A | 6/2007 |
|---|---|---|
| WO | 2008/011560 A2 | 1/2008 |

(Continued)

OTHER PUBLICATIONS

Silber, B. M. et al., "Antiprion compounds that reduce PrPSc levels in dividing and stationary-phase cells", Bioorg Med Chem., Dec. 15, 2013, pp. 7999-8012; cited in ISR.

(Continued)

*Primary Examiner* — Zinna Northington Davis
(74) *Attorney, Agent, or Firm* — Westerman, Hattori, Daniels & Adrian, LLP

(57) ABSTRACT

A compound represented by the following formula (1) is provided:

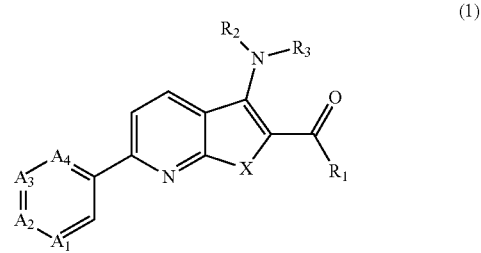

(1)

wherein X represents a sulfur atom or —CH═CH—; $A_1$ to $A_4$ each independently represent a carbon atom or a nitrogen atom, and at least one of $A_1$ to $A_4$ is a nitrogen atom; $R_1$ represents any one of a 1,2,3,4-tetrahydroquinolyl group (or a 3,4-dihydro-1(2H)-quinolyl group), a 3,4-dihydro-4,4-dimethyl-1(2H)-quinolyl group, a 2,3,4,5-tetrahydro-1H-1-benzazepinyl group, or a substituent represented by the following formula (2):

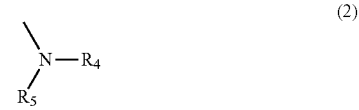

(2)

wherein $R_4$ represents a 2,3,4-trifluorophenyl group, a 4-iodophenyl group, a 2,3-difluorophenyl group, a 3,5-difluorophenyl group, a 5-fluoro-2-methylphenyl group, a 3-pentafluorosulfanylphenyl group, a 2,6-dimethylphenyl group, a 4-benzyloxyphenyl group, a 3,5-bis(trifluoromethyl)biphenyl group, a 4-tert-butylphenyl group, a 3-methoxyphenyl group, an unsubstituted or substituted pyridyl group, or an unsubstituted or substituted naphthyl group; $R_5$ represents a hydrogen atom, a lower alkyl group, a lower alkenyl group, a lower alkynyl group optionally containing an oxygen atom and/or a double bond, or an unsubstituted or substituted aromatic lower alkyl group; $R_2$ represents a hydrogen atom, a lower alkyl group, a lower acyl group, or an unsubstituted (Continued)

or substituted aromatic lower alkyl group; and R₃ represents a hydrogen atom, or R₂ and R₃ may bind to each other to form a ring.

18 Claims, 8 Drawing Sheets

(51) Int. Cl.
  *A61P 21/02* (2006.01)
  *A61K 31/4365* (2006.01)
  *A61P 21/00* (2006.01)

(56) References Cited

FOREIGN PATENT DOCUMENTS

| WO | 2010/099166 A1 | 9/2010 |
| WO | 2010/151799 A2 | 12/2010 |
| WO | 2011/006158 A2 | 1/2011 |
| WO | 2011/142461 A1 | 11/2011 |
| WO | 2013/033037 A2 | 3/2013 |
| WO | 2014/089378 A1 | 6/2014 |
| WO | 2014/207213 A1 | 12/2014 |

OTHER PUBLICATIONS

Sorci, L. et al., "Targeting NAD biosynthesis in bacterial pathogens. Structure-based development of inhibitors of nicotinate mononucleotide adenylyltransferase NadD", Chem Biol., Aug. 18, 2008, pp. 849-861; cited in ISR.
Reynisson, J. et al., "The identification of novel PLC-gamma inhibitors using virtual high throughput screening", Bioorganic & Medicinal Chemistry, 2009, pp. 3169-3176; cited in ISR.
PubChem SID 22402554, "3-Amino-6-pyridin-3-yl-thieno[2,3-b]pyridine-2-carboxylic acid (2,3-dichloro-phenyl)-amide", U.S. National Library of Medicine National Center for Biotechnology Information; cited in ISR. (7 pages). Mar. 5, 2007.
PubChem SID 24791524, "3-Amino-6-pyridin-3-yl-thieno[2,3-b]pyridine-2-carboxylic acid phenylamide", U.S. National Libray of Medicine National Center for Biotechnology Information; cited in ISR. (7 pages). Jul. 5, 2007.
Bensimon, G. et al., "A Controlled Trial of Riluzole in Amyotrophic Lateral Sclerosis", The New England Journal of Medicine, Mar. 3, 1994, vol. 330, No. 9, pp. 585-591; cited in the Specification.
Miller, R. G. et al. "Clinical trials of riluzole in patients with ALS", Neurology, 1996, pp. S86-S92; cited in the Specification.
Yoshino, H. et al., "Investigation of the therapeutic effects of edaravone, a free radical scavenger, on amyotrophic lateral sclerosis (Phase II study)", Amyotrophic Lateral Sclerosis, 2006, pp. 247-251; cited in the Specification.
Rosen, D. R. et al., "Mutations in Cu/Zn superoxide dismutase gene are associated with familial amyotrophic lateral sclerosis", Nature, Mar. 4, 1993, vol. 362, pp. 59-62; cited in the Specification.
Cleveland, D. W. et al., "Toxic mutants in Charcot's sclerosis", Nature, 1995; pp. 342-343; cited in the Specification.
Boillee, S. et al., "ALS: A Disease of Motor Neurons and Their Nonneuronal Neighbors", Neuron, Oct. 5, 2006, pp. 39-59; cited in the Specification.
Ilieva, H. et al., "Non-cell autonomous toxicity in neurodegenerative disorders: ALS and beyond", J Cell Biol, 2009, vol. 187, No. 6, pp. 761-772; cited in the Specification.
Mori, K., "Tripartite Management of Unfolded Proteins in the Endoplasmic Reticulum" Cell, May 26, 2000, vol. 101, pp. 451-454; cited in the Specification.
Homma, K. et al., "Targeting ASK1 in ER stress-related neurodegenerative diseases", Expert Opinion on Therapeutic Targets, 2009, pp. 653-664; cited in the Specification.
Nishitoh, H. et al., "ALS-linked mutant SOD1 induces ER stress- and ASK1-dependent motor neuron death by targeting Derlin-1", Genes and Development, Apr. 11, 2008, pp. 1451-1464; cited in the Specification and ISR.
Meusser, B. et al., "ERAD: the long road to destruction", Nature Cell Biology, Aug. 2005, vol. 7, No. 8, pp. 166-772; cited in the Specification.
Tsai, B. et al., "Retro-Translocation of Proteins from the Endoplasmic Reticulum into the Cytosol", Nature Reviews Molecular Cell Biology, Apr. 2002, vol. 3, pp. 246-255; cited in the Specification.
Ye Y. et al., "A membrane protein complex mediates retro-translocation from the ER lumen into the cytosol", Nature, Jun. 24, 2004, vol. 429, pp. 841-847; cited in the Specification.
Lilley, B. N. et al., "A membrane protein required for dislocation of misfolded proteins from the ER", Nature, Jun. 24, 2004, vol. 429, pp. 834-840; cited in the Specification.
Oda, Y. et al., "Derlin-2 and Derlin-3 are regulated by the mammalian unfolded protein response and are required for ER-associated degradation", The Journal of Cell Biology, Jan. 30, 2006, vol. 172, No. 3, pp. 383-393; cited in the Specification.
Lilley, B. et al., "Multiprotein complexes that link dislocation, ubiquitination, and extraction of misfolded proteins from the endoplasmic reticulum membrane", PNAS, Oct. 4, 2005, vol. 102, No. 40, pp. 14296-14301; cited in the Specification.
Ye, Y. et al., "Recruitment of the p97 ATPase and ubiquitin ligases to the site of retrotranslocation at the endoplasmic reticulum membrane", PNAS, Oct. 4, 2005, vol. 102, No. 40, pp. 14132-14138; cited in the Specification.
Fujisawa, T. et al., "A Novel Monoclonal Antibody Reveals a Conformational Alteration Shared by Amyotrophic Lateral Sclerosis-Linked SOD1 Mutants", Ann Neurol, 2012, pp. 739-749; cited in the Specification and ISR.

\* cited by examiner

[Figure 1]
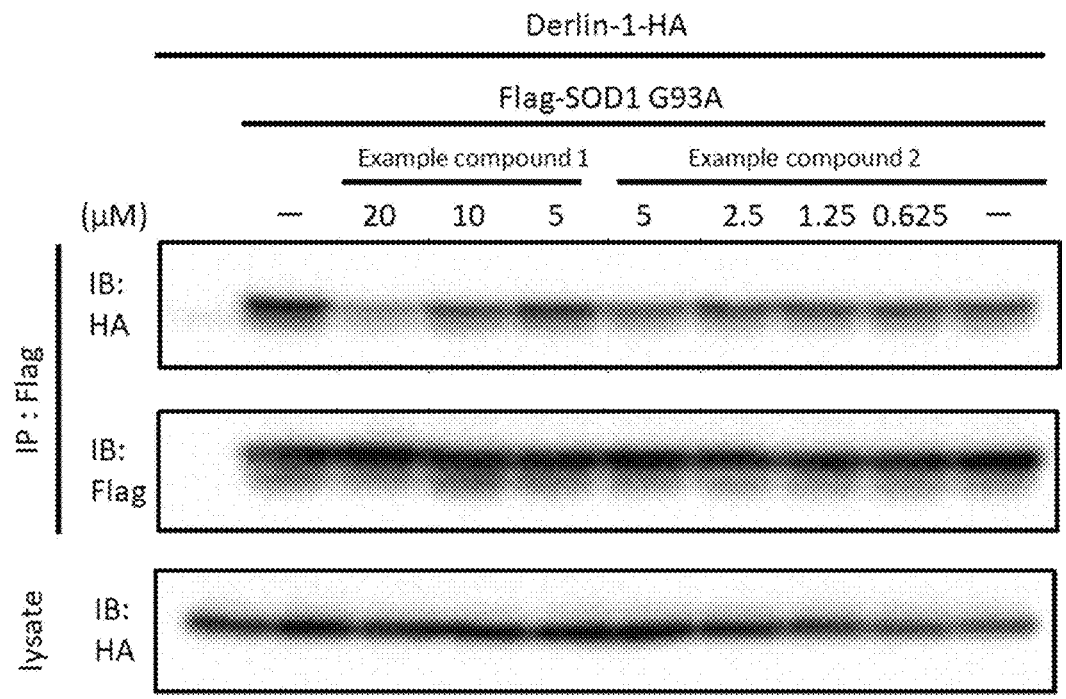
[Figure 2]
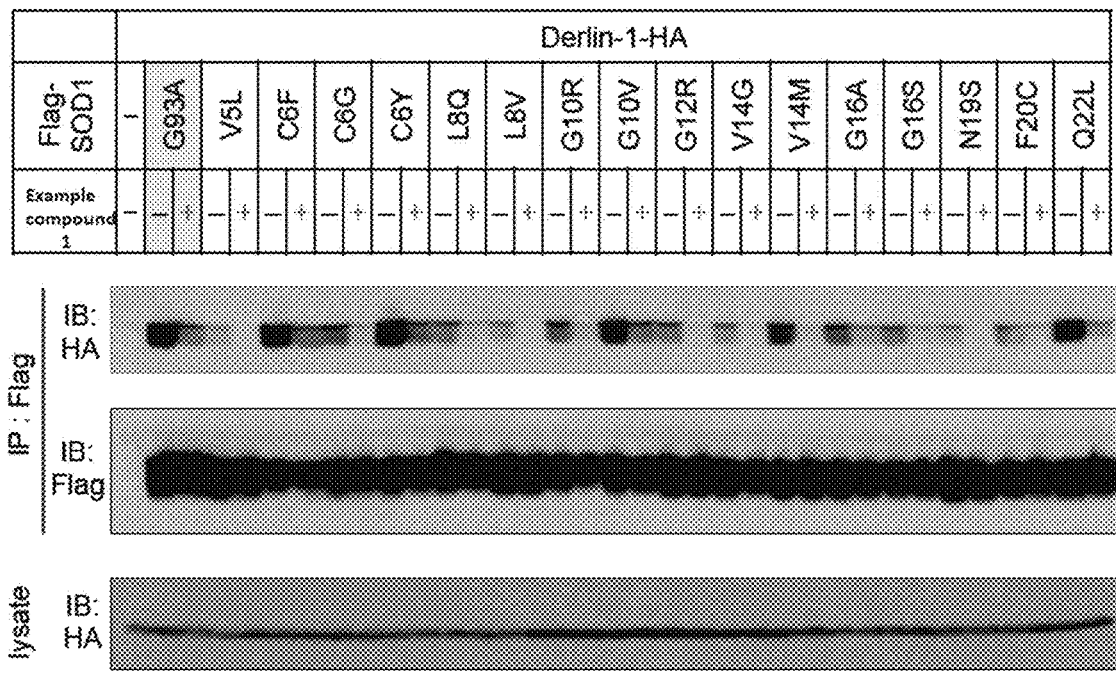

[Figure 3]
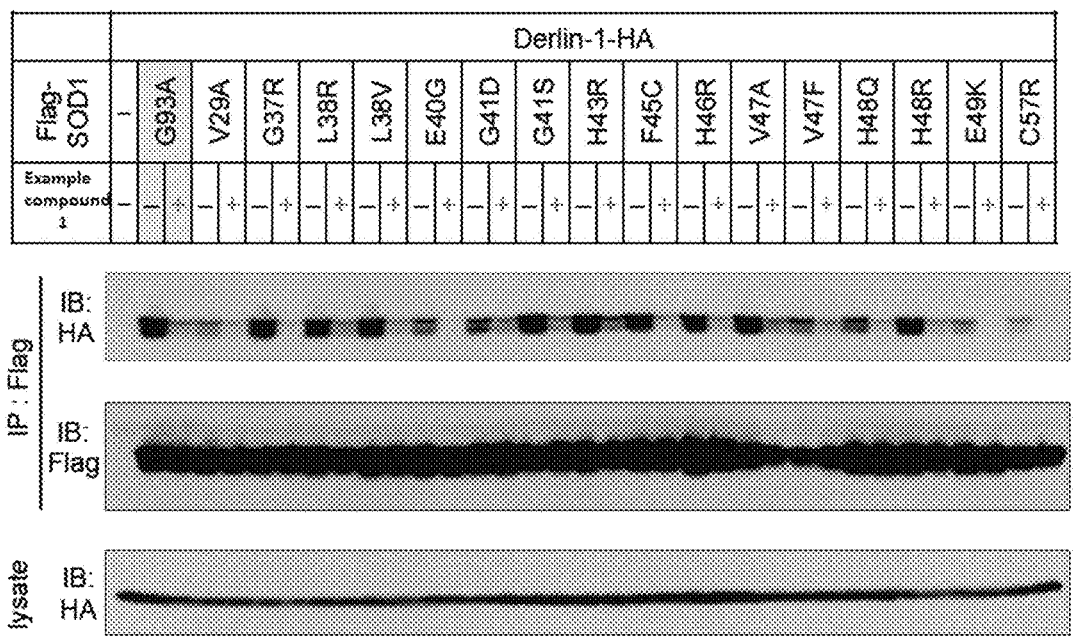
[Figure 4]
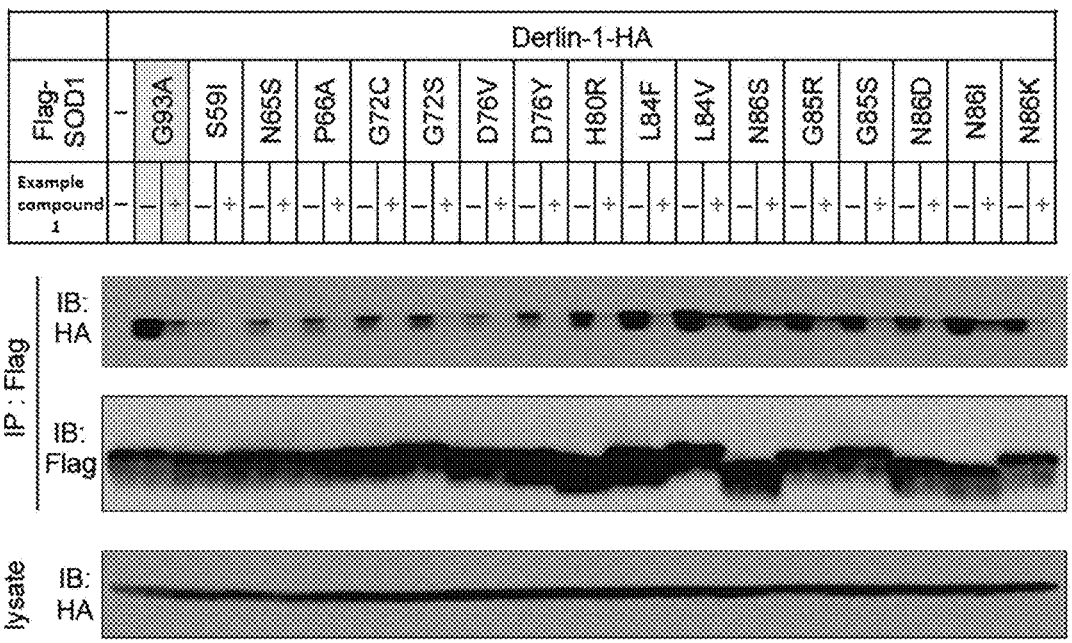

[Figure 5]
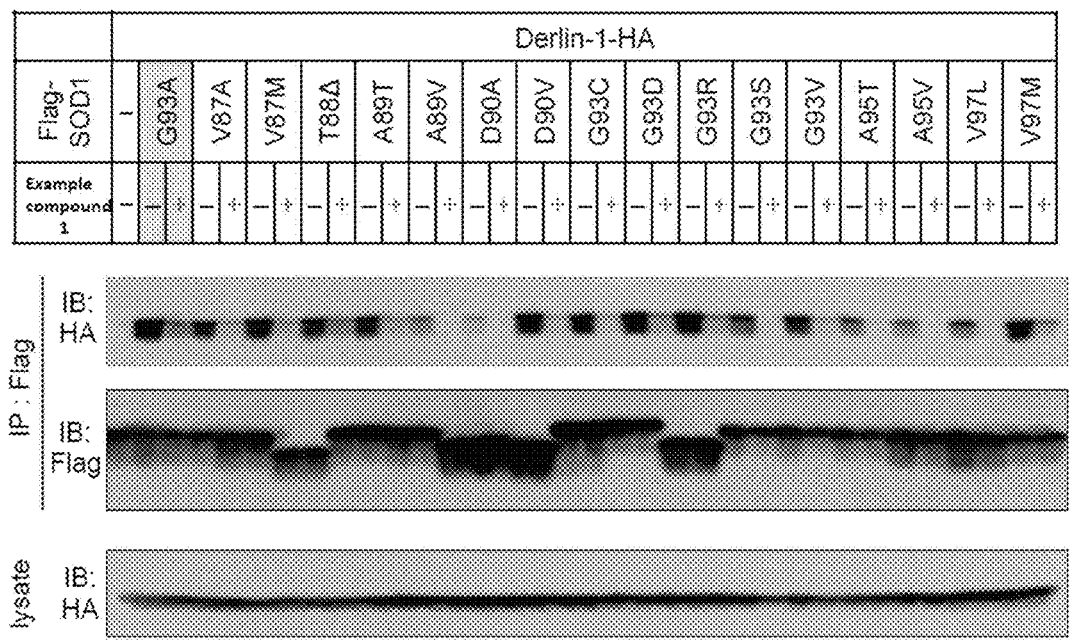
[Figure 6]
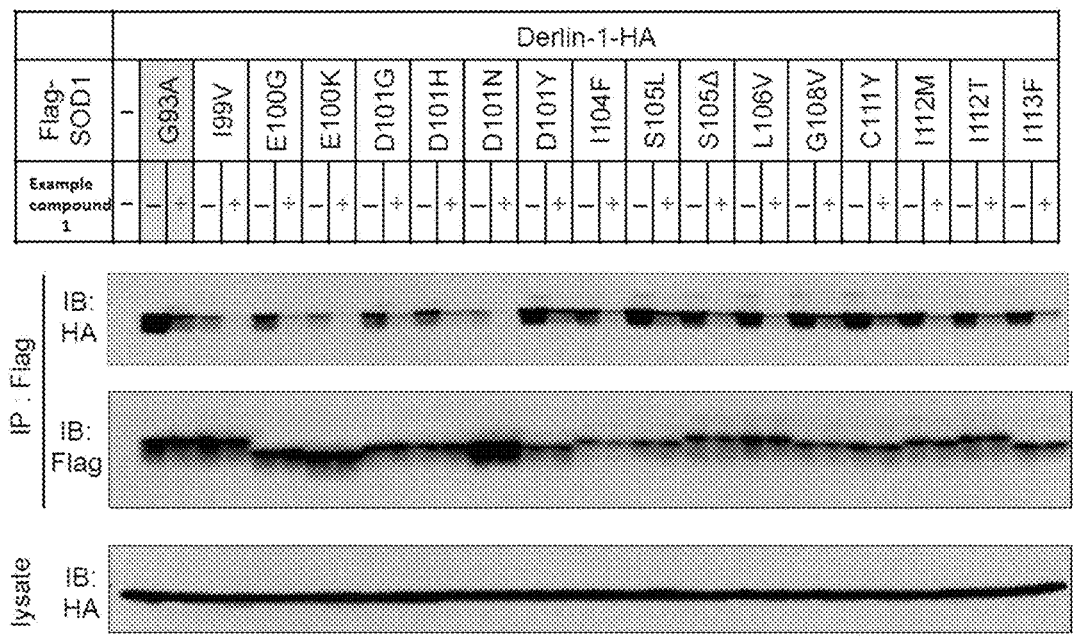

[Figure 7]
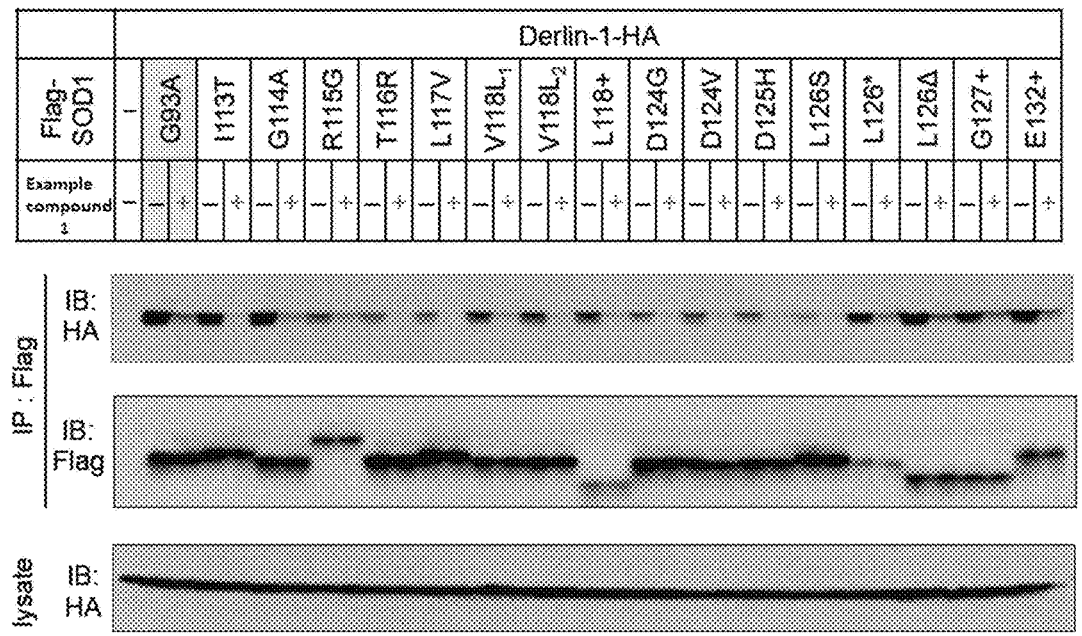
[Figure 8]
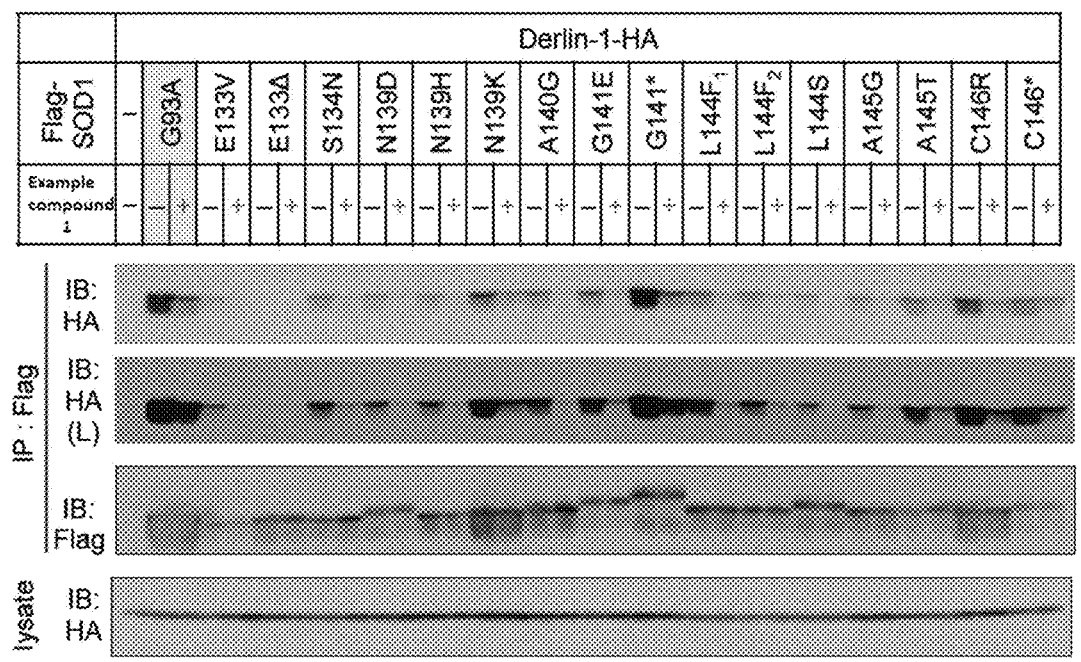

[Figure 9]
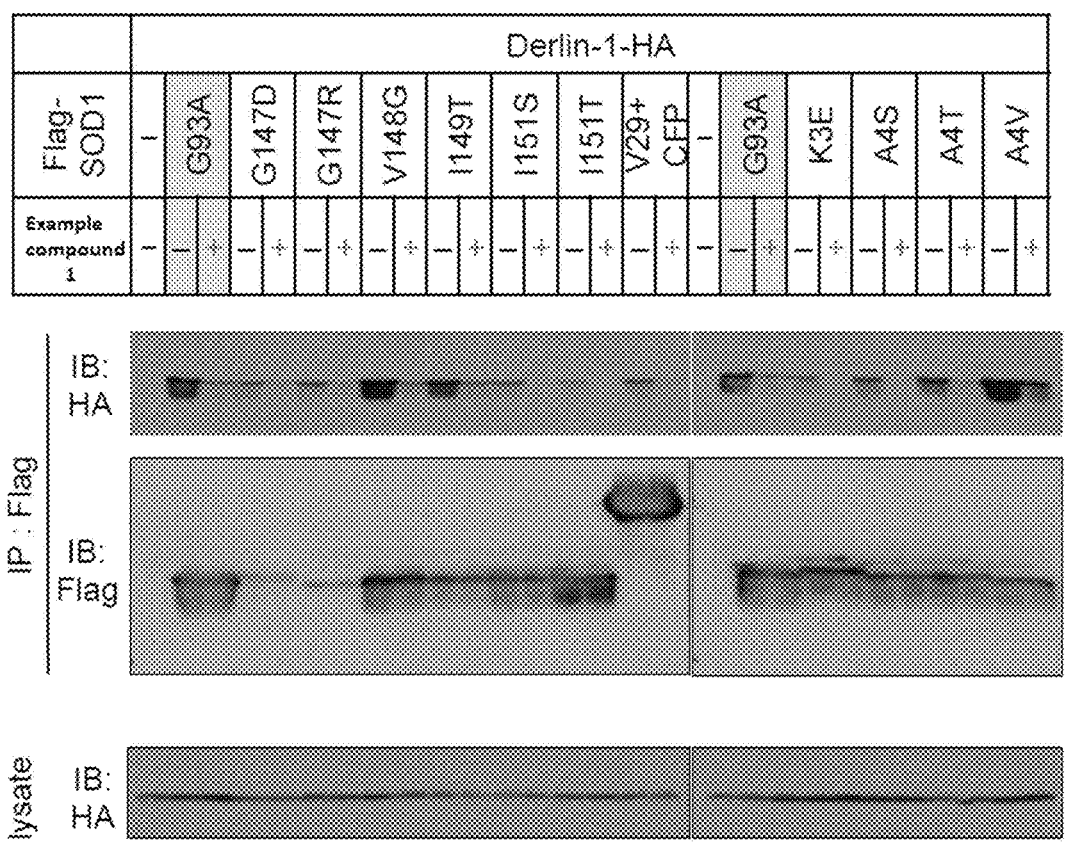

[Figure 11]
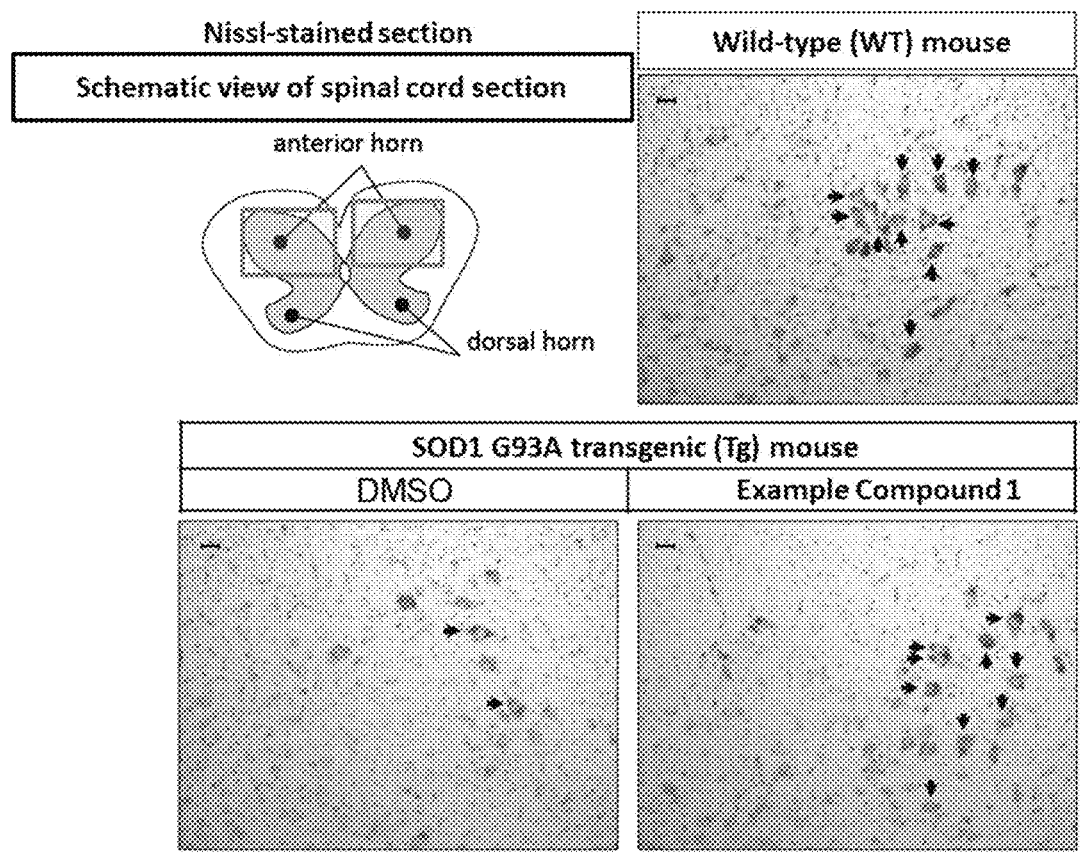

[Figure 12]
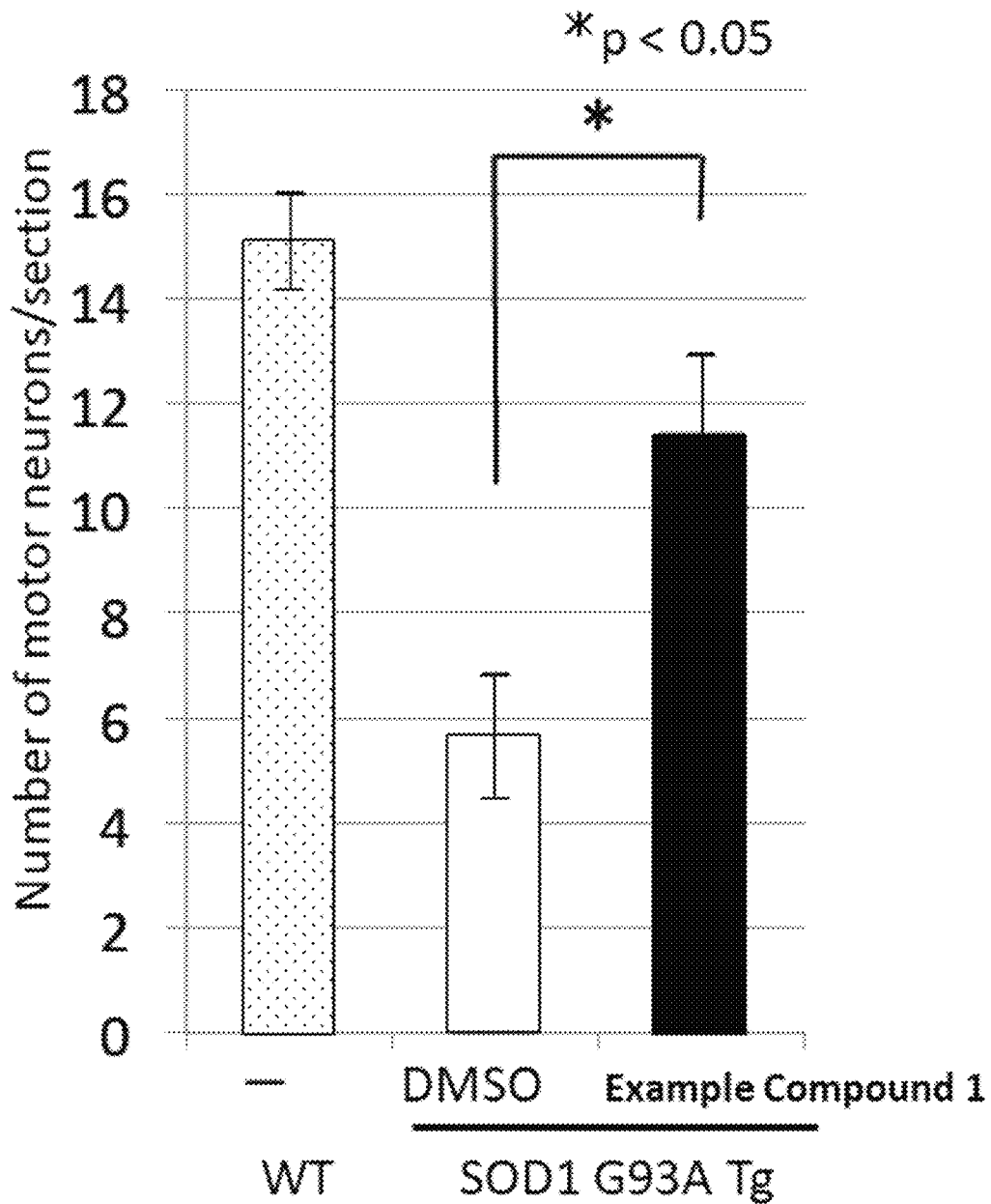

THIENO[2,3-B]PYRIDINE DERIVATIVE, QUINOLINE DERIVATIVE, AND USE THEREOF

TECHNICAL FIELD

The present invention relates to a compound that inhibits the binding between ALS-related mutant SOD1 and Derlin-1, a medicament comprising the compound, and a method for treating ALS by administering the medicament to a patient.

BACKGROUND ART

Amyotrophic lateral sclerosis (ALS) is a progressive and/or tardive neurodegenerative disease, by which upper and lower motor neurons are selectively damaged. Amyotrophic lateral sclerosis is an extremely serious disease, which has symptoms such as convulsion, muscle paralysis or muscle atrophy, brings on respiratory failure mainly caused by respiratory muscle paralysis, and results in death in a few years after the onset thereof. The number of patients suffering from amyotrophic lateral sclerosis in Japan is approximately 9000, and there are only several hundreds of thousands of ALS patients over the world. Since the number of ALS patients is fewer than those of patients with other neurodegenerative diseases such as Alzheimer's disease or Parkinson's disease, the development of therapeutic agents for ALS is behind. The currently approved therapeutic agents are only a glutamate nerve ending release inhibitor (Riluzole) and an active oxygen scavenger (Edaravone), which have the effect of temporally delaying progression (Non Patent Literatures 1, 2 and 3). However, the action mechanism of such neuron-protecting effect on ALS has not been elucidated. In addition, since the pathological molecular mechanism of developing ALS has not yet been known, a fundamental treatment method, which is based on a clear molecular basis, has not existed.

A majority of ALS diseases are sporadic ALS (SALS), and familial ALS (FALS) accounts for 10% of the whole ALS diseases. In 1993, Cu, Zn Superoxide dismutase (SOD1) has been identified for the first time as a causative gene of FALS (Non Patent Literature 4). More than 100 types of ALS-related SOD1 mutations have been reported so far (ALS Online Database: ALSoD). SOD1 is a metalloprotein having a disulfide bond in a molecule thereof, in which one Zn ion and one Cu ion are coordinated. It has been known that SOD1 generally forms a homodimer and acts as an antioxidant enzyme disproportionating active oxygen ($O_2$) to hydrogen peroxide ($H_2O_2$) via the oxidation-reduction of Cu ions in an active center. On the other hand, a large number of studies have been conducted so far, regarding the correlation of SOD1 with the onset of ALS, and as a result, it has been revealed that there is no correlation between the antioxidative activity of SOD1 and the seriousness of the pathological condition of ALS (Non Patent Literature 5). At present, it is considered that not only the loss or acceleration of SOD activity, but also newly acquired cytotoxicity that is exhibited by SOD1 as a result of mutation has a certain importance on motor neuron death and the subsequent onset of ALS (Non Patent Literature 6). It has been suggested that the acquired cytotoxicity, such as neural excitotoxicity, endoplasmic reticulum stress, proteasome inhibition, oxidative stress, mitochondrial dysfunction or axonal transport abnormality, is associated with motor neuron death, but the detailed mechanism of the onset of ALS still remains unknown (Non Patent Literature 7).

Endoplasmic reticulum is an organelle that plays roles, such as formation of the conformation of a newly synthesized secretory protein or membrane protein, and the quality control of these proteins. Among the proteins existing in the endoplasmic reticulum lumen, proteins that do not have a correct conformation, namely, unfolded proteins are present at a certain ratio. In addition, such unfolded proteins are formed even by various physiological and/or pathological stresses, such as nutrient starvation, hypoxia or gene mutation, and the thus formed unfolded proteins are accumulated in the endoplasmic reticulum lumen, so that they cause endoplasmic reticulum stress.

It has been known that, at this time, the mechanism of controlling endoplasmic reticulum quality is functioned in a cell by endoplasmic reticulum stress response (unfold protein response: UPR), in order to maintain normal function in the cell (Non Patent Literature 8). According to the UPR, signals are transmitted via activation of three types of endoplasmic reticulum transmembrane receptors, namely, Pancreatic ER kinase (PKR)-like ER kinase (PERK), activating transcription factor 6 (ATF6), and inositol-requiring enzyme 1 (IRE1), so that (i) suppression of protein synthesis, (ii) induction of the expression of endoplasmic reticulum chaperones and molecules involved in endoplasmic reticulum-associated degradation (ER-associated degradation: ERAD), (iii) degradation of unfolded proteins by ERAD, etc. are carried out, and thereby, the recovery of the functions of the endoplasmic reticulum is achieved. On the other hand, when unfolded proteins are excessively accumulated in the endoplasmic reticulum lumen and the homeostasis of the endoplasmic reticulum cannot be maintained by continuous or excessive stress or the dysfunction of UPR, apoptosis is induced. It has been suggested that this endoplasmic reticulum stress-induced cell death should be involved, as a molecular mechanism of disease caused by accumulation of structurally abnormal proteins, in various pathologic conditions including diabetes or neurodegenerative disease (Non Patent Literature 9). However, the molecular mechanism of inducing endoplasmic reticulum stress in ALS has not yet been elucidated.

The present inventors had reported that, as a mechanism of the onset of FALS, the function of ERAD is inhibited by mutant SOD1 and thereby, motor neuron death caused by endoplasmic reticulum stress is induced (Non Patent Literature 10). In general, unfolded proteins existing in the endoplasmic reticulum lumen, which could not have a correct conformation even by the function of endoplasmic reticulum chaperones, are decomposed by ERAD. Specifically, such unfolded proteins are recognized by endoplasmic reticulum chaperones including BiP as a typical example, and are then reversely transferred from the endoplasmic reticulum lumen to the cytoplasmic side via an ERAD complex. Thereafter, the unfolded proteins are decomposed by an ubiquitin-proteasome system existing on the cytoplasmic side, so that the accumulation of the unfolded proteins in the endoplasmic reticulum lumen is reduced, and the homeostasis of the endoplasmic reticulum is maintained (Non Patent Literatures 11 and 12). On the other hand, in cells in which mutant SOD1 is expressed, it has been found that such mutant SOD1 specifically binds to the C-terminal 12 amino acids (hereinafter abbreviated as "CT4") of Derlin-1 that is an important configuration factor of the ERAD complex, and it inhibits the flow of ERAD, so as to suppress decomposition of the ERAD substrate. Due to such inhibition of the function of ERAD, unfolded proteins are accumulated in the endoplasmic reticulum lumen, and the thus induced endoplasmic reticulum stress causes the death of motor neurons via apoptosis (Non Patent Literature 10).

Derlin-1 is an endoplasmic reticulum transmembrane protein that has been identified as a molecule playing an important role in the retrotransloction of the ERAD substrate (Non Patent Literatures 13 and 14). It has been demonstrated that Derlin-1 homologs in mammals include Derlin-2 and Derlin-3, and that these Derlin family molecules form a homo or hetero complex, and interact with ERAD-related molecules such as HRD1, SEL1L, Herp, VIMP, or p97 (Non Patent Literatures 15, 16 and 17). Details of the function of Derlin-1 in ERAD have not yet been revealed, but it has been found that ALS-related mutant SOD1 does not bind to Derlin-2 or Derlin-3, or ERAD-related molecules such as VIMP or p97, but that ALS-related mutant SOD1 specifically binds to only the C-terminus of Derlin-1. Moreover, suppression of the expression of Derlin-1 by knocking down did not provoke endoplasmic reticulum stress, but such suppression of Derlin-1 expression inhibited induction of endoplasmic reticulum stress by mutant SOD1 (Non Patent Literature 10). From these results, it is considered that endoplasmic reticulum stress caused by mutant SOD1 is not induced via the loss of the function of Derlin-1, but the endoplasmic reticulum stress is induced, when Derlin-1 binds to mutant SOD1 so that the Derlin-1 exhibits acquired dysfunction and normal ERAD is thereby inhibited.

The present inventors have produced expression vectors for 130 types of known ALS-related mutant SOD1s, and have examined the binding between all of the mutant SOD1s and Derlin-1. As a result, it has been revealed that all of the mutant SOD1s except for mutants having very low correlation with the pathologic conditions (i.e., 122 types of mutant SOD1s) bind to Derlin-1 CT4 (Non Patent Literature 18). Since mutation covers a broad range on the primary sequence of SOD1, it has been considered that each mutant SOD1 does not individually acquire a surface binding to Derlin-1 as a result of the mutation, but that a region binding to Derlin-1 is present in the sequence of wild-type SOD1. As such, the region of SOD1 that interacts with Derlin-1 has been examined. As a result, it has been revealed that a region binding to Derlin-1 (Derlin-1 binding region: DBR) consisting of 14 amino acids is present in wild-type SOD1, as expected (Non Patent Literature 18). Moreover, a monoclonal antibody produced against this DBR region did not recognize wild-type SOD1, but specifically recognized all mutant SOD is that bind to Derlin-1 (except for mutations of antibody epitope portions) in an immunoprecipitation experiment (Non Patent Literature 18 and Patent Literature 1). From these results, it has been suggested that ALS-related mutant SOD1s should be likely to have a common feature that DBR, which is hiding inside for the conformational reason in the case of wild-type SOD1, is exposed outside due to a structural change caused by mutation. Furthermore, SOD1 in a B cell derived from a human ALS patient having an SOD1 gene mutation has also been recognized by a mutant SOD1-specific antibody (Non Patent Literature 18 and Patent Literature 1), and it has also been confirmed that endogenous SOD1 and Derlin-1 actually bind to each other. Accordingly, it has been considered that the binding of SOD1 to Derlin-1 via DBR exposure is also associated with the pathologic conditions of human ALS. In addition, it has been revealed that, in a mouse spinal cord-derived primary motor neuron culture system, mutant SOD1-induced motor neuron death is suppressed by allowing a peptide that inhibits the binding between SOD1 and Derlin-1 (Derlin-1 (CT4) peptide: Derlin-1 CT4 region-derived peptide) to express in the cells (Non Patent Literature 10).

As mentioned above, it has been suggested that inhibition of the binding between ALS-related mutant SOD1 and Derlin-1 should lead to the treatment of ALS caused by SOD1 mutation. However, a therapeutic agent and a treatment method, which are effective for ALS, have not yet been discovered so far.

CITATION LIST

Patent Literature

Patent Literature 1: WO2011/142641

Non Patent Literature

Non Patent Literature 1: Bensimon et al., Engl J Med 330, 585-591, (1994).
Non Patent Literature 2: Miller et al., Neurology 47, S86-90; discussion S90-82, (1996).
Non Patent Literature 3: Yoshino et al., Amyotroph Lateral Scler 7, 241-245, (2006).
Non Patent Literature 4: Rosen et al., Nature 362, 59-62, (1993).
Non Patent Literature 5: Cleveland et al., Nature 378, 342-343, (1995).
Non Patent Literature 6: Boillee et al., Neuron 52, 39-59, (2006).
Non Patent Literature 7: Ilieva et al., J Cell Biol 187, 761-772, (2009).
Non Patent Literature 8: Mori et al., Cell 101, 451-454, (2000).
Non Patent Literature 9: Homma et al., Expert Opin Ther Targets 13, 653-664, (2009).
Non Patent Literature 10: Nishitoh et al., Genes Dev 22, 1451-1464, (2008).
Non Patent Literature 11: Meusser et al., Nat Cell Biol 7, 766-772, (2005).
Non Patent Literature 12: Tsai et al., Nat Rev Mol Cell Biol 3, 246-255, (2002).
Non Patent Literature 13: Ye et al., Nature 429, 841-847, (2004).
Non Patent Literature 14: Lilley et al., Nature 429, 834-840, (2004).
Non Patent Literature 15: Oda et al., J Cell Biol 172, 383-393, (2006).
Non Patent Literature 16: Lilley et al., Proc Natl Acad Sci U.S.A., 102, 14296-14301, (2005).
Non Patent Literature 17: Ye et al., Proc Natl Acad Sci U.S.A., 102, 14132-14138, (2005).
Non Patent Literature 18: Fujisawa et al., Ann Neurol 72, 739-749, (2012).

SUMMARY OF INVENTION

Technical Problem

Under the aforementioned circumstances, for the purpose of developing a therapeutic agent for ALS, the present inventors have determined the development of a substance that inhibits or suppresses the binding between ALS-related mutant SOD1 and Derlin-1 to be an object of the present invention.

That is to say, it is an object of the present invention to provide a compound that inhibits the binding between ALS-related mutant SOD1 and Derlin-1, a medicament comprising the compound, and a method for treating ALS by administering the medicament to a patient.

Solution to Problem

The present inventors have conducted intensive studies directed towards achieving the aforementioned object. As a result, the inventors have found a thieno[2,3-b]pyridine derivative and a quinoline derivative, which inhibit the binding between ALS-related mutant SOD1 and Derlin-1, thereby completing the present invention.

Specifically, the present invention relates to a compound represented by the following formula (1) or a salt thereof, or a solvate or hydrate thereof:

[Formula 1]

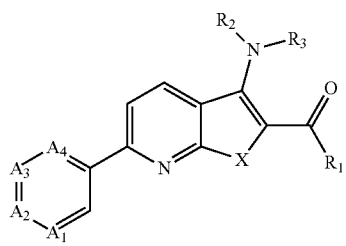

(1)

wherein X represents a sulfur atom or —CH=CH—; $A_1$ to $A_4$ each independently represent a carbon atom or a nitrogen atom, and at least one of $A_1$ to $A_4$ is a nitrogen atom; $R_1$ represents any one of a 1,2,3,4-tetrahydroquinolyl group (or a 3,4-dihydro-1(2H)-quinolyl group), a 3,4-dihydro-4,4-dimethyl-1(2H)-quinolyl group, a 2,3,4,5-tetrahydro-1H-1-benzazepinyl group, or a substituent represented by the following formula (2):

[Formula 2]

(2)

wherein $R_4$ represents an unsubstituted or optionally substituted phenyl group, an unsubstituted or optionally substituted pyridyl group, or an unsubstituted or optionally substituted naphthyl group, and $R_5$ represents a hydrogen atom, a lower alkyl group, a lower alkenyl group, a lower alkynyl group (optionally containing an oxygen atom and/or a double bond), or an unsubstituted or optionally substituted aromatic lower alkyl group; $R_2$ represents a hydrogen atom, a lower alkyl group, a lower acyl group, or an unsubstituted or optionally substituted aromatic lower alkyl group; and $R_3$ represents a hydrogen atom, or $R_2$ and $R_3$ may bind to each other to form a ring.

The present invention particularly relates to a thieno[2,3-b]pyridine derivative represented by the following formula (1a), a quinoline derivative represented by the following formula (1b), a salt of the thieno[2,3-b]pyridine derivative represented by the following formula (1a), a salt of the quinoline derivative represented by the following formula (1b), or a solvate or hydrate thereof:

[Formula 3]

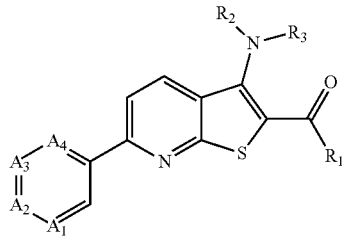

(1a)

wherein $A_1$ to $A_4$ each independently represent a carbon atom or a nitrogen atom, and at least one of $A_1$ to $A_4$ is a nitrogen atom; $R_1$ represents any one of a 1,2,3,4-tetrahydroquinolyl group (or a 3,4-dihydro-1(2H)-quinolyl group), a 3,4-dihydro-4,4-dimethyl-1(2H)-quinolyl group, a 2,3,4,5-tetrahydro-1H-1-benzazepinyl group, or a substituent represented by the following formula (2):

[Formula 4]

(2)

wherein $R_4$ represents an unsubstituted or optionally substituted phenyl group, an unsubstituted or optionally substituted pyridyl group, or an unsubstituted or optionally substituted naphthyl group, and $R_5$ represents a hydrogen atom, a lower alkyl group, a lower alkenyl group, a lower alkynyl group (optionally containing an oxygen atom and/or a double bond), or an unsubstituted or optionally substituted aromatic lower alkyl group; $R_2$ represents a hydrogen atom, a lower alkyl group, a lower acyl group, or an unsubstituted or optionally substituted aromatic lower alkyl group; and $R_3$ a hydrogen atom, or $R_2$ and $R_3$ may bind to each other to form a ring, or

[Formula 5]

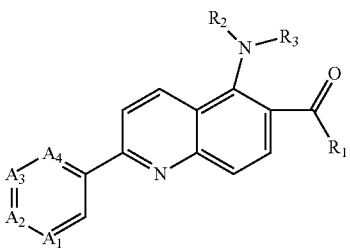

(1b)

wherein $A_1$ to $A_4$ each independently represent a carbon atom or a nitrogen atom, and at least one of $A_1$ to $A_4$ is a nitrogen atom; $R_1$ represents a substituent represented by the following formula (2):

[Formula 6]

(2)

wherein R$_4$ represents an unsubstituted or optionally substituted phenyl group, and R$_5$ represents a hydrogen atom, a lower alkyl group, a lower alkenyl group, or a lower alkynyl group; R$_2$ represents a hydrogen atom, a lower alkyl group, a lower acyl group, or an unsubstituted or optionally substituted aromatic lower alkyl group; and R$_3$ represents a hydrogen atom, or R$_2$ and R$_3$ may bind to each other to form a ring.

The present invention further relates to an ALS-related mutant SOD1-Derlin-1 binding inhibitor for inhibiting the binding between ALS-related mutant SOD1 and Derlin-1, wherein the inhibitor comprises, as an active ingredient, at least one of the compound represented by the above formula (1) (the above formulae (1a) and (1b)), a salt thereof, or a solvate or hydrate thereof.

The present invention still further relates to a medicament or a pharmaceutical composition, which comprises, as an active ingredient, at least one of the compound represented by the above formula (1) (the above formulae (1a) and (1b)), a salt thereof, or a solvate or hydrate thereof, or a medicament or a pharmaceutical composition, which comprises the above-described ALS-related mutant SOD1-Derlin-1 binding inhibitor.

Advantageous Effects of Invention

The compound represented by the above formula (1) (the above formulae (1a) and (1b)) according to the present invention has the function of inhibiting the binding between ALS-related mutant SOD1 and Derlin-1. Accordingly, an ALS-related mutant SOD1-Derlin-1 binding inhibitor or a medicament, which comprises the compound represented by the above formula (1) (the above formulae (1a) and (1b)) according to the present invention, can be used in the treatment of ALS.

Moreover, the compound represented by the above formula (1) (the above formulae (1a) and (1b)) according to the present invention can also be used as a lead compound of therapeutic agents for ALS.

BRIEF DESCRIPTION OF DRAWINGS

FIG. 1 shows evaluation of the binding inhibitory activity of Example Compound 1 and Example Compound 4 on intracellular AT S-related mutant SOD1-Derlin-1 binding. FIG. 1 shows the results obtained by allowing HEK293A cells to overexpress each protein, then adding Example Compound 1 or Example Compound 4 in each concentration to the cell culture, and then performing co-immunoprecipitation. IP: Flag indicates immunoprecipitation performed with an anti-Flag antibody. In addition, IB: HA and IB: Flag indicate blotting performed with an anti-HA antibody and an anti-Flag antibody, respectively. The term "lysate" indicates a cell lysate.

FIG. 2 shows evaluation of the binding inhibitory activity of Example Compound 1 on intracellular SOD1-Derlin-1 binding according to a co-immunoprecipitation experiment. FIG. 2 shows the results obtained in the case of using mutant SOD1 s until the 17th mutant SOD1 in 122 types of mutant SOD1s.

FIG. 3 shows evaluation of the binding inhibitory activity of Example Compound 1 on intracellular SOD1-Derlin-1 binding according to a co-immunoprecipitation experiment. FIG. 3 shows the results obtained in the case of using mutant SOD1s until the 33rd mutant SOD1 in 122 types of mutant SOD1s.

FIG. 4 shows evaluation of the binding inhibitory activity of Example Compound 1 on intracellular SOD1-Derlin-1 binding according to a co-immunoprecipitation experiment. FIG. 4 shows the results obtained in the case of using mutant SOD1s until the 49th mutant SOD1 in 122 types of mutant SOD1s.

FIG. 5 shows evaluation of the binding inhibitory activity of Example Compound 1 on intracellular SOD1-Derlin-1 binding according to a co-immunoprecipitation experiment. FIG. 5 shows the results obtained in the case of using mutant SOD1s until the 65th mutant SOD1 in 122 types of mutant SOD1s.

FIG. 6 shows evaluation of the binding inhibitory activity of Example Compound 1 on intracellular SOD1-Derlin-1 binding according to a co-immunoprecipitation experiment. FIG. 6 shows the results obtained in the case of using, mutant SOD1s until the 81st mutant SOD1 in 122 types of mutant SOD Is.

FIG. 7 shows evaluation of the binding inhibitory activity of Example Compound 1 on intracellular SOD1-Derlin-1 binding according to a co-immunoprecipitation experiment. FIG. 7 shows the results obtained in the case of using mutant SOD1s until the 96th mutant SOD1 in 122 types of mutant SOD1s.

FIG. 8 shows evaluation of the binding inhibitory activity of Example Compound 1 on intracellular SOD1-Derlin-1 binding according to a co-immunoprecipitation experiment. FIG. 8 shows the results obtained in the case of using mutant SOD1s until the 111th mutant SOD1 in 122 types of mutant SOD1s.

FIG. 9 shows evaluation of the binding inhibitory activity of Example Compound 1 on intracellular SOD1-Derlin-1 binding according to a co-immunoprecipitation experiment. FIG. 9 shows the results obtained in the case of using mutant SOD1s until the 122nd mutant SOD1 in 122 types of mutant SOD1s.

FIG. 10A shows a Kaplan-Meier curve regarding an onset (a period of time required until the onset of the pathologic conditions) defined based on a reduction in motor function, after a rotarod test has been carried out, at longest, for 300 seconds, while setting the reached rotation speed at 40 rpm and the acceleration time at 180 seconds. FIG. 10B shows a Kaplan-Meier curve regarding a survival period.

FIG. 11 shows photomicrographs of Nissl-stained sections. Frozen spinal cord sections (40 μm) of 31-week-old SOD1 G93A transgenic mouse group and 34-week-old WI mice were subjected to Nissl staining and were then observed under a microscope. Typical Nissl stained images of the lumbar cord anterior horn are shown. The arrow indicates a motor neuron.

FIG. 12 shows the results obtained by counting the number of motor neurons in a Nissl-stained section (mean±s.e.m.). WT (wild-type) mice: n=4; and DMSO-administered or Example Compound 1-administered SOD1 G93A transgenic mice: n=8 in each group. *p<0.05; Student's t-test.

DESCRIPTION OF EMBODIMENTS

Figure 10A:
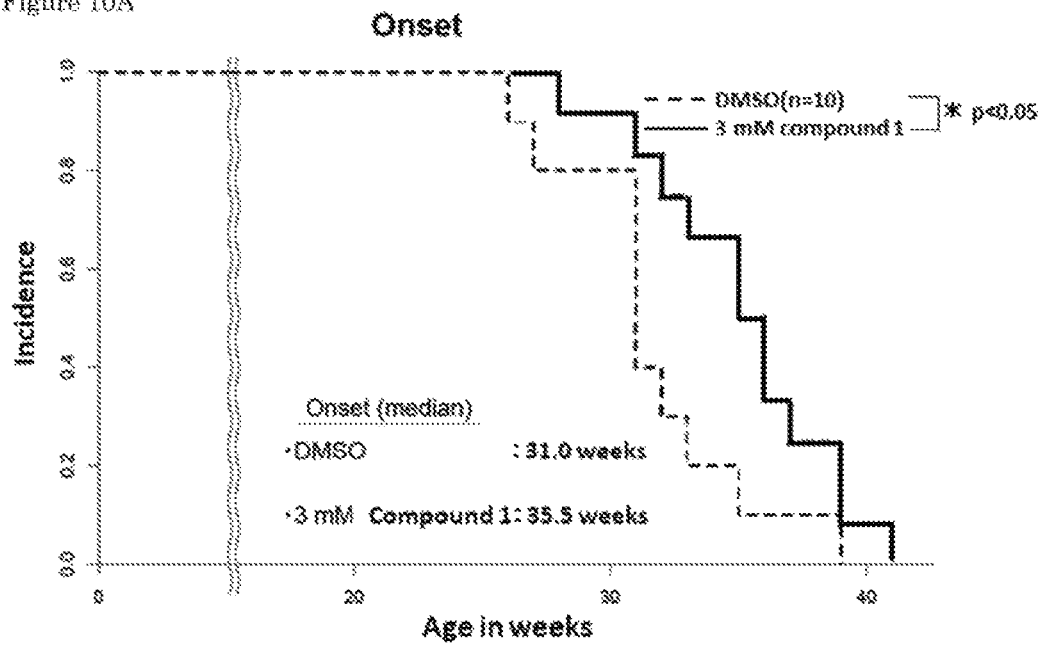
FIGS. 10A and 10B show the influence of Example Compound 1 on ALS model mice, in terms of a period of time required until the onset of the pathologic conditions and a survival period, after administration of Example Compound 1 to the ALS model mice.

A first embodiment of the present invention relates to the compound represented by the above formula (1) (the above formulae (1a) and (1b)) or a salt thereof, or a solvate or hydrate thereof.

In the Formula (1),

X represents a sulfur atom or —CH=CH—.

$R_1$ represents any one of a 1,2,3,4-tetrahydroquinolyl group (or a 3,4-dihydro-1(2H)-quinolyl group), a 3,4-dihydro-4,4-dimethyl-1(2H)-quinolyl group, a 2,3,4,5-tetrahydro-1H-1-benzazepinyl group, or a substituent represented by the formula (2).

$R_2$ represents a hydrogen atom, a lower alkyl group, a lower acyl group, or an unsubstituted or optionally substituted aromatic lower alkyl group. Herein, the "lower alkyl" means a linear, branched or cyclic hydrocarbon containing 1 to 20, and preferably 1 to 10 carbon atoms, or a hydrocarbon consisting of the combination thereof. Examples of such lower alkyl include methyl, ethyl, and butyl. The "lower acyl" means acyl containing 1 to 20, and preferably 1 to 10 carbon atoms. Examples of such lower acyl include acetyl, propionyl, and butyloyl. In addition, the "optionally substituted aromatic lower alkyl group" is, for example, a 4-methoxybenzyl group. When the phrase "optionally substituted" is used for a certain functional group in the present description, the number of substituents or the position of substituents is not particularly limited.

$R_3$ represents a hydrogen atom.

Otherwise, $R_2$ and $R_3$ may bind to each other to form a ring. Examples of $R_2$ and $R_3$ that may bind to each other to form a ring include a pyrrolidine ring bound by a butylene chain and a piperidine ring bound by a pentylene chain.

Moreover, in the formula (2), $R_4$ represents an unsubstituted or optionally substituted phenyl group, an unsubstituted or optionally substituted pyridyl group, or an unsubstituted or optionally substituted naphthyl group, and $R_5$ represents a hydrogen atom, a lower alkyl group, a lower alkenyl group, a lower alkynyl group (optionally containing an oxygen atom and/or a double bond), or an unsubstituted or optionally substituted aromatic lower alkyl group. In addition, examples of the "optionally substituted aromatic lower alkyl group" include a 4-methoxybenzyl group and a benzyl group.

Regarding $R_4$, examples of the "unsubstituted or optionally substituted phenyl group" include a phenyl group, a 4-fluorophenyl group, a 2,3,4-trifluorophenyl group, a 4-iodophenyl group, a 2,4-difluorophenyl group, a 2,3-difluorophenyl group, a 2,5-difluorophenyl group, a 3,5-difluorophenyl group, a 3,4-difluorophenyl group, a 5-fluoro-2-methylphenyl group, a 3-pentafluorosulfanylphenyl group, a 2,6-dimethylphenyl group, a 4-benzyloxyphenyl group, a 3,5-bis(trifluoromethyl)biphenyl group, a 3-trifluoromethylphenyl group, a 4-trifluoromethylphenyl group, a 4-tert-butylphenyl group, a 3-methoxyphenyl group, and a 4-methoxyphenyl group. Examples of the "unsubstituted or optionally substituted pyridyl group" include a 4-pyridyl group and a 2-iodo-4-pyridyl group. The "unsubstituted or optionally substituted naphthyl group" is, for example, a 1-naphthyl group.

Regarding $R_5$, the term "lower alkyl" is as described above. The "lower alkenyl" and the "lower alkynyl" mean hydrocarbon-based substituents each containing 1 to 20, and preferably 1 to 10 carbon atoms, having a double bond and a triple bond, respectively, and optionally containing an oxygen atom in some cases, and each consisting of a linear, branched or cyclic hydrocarbon or the combination thereof. The "lower alkyl group" is, for example, a 1-propyl group. Examples of the "lower alkenyl group" include a 2-butenyl group, a 3-methyl-2-butenyl group, a 2-propenyl(allyl) group, a 2-methyl-2-propenyl group, and a 2-cyclopentylideneethyl group. Examples of the "lower alkynyl group" include a 2-butynyl group, a 2-propynyl(propargyl) group, a (Z)-4-(prop-2-yloxy)but-2-enyl group, and an (E)-4-(prop-2-yloxy)but-2-enyl group. The "unsubstituted or optionally substituted aromatic lower alkyl group" is, for example, a benzyl group.

The salt of the compound represented by the formula (1) according to the embodiment of the present invention may be a pharmaceutically acceptable salt. For example, when an acidic group is present, examples of the salt include: alkaline metal and alkaline-earth metal salts, such as lithium, sodium, potassium, magnesium, or calcium; amine salts such as ammonia, methylamine, dimethylamine, trimethylamine, dicyclohexylamine, tris(hydroxymethyl)aminomethane, N,N-bis(hydroxyethyl)piperazine, 2-amino-2-methyl-1-propanol, ethanolamine, N-methylglucamine, or L-glucamine; and salts formed with basic amino acids such as lysine, δ-hydroxylysine, or arginine. When a basic group is present, examples of the salt include: salts formed with mineral acids such as hydrochloric acid, hydrobromic acid, sulfuric acid, nitric acid, or phosphoric acid; salts formed with organic acids such as methanesulfonic acid, benzenesulfonic acid, p-toluenesulfonic acid, acetic acid, propionate, tartaric acid, fumaric acid, maleic acid, malic acid, oxalic acid, succinic acid, citric acid, benzoic acid, mandelic acid, cinnamic acid, lactic acid, glycolic acid, glucuronic acid, ascorbic acid, nicotinic acid, or salicylic acid; and salts formed with acidic amino acids such as aspartic acid or glutamic acid.

Furthermore, the compound represented by the formula (1) according to the embodiment of the present invention includes stereoisomers such as a tautomer or an enantiomer, unless otherwise specified. That is to say, when the compound represented by the formula (1) comprises one or two or more asymmetric carbons, with regard to the stereochemistry of the asymmetric carbons, they may each independently have either an (R) form or an (S) form, and may be present in the form of a stereoisomer of the derivative, such as an enantiomer or a diastereoisomer.

The compound represented by the formula (1) according to the embodiment of the present invention is not limited, but examples of the present compound include the following:

N-allyl-3-amino-N-phenyl-6-(3-pyridinyl)thieno[2,3-b]pyridine-2-carboxamide,

N-propargyl-3-amino-N-phenyl-6-(3-pyridinyl)thieno[2,3-b]pyridine-2-carboxamide, (3-amino-6-(3-pyridinyl)thieno[2,3-b]2-pyridinyl)(3,4-dihydro-1(2H)-quinolinyl)methanone, 3-amino-N-(4-pyridinyl)-6-(3-pyridinyl)thieno[2,3-b]pyridine-2-carboxamide, 3-amino-N-(trans-2-butenyl)-N-phenyl-6-(3-pyridinyl)thieno[2,3-b]pyridine-2-carboxamide, 3-amino-N-(4-pyridinyl)-6-(2-pyridinyl)thieno[2,3-b]pyridine-2-carboxamide, 3-amino-N-(4-(3',5'-bis(trifluoromethyl)biphenyl)-6-(4-pyridinyl)thieno[2,3-b]pyridine-2-carboxamide, N-allyl-3-amino-N-(2,5-difluorophenyl)-6-(4-pyridinyl)thieno[2,3-b]pyridine-2-carboxamide, 3-amino-N-(2-butynyl)-N-phenyl-6-(3-pyridinyl)thieno[2,3-b]pyridine-2-carboxamide,
N-n-propyl-3-amino-N-phenyl-6-(3-pyridinyl)thieno[2,3-b]pyridine-2-carboxamide,
N-n-propyl-3-amino-N-(2,3,4-trifluorophenyl)-6-(3-pyridinyl)thieno[2,3-b]pyridine-2-carboxamide,
N-allyl-3-amino-N-(4-iodophenyl)-6-(3-pyridinyl)thieno[2,3-b]pyridine-2-carboxamide,
N-(3-methyl-2-butenyl)-3-amino-N-phenyl-6-(3-pyridinyl)thieno[2,3-b]pyridine-2-carboxamide,
[3-amino-6-(3-pyridinyl)thieno[2,3-b]2-pyridinyl](2,3,4,5-tetrahydro-1H-benzo[b]azepin-1-yl)methanone,
N-allyl-3-amino-N-(2,4-difluorophenyl)-6-(3-pyridinyl)thieno[2,3-b]pyridine-2-carboxamide,
N-allyl-3-amino-N-(2,3-difluorophenyl)-6-(3-pyridinyl)thieno[2,3-b]pyridine-2-carboxamide,
N-allyl-3-amino-N-(2,5-difluorophenyl)-6-(3-pyridinyl)thieno[2,3-b]pyridine-2-carboxamide,
N-allyl-3-amino-N-(5-fluoro-2-methylphenyl)-6-(3-pyridinyl)thieno[2,3-b]pyridine-2-carboxamide,
N-allyl-3-amino-N-(3,4-difluorophenyl)-6-(4-pyridinyl)thieno[2,3-b]pyridine-2-carboxamide,
N-allyl-3-amino-N-(3,5-difluorophenyl)-6-(3-pyridinyl)thieno[2,3-b]pyridine-2-carboxamide,
N-allyl-3-amino-N-(3-(pentafluoro-$\lambda^6$-sulfanyl)phenyl)-6-(3-pyridinyl)thieno[2,3-b]pyridine-2-carboxamide,
N-allyl-3-amino-N-(3,5-difluorophenyl)-6-(4-pyridinyl)thieno[2,3-b]pyridine-2-carboxamide,
N-allyl-3-amino-N-(3-(pentafluoro-$\lambda^6$-sulfanyl)phenyl)-6-(4-pyridinyl)thieno[2,3-b]pyridine-2-carboxamide,
3-amino-N-(1-naphthyl)-N-phenyl-6-(3-pyridinyl)thieno[2,3-b]pyridine-2-carboxamide,
3-amino-N-(2,6-dimethylphenyl)-6-(3-pyridinyl)thieno[2,3-b]pyridine-2-carboxamide,
3-amino-N-[4-(benzyloxy)phenyl]-6-(3-pyridinyl)thieno[2,3-b]pyridine-2-carboxamide,
3-amino-N-(4-iodophenyl)-6-(3-pyridinyl)thieno[2,3-b]pyridine-2-carboxamide,
3-amino-N-(2-iodo-4-pyridinyl)-6-(3-pyridinyl)thieno[2,3-b]pyridine-2-carboxamide,
3-amino-6-(3-pyridinyl)-N-(4-(trifluoromethyl)phenyl)thieno[2,3-b]pyridine-2-carboxamide,
3-amino-N-(3',5'-bis(trifluoromethyl)-[1,1'-biphenyl]-4-yl)-6-(3-pyridinyl)thieno[2,3-b]pyridine-2-carboxamide,
3-amino-6-(4-pyridinyl)-N-(3-(trifluoromethyl)phenyl)thieno[2,3-b]pyridine-2-carboxamide,
3-amino-N-(4-pyridinyl)-6-(4-pyridinyl)thieno[2,3-b]pyridine-2-carboxamide,
3-amino-N-(4-pyridinyl)-6-(5-pyrimidinyl)thieno[2,3-b]pyridine-2-carboxamide,
3-amino-N-(4-fluorophenyl)-N-(2-methylprop-2-en-1-yl)-6-(3-pyridinyl)thieno[2,3-b]pyridine-2-carboxamide,
3-amino-N-(4-fluorophenyl)-N-(prop-2-yn-1-yl)-6-(3-pyridinyl)thieno[2,3-b]pyridine-2-carboxamide,
3-amino-N-phenyl-N—((Z)-4-(prop-2-yloxy)but-2-enyl)-6-(3-pyridinyl)thieno[2,3-b]pyridine-2-carboxamide,
3-amino-N-benzyl-N-phenyl-6-(3-pyridinyl)thieno[2,3-b]pyridine-2-carboxamide,
3-amino-N-((E)-4-(pent-4-ynyloxy)but-2-enyl)-N-phenyl-6-(3-pyridinyl)thieno[2,3-b]pyridine-2-carboxamide,
3-amino-N-prenyl-N-(4-pyridinyl)-6-(3-pyridinyl)thieno[2,3-b]pyridine-2-carboxamide,
3-amino-N-(2-cyclopentylideneethyl)-N-phenyl-6-(3-pyridinyl)thieno[2,3-b]pyridine-2-carboxamide,
3-amino-6-(3-pyridinyl)thieno[2,3-b]2-pyridinyl)(3,4-dihydro-4,4-dimethyl-1(2H)-quinolinyl)methanone,
5-amino-N-phenyl-N-prenyl-2-(pyridin-3-yl)quinoline-6-carboxamide,
3-amino-N-(4-tert-butylphenyl)-N-(3-methylbut-2-en-1-yl)-6-(4-pyridinyl)thieno[2,3-b]pyridine-2-carboxamide,
3-amino-6-(4-pyridinyl)thieno[2,3-b]2-pyridinyl)(3,4-dihydro-4,4-dimethyl-1(2H)-quinolyl)methanone,
3-amino-N-(3-methoxyphenyl)-N-prenyl-6-(4-pyridinyl)thieno[2,3-b]pyridine-2-carb oxamide,
3-amino-N-(4-methoxyphenyl)-N-prenyl-6-(4-pyridinyl)thieno[2,3-b]pyridine-2-carb oxamide, and
3-amino-N-metallyl-N-phenyl-6-(4-pyridinyl)thieno[2,3-b]pyridine-2-carboxamide.

A second embodiment of the present invention relates to: an ALS- (in particular, FALS-) related mutant SOD1-Derlin-1 binding inhibitor (an agent for inhibiting the binding between ALS-related mutant SOD1 and Derlin-1) comprising, as an active ingredient, the compound represented by the above formula (1) or a salt thereof, or a solvate or hydrate thereof; or a medicament or a pharmaceutical composition, comprising, as an active ingredient, the compound represented by the above formula (1) or a salt thereof, or a solvate or hydrate thereof; or a medicament or a pharmaceutical composition, comprising the aforementioned ALS-related mutant SOD1-Derlin-1 binding inhibitor.

In addition, the medicament or the pharmaceutical composition according to the second embodiment of the present invention is administered to patients suffering from ALS (in particular, from FALS), so that it can be used to treat ALS.

Herein, the "ALS-related mutant SOD1" means an SOD1 mutant associated with the onset of the pathologic conditions of ALS. Examples of the ALS-related mutant SOD1 include 122 types of known mutants (see Fujisawa et al., Ann Neurol 72, 739-749, (2012), WO2011/142461). Specific examples of such SOD1 mutation include K3E, A4S, A4T, A4V, V5L, C6F, C6G, C6Y, L8Q, L8V, G10R, G10V, G12R, V14G, V14M, G16A, G16S, N19S, F20C, Q22L, V29A, V29+, G37R, L38R, L38V, E40G, G41D, G41S, H43R, F45C, H46R, V47A, V47F, H48Q, H48R, E49K, C57R, S59I, N65S, P66A, G72C, G72S, D76V, D76Y, H80R, L84F, L84V, N86S, G85R, G85S, N86D, N86I, N86K, V87A, V87M, T88A, A89T, A89V, D90A, D90V, G93A, G93C, G93D, G93R, G93S, G93V, A95T, A95V, V97L, V97M, 199V, E100G, E100K, D101G, D101H, D101N, D101Y, I104F, S105L, S105A, L106V, G108V, C111Y, I112M, I112T, I113F, I113T, G114A, R115G, T116R, L117V, V118L, L118+, D124G, D124V, D125H, L126S, L126*, L126A, G127+, E132+, E133V, E133Δ, S134N, N139D, N139H, N139K, A140G, G141E, G141*, L144F, L144S, A145G, A145T, C146R, C146*, G147D, G147R, V148G, I149T, I151S, and I151T (wherein the symbol Δ indicates deletion mutation, the symbol + indicates insertion mutation, and the symbol * indicates termination mutation, respectively).

Further, still unknown SOD1 mutants that are associated with the onset of the pathologic conditions of ALS are also included in the "ALS-related mutant SOD1" described in the present description.

It is to be noted that the amino acid sequence and nucleotide sequence of wild-type (normal) human SOD1 have been registered in the database under GenBank Accession No. NM_000454.

With regard to the ALS-related mutant SOD1-Derlin-1 binding inhibitor and the medicament according to the embodiment of the present invention, the compound represented by the formula (1) or a salt thereof, or a solvate or hydrate thereof, which is used as an active ingredient, may be directly administered to patients. However, in general, the ALS-related mutant SOD1-Derlin-1 binding inhibitor and the medicament are desirably administered in the form of a pharmaceutical composition comprising such a substance used as an active ingredient and one or two or more pharmaceutical additives.

Otherwise, two or more types of the compounds represented by the formula (1) may be used in combination, as active ingredients of the ALS-related mutant SOD1-Derlin-1 binding inhibitor or the medicament according to the embodiment of the present invention. The above-described pharmaceutical composition may comprise known components that are effective for the treatment of ALS.

Examples of the dosage form of the medicament or the pharmaceutical composition according to the present invention include a tablet, a capsule, a granule agent, a powder agent, syrup, a suspension, a suppository, an ointment, a cream agent, gel, a patch, an inhalant, and an injection. These agents are prepared according to ordinary methods. Besides, in the case of a liquid preparation, the preparation may be dissolved or suspended in water or another suitable solvent at time of use. Moreover, a tablet agent and a granule agent may be coated by a publicly known method. In the case of an injection, it is prepared by dissolving the compound of the present invention in water. The present compound may also be dissolved in a normal saline or a glucose solution, as necessary, and also, a buffer or a preservative may be added thereto.

A preparation for oral administration or parenteral administration is provided in the form of any given preparation. Examples of the preparation form that can be prepared herein include: medicaments or pharmaceutical compositions for oral administration, having a form such as a granule agent, a fine granule agent, a powder agent, a hard capsule, a soft capsule, syrup, an emulsion, a suspension, or a liquid agent; and medicaments or pharmaceutical compositions for parenteral administration such as intravenous administration, intramuscular administration, or a subcutaneous administration, having a form such as an injection, a drop agent, a percutaneous absorption agent, a transmucosal absorption agent, a transnasal agent, an inhalant, or a suppository. An injection, a drop agent, and the like may also be prepared in a powdery dosage form such as a freeze-dried form, and may be then dissolved in an appropriate aqueous medium such as a normal saline at time of use.

The types of pharmaceutical additives used in the production of the medicament or the pharmaceutical composition according to the present invention, the ratio of pharmaceutical additives to the active ingredient, or a method for producing the medicament or the pharmaceutical composition can be selected, as appropriate, by a person skilled in the art, depending on the form thereof. As such pharmaceutical additives, inorganic or organic substances, or solid or liquid substances can be used. In general, the pharmaceutical additives may be mixed at a weight percentage of 1% by weight to 90% by weight, with respect to the weight of the active ingredient. Specifically, examples of the pharmaceutical additive include lactose, glucose, mannit, dextrin, cyclodextrin, starch, sucrose, magnesium aluminometasilicate, synthetic aluminum silicate, carboxymethylcellulose sodium, hydroxypropyl starch, carboxymethylcellulose calcium, ion exchange resin, methyl cellulose, gelatin, gum arabic, hydroxypropyl cellulose, hydroxypropylmethyl cellulose, polyvinylpyrrolidone, polyvinyl alcohol, light anhydrous silicic acid, magnesium stearate, talc, Tragacanth, bentonite, veegum, titanium oxide, sorbitan fatty acid ester, sodium lauryl sulfate, glycerin, fatty acid glycerin ester, purified lanolin, glycerinated gelatin, polysorbate, macrogol, vegetable oil, wax, liquid paraffin, white petrolatum, fluorocarbon, nonionic surfactant, propylene glycol, and water.

In order to produce a solid agent for oral administration, an active ingredient is mixed with an excipient component such as lactose, starch, crystalline cellulose, calcium lactate or anhydrous silicic acid to form a powder agent. Otherwise, as necessary, a binder such as saccharose, hydroxypropyl cellulose or polyvinylpyrrolidone, a disintegrator such as carboxymethyl cellulose or carboxymethylcellulose calcium, and other additives are further added to the mixture, and the obtained mixture is then subjected to wet or dry granulation, so as to form a granule agent. Moreover, in order to produce a tablet, such a powder agent or a granule agent may be directly subjected to tableting, or a lubricant such as magnesium stearate or talc may be added to the powder agent or granule agent, and the obtained mixture may be then subjected to tableting. Such a granule agent or a tablet may be coated with an enteric coating base such as hydroxypropylmethyl cellulose phthalate or a methacrylic acid-methyl methacrylate polymer, so as to prepare an enteric-coated agent. Alternatively, such a granule agent or a tablet may also be coated with ethyl cellulose, carnauba wax, hydrogenated oil or the like, so as to prepare a sustained release agent. Furthermore, in order to produce a capsule, a powder agent or a granule agent is filled into a hard capsule. Otherwise, the active ingredient is directly coated with a gelatin film, or it is dissolved in glycerin, polyethylene glycol, sesame oil, olive oil or the like, and is then coated with a gelatin film, so as to prepare a soft capsule.

In order to produce an injection, the active ingredient, and as necessary, a pH adjuster such as hydrochloric acid, sodium hydroxide, lactose, lactic acid, sodium, sodium monohydrogen phosphate or sodium dihydrogen phosphate, and an isotonizing agent such as sodium chloride or glucose, are dissolved in distilled water for injection, and the obtained solution is then subjected to aseptic filtration, and the resultant is then filled into an ampule. Otherwise, mannitol, dextrin, cyclodextrin, gelatin and the like are further added to the obtained solution, followed by vacuum-freeze drying, so as to prepare an injection that is to be dissolved when used. Moreover, lecithin, polysorbate 80, polyoxyethylene hydrogenated castor oil or the like is added to the active ingredient, and the mixture is then emulsified in water, so as to prepare an emulsion for injection.

In order to produce an agent for rectal administration, the active ingredient, together with a suppository base material such as cacao butter, fatty acid tri-, di- and mono-glycerides, or polyethylene glycol, is dissolved by humidification, and the obtained solution is then poured into a mold, followed by cooling. Otherwise, the active ingredient may be dissolved in polyethylene glycol, soybean oil or the like, and the obtained solution may be then coated with a gelatin film.

The applied dose and the number of doses of the medicament or the pharmaceutical composition according to the present invention are not particularly limited. The applied dose and the number of doses can be selected, as appropriate, by a doctor's decision, depending on various conditions such as the purpose of prevention and/or treatment of deterioration and/or progression of a treatment target disease, the type of the disease, the body weight, age and other conditions of a patient, etc.

In general, the applied dose is approximately 0.01 to 1000 mg (the weight of the active ingredient) per adult per day via oral administration. Such a dose can be administered once or divided over several administrations per day, or every several days. When the medicament or the pharmaceutical composition according to the present invention is used as an injection, it is desired that a dose of 0.001 to 100 mg (the weight of the active ingredient) is administered per adult per day, continuously or intermittently.

Using a carrier capable of preventing the immediate elimination of an agent from the inside of a body, the medicament or the pharmaceutical composition according to the present invention can be prepared in the form of a sustained release agent such as an implanted tablet or a delivery system encapsulated into a microcapsule. As such carriers, there can be used biodegradable biocompatible polymers such as ethylene vinyl acetate, polyacid anhydride, polyglycolic acid, collagen, polyorthoester, and polylacetic acid. Such materials can be easily prepared by a person skilled in the art. In addition, a liposome suspension can also be used as a pharmaceutically acceptable carrier. The type of an available liposome is not limited. Although a preparation method is not limited, the liposome can be passed through a filter with an appropriate pore size and can be then purified by a reverse-phase evaporation method, so that it can be prepared as a lipid composition containing phosphatidyl choline, cholesterol and a PEG derivative of phosphatidylethanol (PEG-PE), and having a size suitable for use.

The medicament or the pharmaceutical composition according to the present invention may be provided in the form of a kit, together with an instruction manual that describes an administration method, etc. An agent contained in the kit effectively maintains the activity of constituents of the medicament or the pharmaceutical composition for a long period of time, does not adsorb on the inside of a vessel, and is supplied from a vessel made from a material that does not deteriorate the constituents. For example, a sealed glass ampule may comprise a buffer or the like, which has been sealed in the presence of a neutral non-reactive gas such as nitrogen gas.

In addition, an instruction manual may be attached to the kit. The instruction manual for the kit may be printed on a paper or other materials, or may be stored in an electromagnetically readable medium, such as CD-ROM or DVD-ROM, and may be then supplied in such a form to a user.

Further, a third embodiment of the present invention relates to a method for treating ALS, and in particular, FALS, by administering the medicament or the pharmaceutical composition according to the second embodiment of the present invention to a treatment target.

Herein, the term "treatment" is used to mean that the progression and deterioration of the pathological conditions of a disease are inhibited or alleviated in a mammal that has been affected with the disease or the like, and thereby, the term "treatment" is used to mean a therapeutic means directed towards inhibiting or alleviating the progression and deterioration of the disease.

The "mammal" as a treatment target means any given animal classified into Mammalia, and the type of the mammal is not particularly limited. Examples of such a mammal include humans, pet animals such as a dog, a cat or a rabbit, and livestock animals such as a bovine, a swine, sheep or a horse. A particularly preferred "mammal" is a human.

Among the compounds represented by the formula (1), for example, a thieno[2,3-b]pyridine derivative compound (substituted thieno[2,3-b]pyridine-2-carboxamide), wherein any of $A_1$ to $A_4$ represents a nitrogen atom, $R_2$ and $R_3$ each represent a hydrogen atom, and $R_4$ or $R_5$ represents a phenyl group having a substituent, can be produced by the following method (Scheme 1).

Scheme 1

[Formula 7]

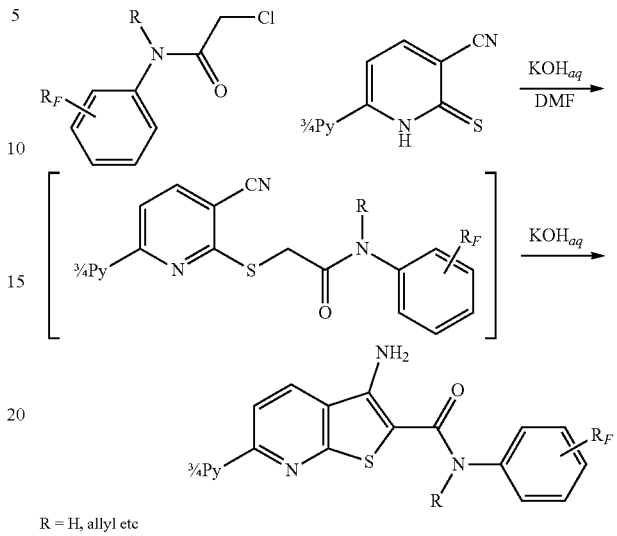

R = H, allyl etc

Common Synthetic Method (1) of Substituted thieno[2,3-b]pyridine-2-carboxamide

An aqueous potassium hydroxide solution (10%, 0.15 mL) is added to an N,N-dimethylformamide (DMF) (1 mL) suspension of
6-(pyridin-2-yl)-3-cyanopyridine-2-(1H)-thione,
6-(pyridin-3-yl)-3-cyanopyridine-2-(1H)-thione,
6-(pyridin-4-yl)-3-cyanopyridine-2-(1H)-thione or
6-(pyrimidin-5-yl)-3-cyanopyridine-2-(1H)-thione (53.5 mg, 0.25 mmol, 1.0 equiv).
Subsequently, appropriately substituted α-chloroacetamide (0.25 mmol, 1.0 equiv) is added to the mixture at room temperature. Thereafter, the mixture is stirred at room temperature overnight, and an aqueous potassium hydroxide solution (10%, 0.15 mL) is additionally added to the reaction mixture. The obtained reaction mixture is stirred overnight, and is then diluted with 50 mL of water. A precipitate is collected by filtration, and is then purified by recrystallization from a suitable solvent or column chromatography, so that the compound of the present invention can be obtained.

Otherwise, the compound of the present invention can also be produced by the below-mentioned method.

Common Synthetic Method (2) of Substituted thieno[2,3-b]pyridine-2-carboxamide

Triethylamine (542 μL, 0.375 mmol, 1.5 equiv.) is added to an N,N-dimethylformamide (DMSO) (1 mL) suspension of
6-(pyridin-2-yl)-3-cyanopyridine-2-(1H)-thione,
6-(pyridin-3-yl)-3-cyanopyridine-2-(1H)-thione,
6-(pyridin-4-yl)-3-cyanopyridine-2-(1H)-thione, or
6-(pyrimidin-5-yl)-3-cyanopyridine-2-(1H)-thione (53.5 mg, 0.25 mmol, 1.0 equiv).
Subsequently, appropriately substituted α-chloroacetamide (0.25 mmol, 1.0 equiv) is added to the mixture at room temperature, and the obtained mixture is then stirred overnight. After that, 30 mL of ethyl acetate is added to the reaction mixture. An organic acid phase is washed with 1 N hydrochloric acid, and is then dried over anhydrous sodium sulfate or the like. The solvent is distilled away, and an intermediate is then purified with a silica gel column. Subsequently, the intermediate is dissolved in a mixed solvent consisting of 1 mL of dioxane and 0.25 mL of water, and lithium hydroxide (55 mg) is then added to the obtained solution. The reaction mixture is stirred for 1 hour, and is then diluted with 50 mL of water. A precipitate is collected by filtration, and is then purified by recrystallization from a suitable solvent or column chromatography, so that the compound of the present invention can be obtained.

As a raw material compound used in the above-described production methods, a commercially available product can be directly used, or a method known to a person skilled in the art or a modification method thereof is applied to such a commercially available product to produce the raw material compound.

Hereinafter, the present invention will be specified in more detail in the following examples. However, these examples are not intended to limit the scope of the present invention.

EXAMPLES

Example 1

N-allyl-3-amino-N-phenyl-6-(3-pyridinyl)thieno[2,3-b]pyridine-2-carboxamide

[Formula 8]

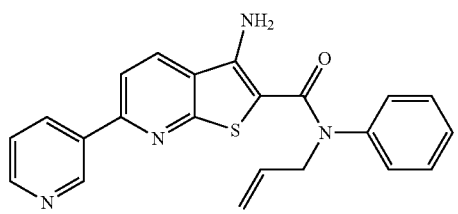

Synthesis of N-allyl-N-phenyl 6-(3-pyridinyl)-3-cyanopyridine-2-(1H)-thioacetamide 6-(3-Pyridinyl)-3-cyanopyridine-2-(1H)-thione (81 mg, 0.38 mmol) was dissolved in DMSO (0.5 mL), and triethylamine (79 µL, 1.5 equiv) was then added to the solution. Thereafter, a DMSO (0.5 mL) solution of N-allyl-N-phenyl-2-chloroacetamide (120 mg, 1.5 equiv) was added to the mixed solution at room temperature, while stirring. One hour later, water (10 mL) was added to the reaction mixture. The obtained mixture was extracted with ethyl acetate, an organic layer was then dried over anhydrous sodium sulfate, and the solvent was then distilled away. The residue was purified by silica gel column chromatography (ethyl acetate), so as to obtain N-allyl-N-phenyl-6-(3-pyridinyl)-3-cyanopyridine-2-(1H)-thioacetamide in the form of a white solid (133 mg, 91%).

Synthesis of N-allyl-3-amino-N-phenyl-6-(3-pyridinyl)thieno[2,3-b]pyridine-2-carboxamide N-allyl-N-phenyl 6-(3-pyridinyl)-3-cyanopyridine-2-(1H)-thioacetamide (100 mg) was dissolved in dioxane (0.5 mL), and water (0.1 mL) was then added to the obtained solution to obtain a light yellowish-white suspension. In such a state, lithium hydroxide (22 mg) was added to the suspension, so that the suspension was converted to a yellow solution. The solution was stirred for 45 minutes. Thereafter, water was added to the reaction solution. The obtained mixture was extracted with ethyl acetate and was then dried, and the solvent was then distilled away. The residue was purified by silica gel column chromatography (ethyl acetate), so as to obtain a yellow solid. This solid was recrystallized from a mixed solvent of dichloromethane and hexane to obtain a yellow crystal as a product of interest (61 mg, 61%). The physicochemical data of Example Compound 1 are shown in Table 1.

Example 2

N-propargyl-3-amino-N-phenyl-6-(3-pyridinyl)thieno[2,3-b]pyridine-2-carboxamide

[Formula 9]

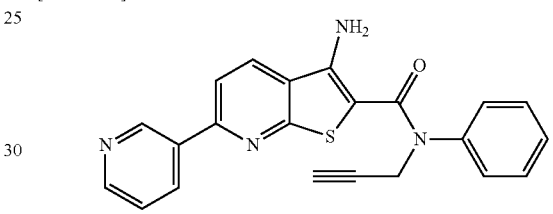

6-(3-Pyridinyl)-3-cyanopyridine-2-(1H)-thione (81 mg, 0.38 mmol) was dissolved in DMSO (0.5 mL), and triethylamine (79 µL, 1.5 equiv) was then added to the obtained solution. Thereafter, a DMSO (0.5 mL) solution of N-propargyl-N-phenyl-2-chloroacetamide (118 mg, 1.5 equiv) was added to the mixed solution at room temperature, while stirring. One hour later, water (10 mL) was added to the reaction mixture. The obtained mixture was extracted with ethyl acetate, an organic layer was then dried over anhydrous sodium sulfate, and the solvent was then distilled away. The residue was purified by silica gel column chromatography (ethyl acetate), so as to obtain N-propargyl-N-phenyl-6-(3-pyridinyl)-3-cyanopyridine-2-(1H)-thioacetamide in the form of a light yellow solid (129 mg, 88%). This thioacetamide form (99 mg) was dissolved in dioxane (0.5 mL), and water (0.1 mL) was then added to the obtained solution to obtain a light yellowish-white suspension. In such a state, lithium hydroxide (22 mg) was added to the suspension, so that the suspension was converted to a yellow solution. The solution was stirred for 45 minutes. Thereafter, water was added to the reaction solution. The obtained mixture was extracted with ethyl acetate and was then dried, and the solvent was then distilled away. The residue was purified by silica gel column chromatography (ethyl acetate), so as to obtain a yellow solid. This solid was recrystallized from a mixed solvent of dichloromethane and hexane to obtain a yellow crystal as a product of interest (91 mg, 92%). The physicochemical data of Example Compound 2 are shown in Table 1.

Example 3

(3-Amino-6-(3-pyridinyl)thieno[2,3-b]2-pyridinyl)(3,4-dihydro-1(2H)-quinolyl)methanone

[Formula 10]

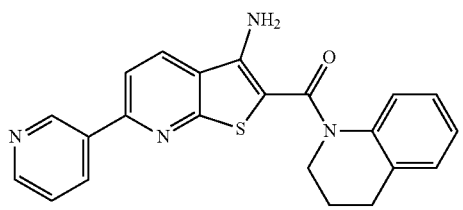

6-(3-Pyridinyl)-3-cyanopyridine-2-(1H)-thione (81 mg, 0.38 mmol) was dissolved in DMSO (0.5 mL), and triethylamine (79 µL, 1.5 equiv) was then added to the obtained solution. Thereafter, a DMSO (0.5 mL) solution of 2-chloro-1-(3,4-dihydro-1(2H)-quinolinyl)methanone (120 mg, 1.5 equiv) was added to the mixed solution at room temperature, while stirring. One and a half hours later, water (10 mL) was added to the reaction mixture. The obtained mixture was extracted with ethyl acetate, an organic layer was then dried over anhydrous sodium sulfate, and the solvent was then distilled away. The residue was purified by silica gel column chromatography (ethyl acetate), so as to obtain N-propargyl-N-phenyl-6-(3-pyridinyl)-3-cyanopyridine-2-(1H)-thio-1-(3,4-dihydro-1 (2H)-quinolinyl)methanone in the form of a light yellow solid (143 mg, 97.1%). This thioacetamide form (128.6 mg) was dissolved in dioxane (1 mL), and water (0.26 mL) was then added to the obtained solution to obtain a light yellowish-white suspension. In such a state, lithium hydroxide (28 mg) was added to the suspension, so that the suspension was converted to a yellow solution. The solution was stirred for 40 minutes. Thereafter, water was added to the reaction solution. The obtained mixture was extracted with ethyl acetate and was then dried, and the solvent was then distilled away. The residue was purified by silica gel column chromatography (ethyl acetate), so as to obtain a yellow solid. This solid was recrystallized from a mixed solvent of dichloromethane and hexane to obtain a yellow crystal as a product of interest (95 mg, 74%). The physicochemical data of Example Compound 3 are shown in Table 1.

Example 4 to Example 41 and Examples 43 to 47

With reference to the aforementioned common synthetic methods (1) and (2) of substituted thieno[2,3-b]pyridine-2-carboxamide, a raw material compound having a suitable substituent was used, as appropriate, and synthesis was carried out by the same method as those of Examples 1 to 3. The physicochemical data of the compounds of Example 4 to Example 41 and Examples 43 to 47 are shown in Table 1 to Table 7.

A method for producing the compound represented by the formula (1b) will be described below, taking a method for synthesizing a compound of Example 42 (Scheme 2) as an example. It is to be noted that the method for producing the compound represented by the formula (1b) is not limited to the below-mentioned example. The physicochemical data of the compound of Example 42 are shown in Table 6.

[Formula 11]

Scheme 2

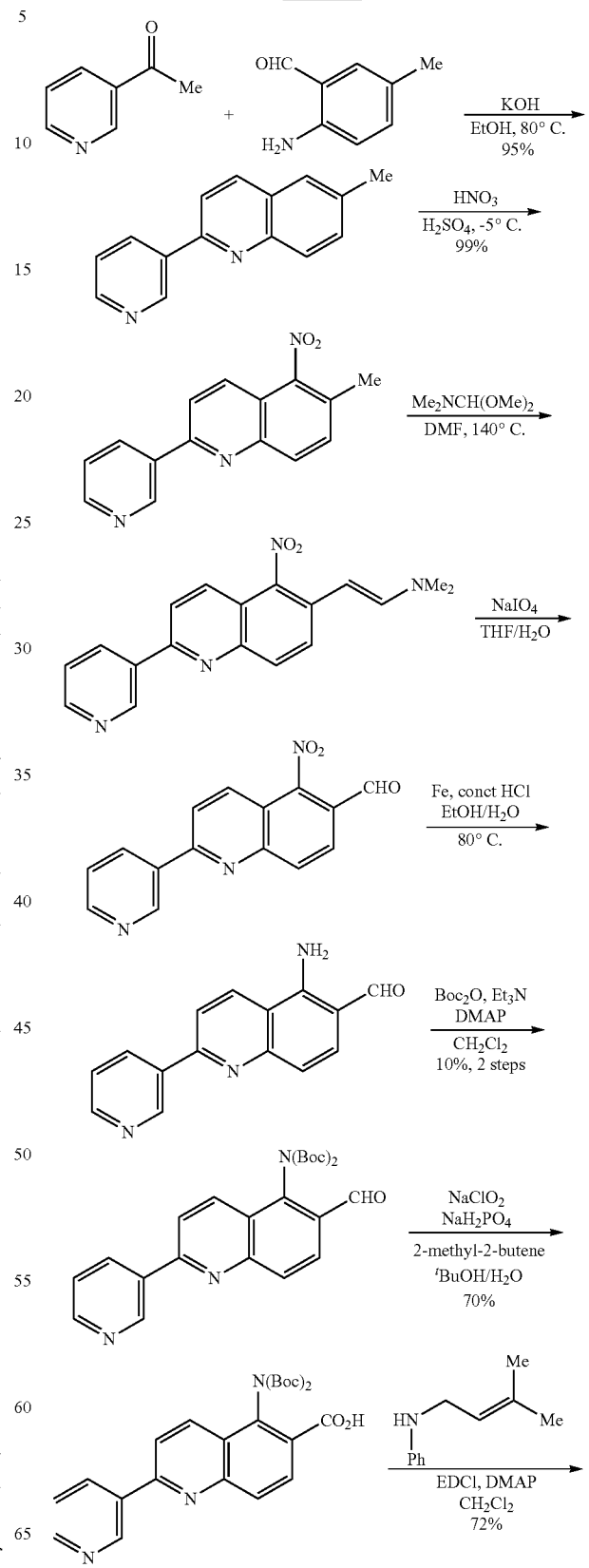

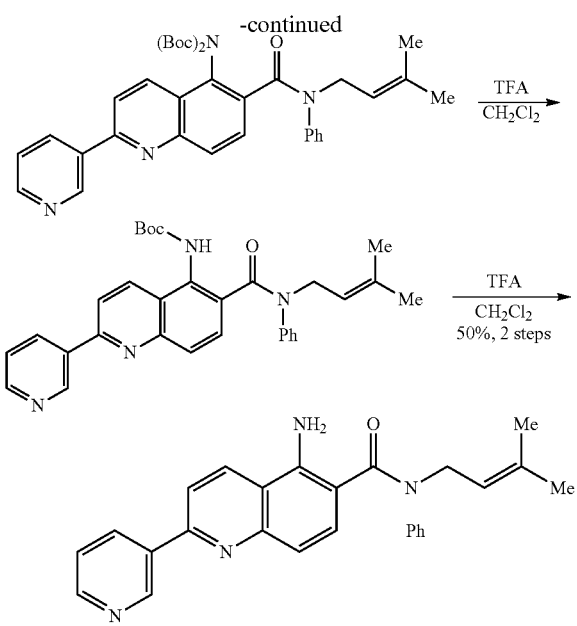

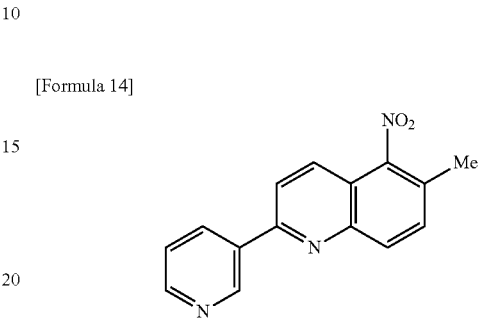

ethyl acetate, and was then washed with a saturated saline. The resultant was dried over anhydrous sodium sulfate, and the solvent was then distilled away under reduced pressure. The obtained crude resultant was purified by silica gel column chromatography (ethyl acetate:hexane=1:1 (v/v)) to obtain 1.03 g of the title compound g (yield: 95%).

6-Methyl-5-nitro-2-(pyridin-3-yl)quinoline

[Formula 14]

[Example 42] 5-Amino-N-phenyl-N-prenyl-2-(pyridin-3-yl)quinoline-6-carboxamide

[Formula 12]

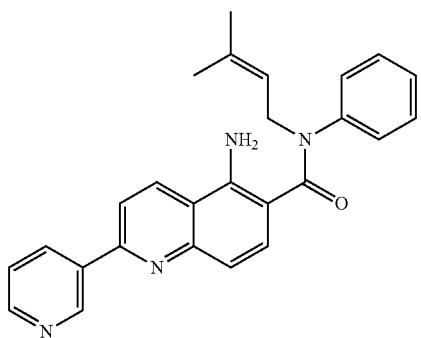

A mixed solution of nitric acid (0.10 ml) and sulfuric acid (1.0 ml) was added to 0.540 ml (496 mmol) of a sulfuric acid solution (0.35 ml) containing 105 mg (0.477 mmol) of 6-methyl-2-(pyridin-3-yl)quinoline, which had been cooled to −18° C., and the obtained mixture was then stirred at −5° C. for 4 hours. After completion of the reaction, the reaction solution was added to ice water, and an aqueous 15% sodium hydroxide solution was then added thereto to convert the mixed solution to a basic solution. The obtained solution was extracted with dichloromethane, and was then washed with water and a saturated saline. The resulting solution was dried over anhydrous sodium sulfate, and the solvent was then distilled away under reduced pressure, so as to obtain 125 mg of the title compound (yield: 99%).

(E)-N,N-dimethyl-2-(5-nitro-2-(pyridin-3-yl)quinolin-6-yl)ethenamine

6-Methyl-2-(pyridin-3-yl)quinoline

[Formula 13]

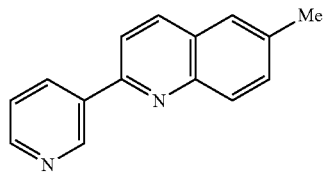

[Formula 15]

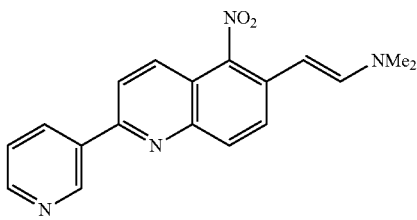

To a 300-ml egg-plant shaped flask, 803 mg (5.94 mmol) of 2-amino-5-methylbenzaldehyde, 0.540 ml (495 mmol) of 3-acetylpyridine, 113 mg (2.01 mmol) of potassium hydroxide, and 25 ml of ethanol were added, and the obtained mixture was then stirred at 80° C. for 7 hours. After completion of the reaction, water was added to the reaction mixture, and the thus obtained mixture was extracted with To a joint test tube equipped with a cooling pipe, 96.7 mg (0.365 mmol) of 6-methyl-5-nitro-2-(pyridin-3-yl)quinoline, 0.10 ml (0.73 mmol) of N,N-dimethylformamide dimethylacetal, and 0.40 ml of N,N-dimethylformamide were added, and the obtained mixture was then stirred at 140° C. for 2.5 hours. To the reaction mixture, 0.10 ml (0.73 mmol) of N,N-dimethylformamide dimethylacetal was added, and the thus obtained mixture was further stirred 140° C. for 2 hours. After completion of the reaction, the solvent was distilled away under reduced pressure, so as to obtain a crude resultant of the title compound.

5-Nitro-2-(pyridin-3-yl)quinoline-6-carboxaldehyde

[Formula 16]

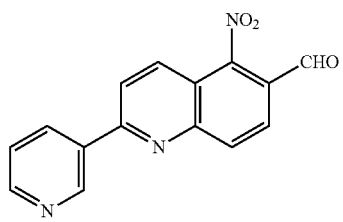

To a 10-ml egg-plant shaped flask, the above-obtained crude resultant of (E)-N,N-dimethyl-2-(5-nitro-2-(pyridin-3-yl)quinolin-6-yl)ethenamine, 477 mg (2.23 mmol) of sodium periodate, and 6.2 ml of tetrahydrofuran were added, and the obtained mixture was then stirred at room temperature for 2.5 hours. The reaction mixture was filtered, and thereafter, a saturated aqueous sodium hydrogen carbonate solution was added thereto. The obtained mixture was extracted with ethyl acetate, and was then washed with a saturated saline. The resultant was dried over anhydrous sodium sulfate, and the solvent was then distilled away under reduced pressure. The obtained crude resultant was purified by silica gel column chromatography (ethyl acetate) to obtain 23 mg of the title compound (yield: 23%).

5-Amino-2-(pyridin-3-yl)quinoline-6-carboaldehyde

[Formula 17]

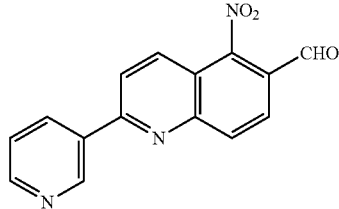

To a 10-ml egg-plant shaped flask, 124 mg (0.444 mmol) of 5-nitro-2-(pyridin-3-yl)quinoline-6-carboaldehyde, 196 mg (3.51 mmol) of iron, 0.40 ml of concentrated hydrochloric acid, 1.6 ml of water, and 3.2 ml of ethanol were added, and the obtained mixture was then stirred at 80° C. for 2 hours. To the reaction mixture, 95.8 mg (1.72 mmol) of iron was added, and the thus obtained mixture was further stirred at 80° C. for 1 hour. The reaction mixture was filtrated, was then extracted with chloroform, and was then washed with a saturated saline. The resultant was dried over anhydrous sodium sulfate, and the solvent was then distilled away under reduced pressure, so as to obtain a crude resultant of the title compound.

5-(bis(tert-Butoxycarbonyl)amino)-2-(pyridin-3-yl)quinoline-6-carboaldehyde

[Formula 18]

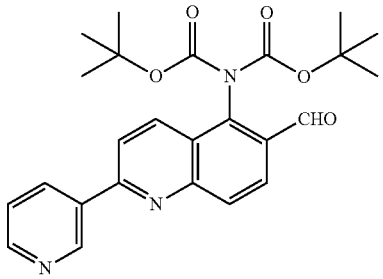

To a 20-ml egg-plant shaped flask, the above-obtained crude resultant of 5-amino-2-(pyridin-3-yl)quinoline-6-carboaldehyde, 153 mg (0.701 mmol) of di-tert-butyl bicarbonate, 4.1 mg (0.0336 mmol) of N,N-dimethyl-4-aminopyridine, 0.10 ml (0.717 mmol) of triethylamine, and 2.0 ml of dichloromethane were added, and the obtained mixture was then stirred at room temperature 1.5 hours. After completion of the reaction, the solvent was distilled away under reduced pressure. The obtained crude resultant was purified by silica gel column chromatography (ethyl acetate:hexane=3:1 (v/v)) to obtain 20.3 mg of the title compound (yield: 10%).

5-(bis(tert-Butoxycarbonyl)amino)-2-(pyridin-3-yl)quinoline-6-carboxylic Acid

[Formula 19]

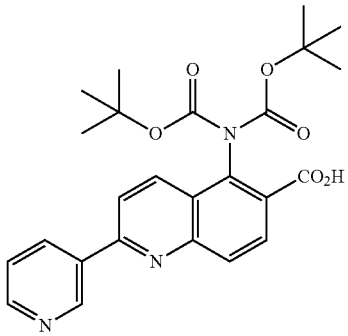

To 39.3 mg (0.0874 mmol) of 5-(bis(tert-butoxycarbonyl)amino)-2-(pyridin-3-yl)quinoline-6-carboaldehyde in a tert-butyl alcohol solution (1.6 ml), 21.1 mg (0.176 mmol) of sodium dihydrogen phosphate, 0.10 ml (0.87 mmol) of 2-methyl-2-butene, and water (0.40 ml) were added. To the obtained mixture, 17.3 mg (0.191 mmol) of sodium chlorite was added, and the thus obtained mixture was then stirred at room temperature for 1.5 hours. After completion of the reaction, an aqueous 10% sodium hydrogen sulfate solution and a saturated saline were added to the reaction mixture, and the thus obtained mixture was extracted with ethyl acetate, and was then washed with a saturated saline. The resultant was dried over anhydrous sodium sulfate, and the solvent was then distilled away under reduced pressure. The obtained crude resultant was purified by silica gel column chromatography (chloroform:methanol=9:1 (v/v)) and preparative thin-layer chromatography (chloroform:methanol=9:1 (v/v)), so as to obtain 28.6 mg of the title compound (yield: 70%).

5-(bis(tert-Butoxycarbonyl)amino)-N-phenyl-N-phenyl-2-(pyridin-3-yl)quinoline-6-carboxamide

[Formula 20]

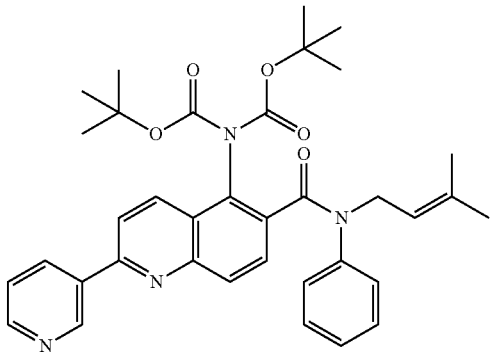

To a 10-ml pear-shaped flask, 28.6 mg (0.0614 mmol) of 5-(bis(tert-butoxycarbonyl)amino)-2-(pyridin-3-yl)quinoline-6-carboxylic acid, 24.0 mg (0.149 mmol) of N-prenylaniline, 43.6 mg (0.357 mmol) of N,N-dimethyl-4-aminopyridine, 35.1 mg (0.183 mmol) of 1-ethyl-3-(3-dimethylaminopropyl)carbodiimide hydrochloride, and 1.0 ml of dichloromethane were added, and the obtained mixture was then stirred at room temperature for 4.5 hours. After completion of the reaction, water was added to the reaction mixture, and the thus obtained mixture was extracted with ethyl acetate and was then washed with a saturated saline. The resultant was dried over anhydrous sodium sulfate, and the solvent was then distilled away under reduced pressure. The obtained crude resultant was purified by silica gel column chromatography (chloroform:methanol=19:1 (v/v)) to obtain 26.9 mg of the title compound (yield: 72%).

5-(tert-Butoxycarbonyl)amino-N-phenyl-N-prenyl-2-(pyridin-3-yl)quinoline-6-carboxamide

[Formula 21]

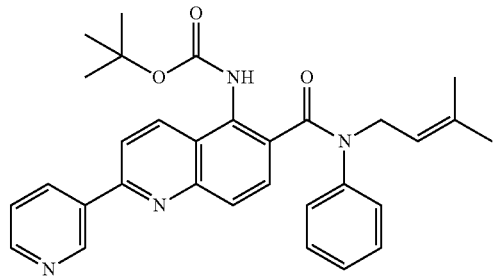

To a 10-ml pear-shaped flask, 25.4 mg (0.0417 mmol) of 5-(bis(tert-butoxycarbonyl)amino)-N-phenyl-N-prenyl-2-(pyridin-3-yl)quinoline-6-carb oxamide, 0.050 ml of trifluoroacetic acid, and 1.0 ml of dichloromethane were added, and the obtained mixture was then stirred at room temperature for 0.5 hours. To the reaction mixture, 0.050 ml of trifluoroacetic acid was added, and the thus obtained mixture was further stirred at room temperature for 0.5 hours. After completion of the reaction, a saturated aqueous sodium hydrogen carbonate solution was added to the reaction mixture, and the thus obtained mixture was extracted with chloroform, and was then washed with a saturated saline. The resultant was dried over anhydrous sodium sulfate, and the solvent was then distilled away under reduced pressure, so as to obtain a crude resultant of the title compound.

5-amino-N-phenyl-N-prenyl-2-(pyridin-3-yl)quinoline-6-carboxamide

[Formula 22]

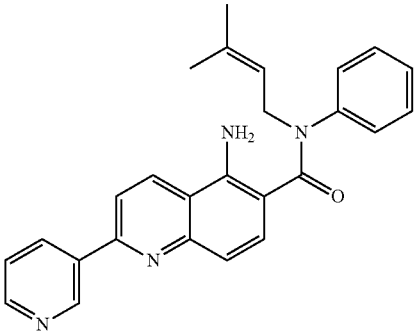

To a 10-ml pear-shaped flask, the above-obtained crude resultant of 5-(tert-butoxycarbonyl)amino-N-phenyl-N-prenyl-2-(pyridin-3-yl)quinoline-6-carboxamide, 0.10 ml of trifluoroacetic acid, and 1.0 ml of dichloromethane were added, and the obtained mixture was then stirred at room temperature for 9 hours. To the reaction mixture, a saturated aqueous sodium hydrogen carbonate solution was added, and the thus obtained mixture was extracted with chloroform, and was then washed with a saturated saline. The resultant was dried over anhydrous sodium sulfate, and the solvent was then distilled away under reduced pressure. The obtained crude resultant was purified by silica gel column chromatography (chloroform:methanol=80:1 (v/v)), preparative thin-layer chromatography (chloroform:methanol=9:1 (v/v)), and gel permeation chromatography (toluene), so as to obtain 8.5 mg of the title compound (yield: 50%).

TABLE 1

| Example | Structural formula | Compound name | Mass spectrometry and NMR |
|---|---|---|---|
| 1 | | N-allyl-3-amino-N-phenyl-6-(3-pyridinyl)thieno[2,3-b]pyridine-2-carboxamide | MS (ESI) m/z 386 [M$^+$]; $^1$H NMR (500 MHz, CDCl$_3$) δ 9.18 (d, J = 1.8 Hz, 1H), 8.64 (dd, J = 4.7, 1.4 Hz, 1H), 8.33-8.30 (m, 1H), 7.96 (d, J = 8.4, 1H), 7.69 (d, J = 8.4 Hz, 1H), 7.46-7.42 (m, 3H), 7.38 (dd, J = 8.0, 4.8 Hz, 1H), 7.34-7.30 (m, 2H), 6.40 (s, 2H), 6.01 (ddt, J = 17.5, 9.6, 6.1 Hz, 1H), 5.22-5.15 (m, 2H), 4.46 (d, J = 6.1 Hz, 2H). |
| 2 | | N-propargyl-3-amino-N-phenyl-6-(3-pyridinyl)thieno[2,3-b]pyridine-2-carboxamide | $^1$H NMR (500 MHz, CDCl$_3$) δ 9.18 (d, J = 1.8 Hz, 1H), 8.64 (dd, J = 4.8, 1.5 Hz, 1H), 8.37-8.26 (m, 1H), 7.96 (d, J = 8.4 Hz, 1H), 7.69 (d, J = 8.4 Hz, 1H), 7.51-7.45 (m, 3H), 7.45-7.40 (m, 2H), 7.38 (ddd, J = 8.0, 4.8, 0.6 Hz, 1H), 6.46 (s, 2H), 4.60 (d, J = 2.4 Hz, 2H), 2.29 (t, J = 2.4 Hz, 1H). |
| 3 | | (3-amino-6-(3-pyridinyl)thieno[2,3-b]2-pyridinyl)(3,4-dihydro-1(2H)-quinolinyl)methanone | $^1$H NMR (500 MHz, CDCl$_3$) δ 9.22 (d, J = 1.5 Hz, 1H), 8.68-8.62 (m, 1H), 8.38-8.32 (m, 1H), 7.98 (d, J = 8.4 Hz, 1H), 7.72 (d, J = 8.4 Hz, 1H), 7.39 (dd, J = 8.0, 4.8 Hz, 1H), 7.25-7.20 (m, 1H), 7.20-7.12 (m, 2H), 7.11-7.04 (m, 1H), 6.11 (s, 2H), 3.92 (t, J = 6.8 Hz, 2H), 2.81 (t, J = 6.6 Hz, 2H), 2.13-2.00 (m, 2H). |
| 4 | | 3-amino-N-(4-pyridinyl)-6-(3-pyridinyl)thieno[2,3-b]pyridine-2-carboxamide | MS (ESI) m/z 348 [(M + H)$^+$], 370 [(M + Na)$^+$] $^1$H-NMR (500 MHz, DMSO--d$_6$) δ: 9.82 (s, 1H), 9.37 (d, J = 2.0 Hz, 1H), 8.694 (dd, J = 4.7, 2.0 Hz, 1H), 8.691 (d, J = 8.5 Hz, 1H), 8.55 (dt, J = 8.0, 2.0 Hz, 1H), 8.44 (d, J = 6.2 Hz, 2H), 8.19 (d, J = 8.5 Hz, 1H), 7.77 (d, J = 6.2 Hz, 2H), 7.61 (s, 2H), 7.58 (dd, J = 8.0, 4.7 Hz, 1H) |
| 5 | | 3-amino-N-(trans-2-butenyl)-N-phenyl-6-(3-pyridinyl)thieno[2,3-b]pyridine-2-carboxamide | MS (ESI) m/z (%): 402 [M + Na]$^+$, 401 [M + H]$^+$. H NMR (500 MHz, CDCl$_3$): δ = 1.68 (dd, J = 1.3, 6.2 Hz, 3H, CH$_3$), 4.38 (dd, J = 0.9, 6.2 Hz, 2H, CH$_2$), 5.57 (m, 1H, CH) 5.66 (m, 1H, C=H), 6.37-6.41 (br s, 2H, NH$_2$), 7.27-7.31 (m, 2H, Ar), 7.38-7.45 (m, 4H, Ar), 7.68 (d, J = 8.3 Hz, 1H, Ar), 7.96 (d, J = 8.4 Hz, Ar), 8.35 (dt, J = 8.7, 1.5 Hz, 1H, Ar), 8.63 (dd, J = 1.5, 4.9 Hz, 1H, CH), 9.19 (d, J = 2.2 Hz, 1H, Ar) |
| 6 | | 3-amino-N-(4-pyridinyl)-6-(2-pyridinyl)thieno[2,3-b]pyridine-2-carboxamide | MS (ESI) m/z 348 [(M + H)$^+$], 370 [(M + Na)+] 1H-NMR (500 MHz, DMSO-d6) δ: 9.83 (s, 1H), 8.75 (brd, J = 4.4 Hz, 1H), 8.69 (d, J = 8.5 Hz, 1H), 8.483 (d, J = 8.5 Hz, 1H), 8.480 (m, 1H), 8.44 (d, J = 6.3 Hz, 2H), 8.01 (td, J = 7.5, 1.9 Hz, 1H), 7.77 (d, J = 6.3 Hz, 2H), 7.60 (s, 2H), 7.52 (dd, J = 7.5, 4.9 Hz, 1H) |
| 7 | | 3-amino-N-(4-(3',5'-bis(trifluoromethyl)biphenyl)-6-(4-pyridinyl)thieno[2,3-b]pyridine-2-carboxamide | MS (ESI) m/z 559 [(M + 1)$^+$]; $^1$H NMR (300 MHz, DMSO-d$_6$) δ: 9.71 (s, 1H), 8.75 (d, 2 H, J = 3.9 Hz), 8.70 (d, 1 H, J = 8.7 Hz), 8.34 (s, 2 H), 8.25 (d, 1 H, J = 8.4 Hz), 8.15 (d, 2 H, J = 4.2 Hz), 8.04 (s, 1 H), 7.91-7.89 (m, 4 H), 7.52 (s, 2 H) |

TABLE 2

| Example | Structural formula | Compound name | Mass spectrometry and NMR |
| --- | --- | --- | --- |
| 8 | | N-allyl-3-amino-N-(2,5-difluorophenyl)-6-(4-pyridinyl)thieno[2,3-b]pyrdine-2-carboxamide | MS (ESI) m/z 423 [(M + 1)$^+$]; $^1$H NMR (300 MHz, CDCl$_3$) δ: 8.59 (s, 2 H), 8.02 (d, 1 H, J = 8.1 Hz), 7.92 (s, 1 H), 7.77 (d, 2 H, J = 3.9 Hz), 7.58 (d, 1 H, J = 8.1 Hz), 7.05-6.95 (m, 2 H), 6.70 (s, 2 H), 5.93-5.85 (m, 1 H), 5.10-5.05 (m, 2 H), 4.33-4.32 (m, 2 H). |
| 9 | | 3-amino-N-(2-butynyl)-N-phenyl-6-(3-pyridinyl)thieno[2,3-b]pyridine-2-carboxamide | MS (ESI) m/z 421 [M + Na]$^+$, 399 [M + H]$^+$. $^1$H NMR (500 MHz, DMSO-d$_6$): δ = 1.75 (t, J = 2.4 Hz, 3 H, CH$_3$), 4.49 (d, J = 2.4 Hz, 2 H, CH$_2$), 7.38-7.41 (m, 2 H, Ar CH), 7.45-7.53 (m, 4 H, Ar CH), 7.55-7.60 (m, NH$_2$), 8.06 (d, J = 8.5 Hz, 1 H, Ar CH), 8.40-8.44 (m, 1 H, Ar CH), 8.54 (d, J = 8.5 Hz, 1 H, Ar CH), 8.62 (m, 1 H, Ar CH), 9.23 (s, 1 H, Ar CH); |
| 10 | | N-n-propyl-3-amino-N-phenyl-6-(3-pyridinyl)thieno[2,3-b]pyridine-2-carboxamide | $^1$H-NMR (500 MHz CDCl$_3$): δ 9.18 (d, J = 1.8 Hz, 1H), 8.64 (dd, J = 4.9, 1.8 Hz, 1H), 8.31 (dt, J = 7.9, 1.8 Hz, 1H), 7.95 (d, J = 8.4 Hz, 1H), 7.69 (d, J = 8.4 Hz, 1H), 7.45 (t, J = 3.2 Hz, 3H), 7.37 (dd, J = 7.9, 4.9 Hz, 1H), 7.32 (m, 2H), 6.35 (brs, 2H), 3.80 (t, J = 7.7 Hz, 2H), 1.69 (tq, J = 7.7, 7.7 Hz, 2H), 0.97 (t, J = 7.7 Hz, 3H), EI-MS: 388 (M)$^+$ |
| 11 | | N-n-propyl-3-amino-N-(2,3,4-trifluorophenyl)-6-(3-pyridinyl)thieno[2,3-b]pyridine-2-carboxamide | 1H NMR (500 MHz, CDCl$_3$) δ 9.19 (d, J = 1.8 Hz, 1H), 8.59 (dd, J = 4.8, 1.6 Hz, 1H), 8.37-8.32 (m, 1H), 7.98 (d, J = 8.4 Hz, 1H), 7.72 (d, J = 8.4 Hz, 1H), 7.41-7.37 (m, 2H), 7.13-7.05 (m, 2H), 6.42 (s, 2H), 3.81-3.69 (m, 2H), 1.71-1.62 (m, 2H), 0.96 (t, J = 7.4 Hz, 3H). |
| 12 | | N-allyl-3-amino-N-(4-iodophenyl)-6-(3-pyridinyl)thieno[2,3-b]pyridine-2-carboxamide | $^1$H NMR (500 MHz, CDCl$_3$) δ 9.19 (d, J = 1.8 Hz, 1H), 8.65 (dd, J = 4.7, 1.4 Hz, 1H), 8.37-8.34 (m, 1H), 7.97 (d, J = 8.4, 1H), 7.74 (d, J = 8.5 Hz, 2H), 7.71 (d, J = 8.5 Hz, 1H), 7.38 (dd, J = 7.7, 4.8 Hz, 1H), 7.05 (d, J = 8.5 Hz, 2H), 6.38 (s, 2H), 5.98 (ddt, J = 17.5, 9.6, 6.1 Hz, 1H), 5.20-5.14 (m, 2H), 4.41 (d, J = 6.1 Hz, 2H). |

TABLE 2-continued

| Example | Structural formula | Compound name | Mass spectrometry and NMR |
|---|---|---|---|
| 13 | 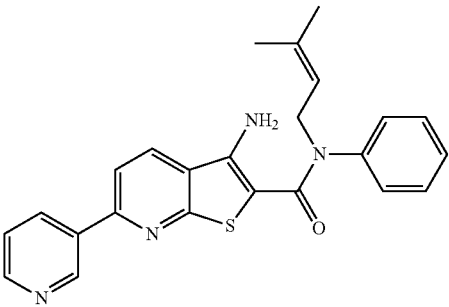 [SMILES: CC(C)=CCN(C(=O)c1sc2nc(-c3cccnc3)ccc2c1N)c1ccccc1] | N-(3-methyl-2-butenyl)-3-amino-N-phenyl-6-(3-pyridinyl)thieno[2,3-b]pyridine-2-carboxamide | $^1$H NMR (500 MHz, CDCl$_3$) δ 9.17 (d, J = 1.5 Hz, 1H), 8.64-8.62 (m, 1H), 8.32-8.30 (m, 1H), 8.95 (d, J = 8.4 Hz, 1H), 7.67 (d, J = 8.4 Hz, 1H), 7.43-7.41 (m, 3H), 7.38-7.35 (m, 1H), 7.29-7.26 (m, 2H), 6.37 (s, 2H), 5.41-5.38 (m, 1H), 4.44 (d, J = 7.0 Hz, 2H), 1.71 (s, 3H), 1.46 (s, 3H). |
| 14 | 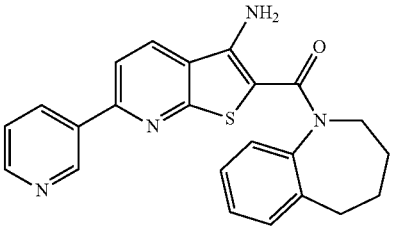 [SMILES: Nc1c(C(=O)N2CCCCc3ccccc32)sc2nc(-c3cccnc3)ccc12] | [3-amino-6-(3-pyridinyl)thieno[2,3-b]2-pyridinyl](2,3,4,5-tetrahydro-1H-benzo[b]azepin-1-yl)methanone | $^1$H-NMR (500 MHz, DMSO-d$_6$) δ: 9.23 (d, J = 1.8 Hz, 1H), 8.61 (d, J = 4.6 Hz, 1H), 8.56 (d, J = 7.4 Hz, 1H), 8.42 (m, 1H), 8.04 (d, J = 8.6 Hz, 1H), 7.52 (brs, 2H), 7.49-7.45 (m, 1H), 7.42-7.38 (m, 1H), 7.37-7.32 (m, 1H), 7.24-7.20 (m, 1H), 7.18-7.16 (m, 1H), 4.93-4.75 (m, 1H), 2.84-2.77 (m, 2H), 2.76-2.56 (m, 1H), 2.02-1.85 (m, 1H), 1.85-1.71 (m, 2H), 1.45-1.28 (m, 1H); $^{13}$C-NMR (DMSO-d$_6$) δ: 164.0, 160.1, 154.1, 150.2, 147.9, 147.9, 142.1, 141.6, 134.2, 133.3, 131.6, 130.0, 129.4, 128.7, 127.3, 124.0, 123.7, 116.1, 96.5, 46.8, 33.6, 29.2, 25.7; MS (ESI) m/z 401 [M + H]$^+$; Anal. Calcd for C$_{23}$H$_{20}$N$_1$O$_2$S•H$_2$O; C: 66.01, H: 5.30, N: 13.39: Found; C: 65.91, H: 5.25, N: 13.23. |

TABLE 3

| Example | Structural formula | Compound name | Mass spectrometry and NMR |
|---|---|---|---|
| 15 | 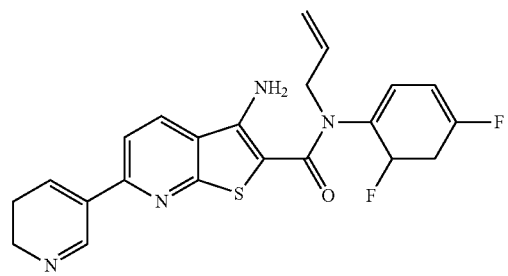 | N-allyl-3-amino-N-(2,4-difluorophenyl)-6-(3-pyridinyl)thieno[2,3-b]pyridine-2-carboxamide | MS (ESI) m/z 423 [(M + 1)$^+$]; 1H NMR (300 MHz, CDCl$_3$) δ: 9.18 (s, 1 H), 8.64 (s, 1 H), 8.34 (d, 1 H, J = 7.5 Hz), 7.98 (d, 1 H, J = 8.1 Hz), 7.71 (d, 1 H, J = 8.1 Hz), 7.41-7.26 (m, 2 H), 6.95 (s, 2 H), 6.45 (s, 2 H), 6.02-5.93 (m, 1 H), 5.18-5.11 (m, 2 H), 4.39 (s, 2 H). |
| 16 | 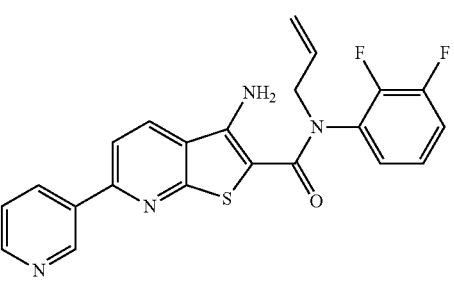 [SMILES: C=CCN(C(=O)c1sc2nc(-c3cccnc3)ccc2c1N)c1cccc(F)c1F] | N-allyl-3-amino-N-(2,3-difluorophenyl)-6-(3-pyridinyl)thieno[2,3-b]pyridine-2-carboxamide | MS (ESI) m/z 423 [(M + 1)$^+$]; $^1$H NMR (300 MHz, CDCl$_3$) δ: 8.63 (d, 2 H, J = 4.2 Hz), 8.02 (d, 1 H, J = 8.1 Hz), 7.96 (s, 1 H), 7.81 (d, 2 H, J = 4.2 Hz), 7.63 (d, 1 H, J = 8.1 Hz), 7.25-7.09 (m, 2H), 6.63 (s, 2 H), 5.97-5.89 (m, 1 H), 5.13-5.08 (m, 2 H), 4.38 (d, 2 H, J = 4.2 Hz). |
| 17 | 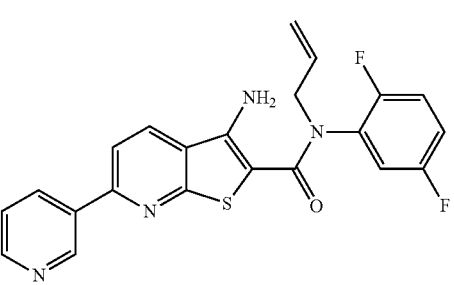 [SMILES: C=CCN(C(=O)c1sc2nc(-c3cccnc3)ccc2c1N)c1cc(F)ccc1F] | N-allyl-3-amino-N-(2,5-difluorophenyl)-6-(3-pyridinyl)thieno[2,3-b]pyridine-2-carboxamide | MS (ESI) m/z 423 [(M + 1)$^+$]; $^1$H NMR (300 MHz, CDCl$_3$) δ: 9.16 (s, 1 H), 8.63 (d, 1 H, J = 3.0 Hz), 8.29 (d, 1 H, J = 7.8 Hz), 8.01 (d, 1 H, J = 8.7 Hz), 7.65 (d, 1 H, J = 8.1 Hz), 7.38-7.34 (m, 1 H), 7.15-7.06 (m, 3 H), 6.59 (s, 2 H), 6.04-5.91 (m, 1 H), 5.19-5.13 (m, 2 H), 4.40 (s, 2 H). |

TABLE 3-continued

| Example | Structural formula | Compound name | Mass spectrometry and NMR |
|---|---|---|---|
| 18 | | N-allyl-3-amino-N-(5-fluoro-2-methylphenyl)-6-(3-pyridinyl)thieno[2,3-b]pyridine-9-carboxamide | MS (ESI) m/z 419 [(M +1)$^+$]; $^1$H NMR (300 MHz, CDCl$_3$) δ: 9.17 (s, 1 H), 8.63 (d, 1 H, J = 3.3 Hz), 8.30 (d, 1 H, J = 7.8 Hz), 8.01 (d, 1 H, J = 8.4 Hz), 7.65 (d, 1 H, J = 8.4 Hz), 7.38-7.34 (m, 1 H), 7.29-7.24 (m, 1 H), 7.12-7.07 (m, 1 H), 6.98-6.95 (m, 1 H), 6.64 (s, 2 H), 6.07-5.96 (m, 1 H), 5.29-5.13 (m, 2 H), 4.78-4.73 (m, 1 H), 3.96-3.89 (m, 1 H), 2.22 (s, 3 H). |
| 19 | | N-allyl-3-amino-N-(3,4-difluorophenyl)-6-(4-pyridinyl)thieno[2,3-b]pyridine-2-carboxamide | MS (ESI) m/z 423 [(M + 1)$^+$]; $^1$H NMR (300 MHz, CDCl$_3$) δ: 8.74 (d, 2 H, J = 4.2 Hz), 8.19 (d, 1 H, J = 8.4 Hz), 8.07 (s, 1 H), 7.93 (d, 2 H, J = 4.8 Hz), 7.72 (d, 1 H, J = 8.1 Hz), 7.33-7.13 (m, 2 H), 6.88 (s, 2 H), 6.07-5.96 (m, 1H), 5.27-5.19 (m, 2 H), 4.47-4.45 (m, 2 H). |
| 20 | | N-allyl-3-amino-N-(3,5-difluorophenyl)-6-(3-pyridinyl)thieno[2,3-b]pyridine-2-carboxamide | MS (ESI) m/z 423 [(M +1)$^+$]; $^1$H NMR (300 MHz, CDCl$_3$) δ: 9.19 (s, 1 H), 8.65 (d, 1 H, J = 3.3 Hz), 8.34 (d, 1 H, J = 7.8 Hz), 8.03 (d, 1 H, J = 8.1 Hz), 7.71 (d, 1 H, J = 8.4 Hz), 7.41-7.37 (m, 1 H), 6.87-6.85 (m, 3 H), 6.51 (s, 2 H), 6.04-5.91 (m, 1 H), 5.23-5.17 (m, 2 H), 4.43 (d, 2 H, J = 5.7 Hz). |
| 21 | | N-allyl-3-amino-N-(3-(pentafluoro-λ$^6$-sulfanyl)phenyl)-6-(3-pyridinyl)thieno[2,3-b]pyridine-2-carboxamide | MS (ESI) m/z 513 [(M + 1)$^+$]; $^1$H NMR (300 MHz, CDCl$_3$) δ: 9.15 (s, 1 H), 8.62 (d, 1 H, J = 3.0 Hz), 8.30 (d, 1 H, J = 7.8 Hz), 8.12 (d, 1 H, J = 8.4 Hz), 7.80 (d, 1 H, J = 8.1 Hz), 7.73 (s, 1 H), 7.65 (d, 1 H, J = 8.4 Hz), 7.55-7.34 (m, 3 H), 6.81 (s, 2 H), 6.06-5.93 (m, 1 H), 5.22-5.14 (m, 2 H), 4.43 (d, 2 H, J = 5.7 Hz). |

TABLE 4

| Example | Structural formula | Compound name | Mass spectrometry and NMR |
|---|---|---|---|
| 22 | | N-allyl-3-amino-N-(3,5-difluorophenyl)-6-(4-pyridinyl)thieno[2,3-b]pyridine-2-carboxamide | MS (ESI) m/z 423 [(M + 1)$^+$]; $^1$H NMR (300 MHz, CDCl$_3$) δ: 8.70 (d, 2 H, J = 5.4 Hz), 8.04 (d, 1 H, J = 8.4 Hz), 7.88 (d, 2 H, J = 5.4 Hz), 7.71 (d, 1 H, J = 8.4 Hz), 6.87-6.85 (m, 3 H), 6.56 (s, 2H), 6.01-5.92 (m, 1 H), 5.23-5.17 (m, 2 H), 4.43 (d, 2 H, J = 5.4 Hz). |

TABLE 4-continued

| Example | Structural formula | Compound name | Mass spectrometry and NMR |
|---|---|---|---|
| 23 | | N-allyl-3-amino-N-(3-(pentafluoro-λ⁶-sulfanyl)phenyl)-6-(4-pyridinyl)thieno[2,3-b]pyridine-2-carboxamide | MS (ESI) m/z 513 [(M + 1)⁺]; ¹H NMR (300 MHz, CDCl₃) δ: 8.65 (s, 2 H), 8.07 (d, 1 H, J = 8.4 Hz), 7.97 (s, 2 H), 7.86 (d, 1 H, J = 4.5 Hz), 7.78 (d, 1 H, J = 7.8 Hz), 7.69 (d, 1 H, J = 8.4 Hz), 7.53-7.41 (m, 2 H), 6.63 (s, 2 H), 6.09-5.94 (m, 1 H), 5.20-5.11 (m, 2 H), 4.43-4.41 (m, 2 H). |
| 24 | | 3-amino-N-(1-naphthyl)-N-phenyl-6-(3-pyridinyl)thieno[2,3-b]pyridine-2-carboxamide | ¹H NMR (500 MHz, DMSO-d₆): δ = 7.37 (br s, 2H, NH₂), 7.55-7.61 (m, 5H, Ar), 7.87-7.90 (m, 1H, Ar), 7.95-8.00 (m, 2H, Ar), 8.19 (d, J = 8.5 Hz, 1H, Ar), 8.57 (d, J = 8.0 Hz, 1H, Ar), 8.63 (J = 8.5 Hz, 1H, Ar), 8.67-8.72 (m, 1H, Ar), 9.39 (s, 1H, NH), 9.78 (s, 1H, Ar) ppm; MS (ESI) m/z 430 [M + Na]⁺, 397 [M + H]. |
| 25 | | 3-amino-N-(2,6-dimethylphenyl)-6-(3-pyridinyl)thieno[2,3-b]pyridine-2-carboxamide | ¹H-NMR (500 MHz, DMSO-d₆) δ: 9.37 (s, 1H), 9.06 (s, 1H), 8.68 (d, J = 4.2 Hz, 1H), 8.60 (d, J = 8.5 Hz, 1H), 8.56 (d, J = 7.7 Hz, 1H), 8.17 (d, J = 8.4 Hz, 1H), 7.57 (dd, J = 5.7, 5.7 Hz, 1H), 7.28 (brs, 2H), 7.13 (s, 3H), 2.21 (s, 6H); ¹³C-NMR (DMSO-d₆) δ: 163.6, 159.0, 154.2, 150.3, 148.1, 145.9, 136.0, 135.3, 134.3, 133.4, 131.9, 127.6, 126.6, 125.6, 123.9, 116.5, 97.2, 18.1; MS (FAB⁺): 375 [M + H]⁺; Anal. Calcd for C₂₁H₁₈N₄OS•1/2H₂O; C: 65.77, H: 4.99, N: 14.61: Found; C: 65.57, H: 5.36, N: 14.51. |
| 26 | | 3-amino-N-[4-(benzyloxy)phenyl]-6-(3-pyridinyl)thieno[2,3-b]pyridine-2-carboxamide | ¹H-NMR (500 MHz, DMSO-d₆) δ: 9.40 (s, 1H), 9.36 (s, 1H), 8.69 (d, J = 3.9 Hz, 1H), 8.61 (d, J = 8.5 Hz, 1H), 8.55 (d, J = 8.0 Hz, 1H), 8.17 (d, J = 8.5 Hz, 1H), 7.61-7.55 (m, 3H), 7.48-7.44 (m, 2H), 7.42-7.32 (m, 5H), 7.00 (d, J = 8.5 Hz, 2H), 5.10 (s, 2H); ¹³C-NMR (DMSO-d₆) δ: 163.6, 159.0, 154.6, 154.4, 150.4, 148.1, 146.3, 137.2, 134.4, 133.4, 132.0, 132.0, 128.4, 127.8, 127.7, 125.5, 123.9, 123.0, 116.6, 114.6, 97.3, 69.3; MS (FAB⁺): 459 [M + H]⁺; Anal. Calcd for C₂₆H₂₀N₄O₂S•H₂O; C: 66.37, H: 4.71, N: 11.91: Found; C: 66.59, H: 4.84, N: 12.04. |
| 27 | | 3-amino-N-(4-iodophenyl)-6-(3-pyridinyl)thieno[2,3-b]pyridine-2-carboxamide | ¹H-NMR (500 MHz, CDCl₃) δ 9.58 (s, 1H), 9.36 (s, Jw = 1.8 Hz, 1H), 8.69 (d, J = 4.7 Hz, Jw = 1.8 Hz, 1H), 8.64 (d, J = 8.5 Hz, 1H), 8.55 (d, J = 8.0 Hz, Jw = 1.8), 8.18 (d, J = 8.5 Hz, 1H), 7.67 (d, J = 8.7 Hz, 2H), 7.57 (m, 3H), 7.47 (s, 1H) EI-MS 472 [M]⁺ (69.2%), 254 [M]⁺ (100%) IR (KBr) 1645 cm⁻¹ C═O伸縮, 1519 cm⁻¹ N—H変角, 1313 cm⁻¹ C—N伸縮 |
| 28 | | 3-amino-N-(2-iodo-4-pyridinyl)-6-(3-pyridinyl)thieno[2,3-b]pyridine-2-carboxamide | MS (ESI) m/z 474 [(M + H)⁺] ¹H-NMR (500 MHz, DMSO-d₆) δ: 9.38 (d, J = 2.1 Hz, 1H), 8.90 (s, 1H), 8.76 (brs, 1H), 8.70 (m, 2H), 8.56 (dt, J = 8.0, 1.9 Hz, 1H), 8.46 (d, J = 5.3 Hz, 1H), 8.22 (d, J = 8.5 Hz, 1H), 7.98 (d, J = 5.3 Hz, 1H), 7.58 (m, 3H). |

TABLE 5

| Example | Structural formula | Compound name | Mass spectrometry and NMR |
|---|---|---|---|
| 29 | | 3-amino-6-(3-pyridinyl)-N-(4-(trifluoromethyl)phenyl)thieno[2,3-b]pyridine-2-carboxamide | MS (ESI) m/z 415 [(M + 1)+]: $^1$H NMR (500 MHz, DMSO-d$_6$, 300 MHz) δ: 9.83 (s, 1 H), 9.39 (s, 1 H), 8.71-8.58 (m, 2 H), 8.58 (d, 1 H, J = 8.1 Hz), 8.21 (d, 1 H, J = 8.7 Hz), 7.96 (d, 2 H, J = 8.4 Hz), 7.71 (d, 2 H, J = 8.4 Hz), 7.58-7.34 (m, 3 H). |
| 30 | | 3-amino-N-(3',5'-bis(trifluoromethyl)[1,1'-biphenyl]-4-yl)-6-(3-pyridinyl)thieno[2,3-b]pyridine-2-carboxamide | MS (ESI) m/z 559 [(M + 1)+]; $^1$H NMR (300 MHz, DMSO-d$_6$) δ: 9.69 (s, 1H), 9.37 (s, 1 H), 8.68-8.64 (m, 2 H), 8.55 (d, 1 H, J = 7.8 Hz), 8.34 (s, 2 H), 8.19 (d, 1 H, J = 8.4 Hz), 8.04 (s, 1 H), 7.91-7.90 (m, 4 H), 7.58-7.53 (m, 3 H). |
| 31 | | 3-amino-6-(4-pyridinyl)-N-(3-(trifluoromethyl)phenyl)thieno[2,3-b]pyridine-2-carboxamide | MS (ESI) m/z 415 [(M + 1)+]; 1H NMR (300 MHz, DMSO-d$_6$) δ: 9.83 (s, 1 H), 9.39 (s, 1 H), 8.71-8.58 (m, 2 H), 8.58 (d, 1 H, J = 8.1 Hz), 8.21 (d, 1 H, J = 8.7 Hz), 7.96 (d, 2 H, J = 8.4 Hz), 7.71 (d, 2 H, J = 8.4 Hz), 7.58-7.34 (m, 3 H). |
| 32 | | 3-amino-N-(4-pyridinyl)-6-(4-pyridinyl)thieno[2,3-b]pyridine-2-carboxamide | MS (ESI) m/z 348 [(M + H)+] $^1$H NMR (500 MHz, DMSO-d$_6$) δ: 9.87 (s, 1H), 8.76 (d, J = 6.0 Hz, 2H), 8.72 (d, J = 8.5 Hz, 1H), 8.44 (d, J = 6.1 Hz, 2H), 8.25 (d, J = 8.5 Hz, 1H), 8.16 (d, J = 6.0 Hz, 2H), 7.77 (d, J = 6.1 Hz, 2H), 7.63 (s, 2H) |
| 33 | | 3-amino-N-(4-pyridinyl)-6-(5-pyrimidinyl)thieno[2,3-b]pyridine-2-carboxamide | MS (ESI) m/z 349 [(M + H)+] $^1$H-NMR (500 MHz, DMSO-d$_6$) δ: 9.86 (s, 1H), 9.55 (s, 2H), 9.30 (s, 1H), 8.73 (d, J = 8.5 Hz, 1H), 8.44 (d, J = 6.4 Hz, 2H), 8.27 (d, J = 8.5 Hz, 1H), 7.77 (d, J = 6.4 Hz, 2H), 7.63 (s, 2H) |

TABLE 6

| Example | Structural formula | Compound name | Mass spectrometry and NMR |
|---|---|---|---|
| 34 | | 3-amino-N-(4-fluorophenyl)-N-(2-methylprop-2-en-1-yl)-6-(3-pyridinyl)thieno[2,3-b]pyridine-2-carboxamide | MS (ESI, m/z) 419 [(M + H)+]; 1H NMR (300 MHz, CDCl3) δ 9.18 (s, 1H), 8.64 (d, J = 2.3 Hz, 1H), 8.33 (d, J = 7.8 Hz, 1H), 7.98 (d, J = 8.3 Hz, 1H), 7.69 (d, J = 8.3 Hz, 1H), 7.12-7.34 (m, 1H), 7.34-7.25 (m, 2H), 7.16-7.06 (m, 2H), 6.45 (brs, 2H), 4.92 (s, 1H), 4.85 (s, 1H), 4.40 (s, 2H), 1.84 (s, 3H). |

TABLE 6-continued

| Example | Structural formula | Compound name | Mass spectrometry and NMR |
|---|---|---|---|
| 35 | | 3-amino-N-(4-(fluorophenyl)-N-(prop-2-yn-1-yl)-6-(3-pyridinyl)thieno[2,3-b]pyridine-2-carboxamide | MS (ESI, m/z) 403 [(M + H)+]; 1H NMR (300 MHz, CDCl3/CD3OD) δ 9.14-9.13 (m, 1H), 8.58 (dd, J = 2.6, 1.2 Hz, 1H), 8.38 (d, J = 7.6 Hz, 1H), 8.17 (d, J = 8.4 Hz, 1H), 7.73 (d, J = 8.3 Hz, 1H), 7.51-7.39 (m, 3H), 7.27-7.11 (m, 2H), 4.57 (s, 2H), 2.36 (s, 1H). |
| 36 | | 3-amino-N-phenyl-N-((Z)-4-(prop-2-yloxy)but-2-enyl)-6-(3-pyridinyl)thieno[2,3-b]pyridine-2-carboxamide | MS (ESI): m/z (%): 455 (100) [(M + H)+]; 1H NMR (500 MHz, CDCl3): δ 2.39 (t, J = 2.4 Hz, 1 H, CH), 3.98 (d, J = 2.3 Hz, 2 H, CH2), 3.99 (d, J = 8.6 Hz, 2 H, CH2), 4.53 (d, J = 7.0 Hz, 2 H, CH2), 5.70 (tdd, J = 11.0, 6.6, 1.3 Hz, 1 H, CH), 5.85 (tdd, J = 11.0, 7.1, 1.3 Hz, 1 H, CH), 6.41 (bs, 2 H, NH2), 7.25-7.48 (m, 6 H, ArH), 7.66 (dd, J = 8.9, 4.1 Hz, 1 H, ArH), 7.96 (d, J = 7.1 Hz, 1 H, ArH), 8.28-8.35 (m, 1 H, ArH), 8.63 (bs, 1 H, ArH), 9.17 (bs, 1 H, ArH). |
| 37 | | 3-amino-N-benzyl-N-phenyl-6-(3-pyridinyl)thieno[2,3-b]pyridine-2-carboxamide | MS (ESI, m/z) 459.13 [(M + Na)+], 437.15 [(M + 1)+] 1H NMR (500 MHz, CDCl3) δ 9.18 (s, 1H), 8.64 (d, J = 4.8 Hz, 1H), 8.31 (d, J = 8.1 Hz, 1H), 7.97 (d, J = 8.5 Hz, 1H), 7.69 (d, J = 8.5 Hz, 1H), 7.26-7.40 (m, 8H), 7.18 (d, J = 8.0 Hz, 2H), 6.42 (s, 1H), 5.07 (s, 2H). |
| 38 | | 3-amino-N-((E)-4-(pent-4-ynyloxy)but-2-enyl)-N-phenyl--6-(3-pyridinyl)thieno[2,3-b]pyridine-2-carboxamide | MS (ESI): m/z: (%): 505 (100) (M+ + Na]. 1H NMR (500 MHz, CDCl3) δ 9.22 (s, 1 H, ArH), 8.65 (d, J = 4.0 Hz, 1 H, ArH), 8.44 (d, J = 8.1 Hz, 1 H, ArH), 7.98 (d, J = 8.4 Hz, 1 H, ArH), 7.70 (d, J = 8.4 Hz, 1 H, ArH), 7.39-7.49 (m, 4 H, ArH), 7.29-7.31 (m, 2 H, ArH), 6.39 (bs, 2 H, NH2), 5.90 (dt, J = 15.4, 6.4 Hz, 1H, CH), 5.67 (dt, J = 15.5, 5.8 Hz, 1 H, CH), 4.46 (d, J = 6.2 Hz, 2 H, CH2), 3.96 (d, J = 4.8 Hz, 2 H, CH2), 3.45 (t, J = 6.2 Hz, 2 H, CH2), 2.26 (dt, J = 7.1, 2. Hz, 2 H, CH2), 1.93 (t, J = 2.6 Hz, 1 H, CH), 1.76 (quintet, J = 6.6 Hz, 2 H, CH2). |

TABLE 6-continued

| Example | Structural formula | Compound name | Mass spectrometry and NMR |
|---|---|---|---|
| 39 | | 3-amino-N-prenyl-N-(4-pyridinyl)-6-(3-pyridinyl)thieno[2,3-b]pyridine-2-carboxamide | MS (ESI) m/z 416 [(M + H)+], 438 [(M + Na)+]<br>1H NMR (500 MHz, CDCl3) δ 9.20 (s, 1H), 8.66 (d, J = 4.9 Hz, 1H), 8.63 (d, J = 5.1 Hz, 2H), 8.35 (d, J = 7.9 Hz, 1H), 7.98 (d, J = 8.4 Hz, 1H), 7.73 (d, J = 8.4 Hz, 1H), 7.40 (dd, J = 7.9, 4.9 Hz, 1H), 7.21 (d, J = 5.1 Hz, 2H), 6.32 (s, 2H), 5.33 (t, J = 6.8 Hz, 1H), 4.78 (d, J = 6.8 Hz, 2H), 1.71 (s, 3H). 1.56 (s, 3H). |
| 40 | | 3-amino-N-(2-cyclopentylidene-ethyl)-N-phenyl-6-(3-pyridinyl)thieno[2,3-b]pyridine-2-carboxamide | MS (ESI) m/z 441 [(M + H)+]<br>1H NMR (500 MHz, CDCl3) δ 9.17 (s, 1H), 8.63 (br s, 1H), 8.31 (d, J = 8.0 Hz, 1H), 7.95 (d, J = 8.4 Hz, 1H), 7.67 (d, J = 8.4 Hz, 1H), 7.43-7.40 (m, 3H), 7.37 (dd, J = 8.0, 4.8 Hz, 1H), 7.30 (m, 2H), 6.38 (s, 2H), 5.50 (m, 1H), 4.42 (d, J = 7.1 Hz, 2H), 2.45 (br s, 2H), 1.98 (br s, 2H), 1.55 (m, 4H). |
| 41 | | 3-amino-6-(3-pyridinyl)thieno[2,3-b]2-pyridinyl)(3,4-dihydro-4,4-dimethyl-1(2H)-quinolinyl)methanone | MS (EI), m/z 414 [(M)+]<br>1H NMR (500 MHz, CDCDl3) δ 9.22 (brs, 1H), 8.66 (brs, 1H), 8.31 (d, J = 7.9 Hz, 1H), 7.98 (d, J = 8.4 Hz, 1H), 7.70 (d, J = 8.4 Hz, 1H), 7.38 (d, J = 7.3 Hz, 2H), 7.19-7.14 (m, 2H), 7.05 (t, J = 7.3 Hz, 1H), 6.17 (s, 2H), 3.96 (t, J = 6.7 Hz, 2H), 1.87 (t, J = 6.7 Hz, 2H), 1.40 (s, 6H); 13C NMR (126 MHz, CDCl3) δ 166.93, 161.17, 154.97, 150.27, 148.41, 146.85, 140.35, 136.80, 134.62, 134.23, 129.80, 126.29, 126.17, 125.68, 125.35, 124.53, 123.68, 115.78, 102.73, 42.70, 38.68, 33.71, 28.83. |

TABLE 7

| Example | Structural formula | Compound name | Mass spectrometry and NMR |
|---|---|---|---|
| 42 | | 5-amino-N-phenyl-N-prenyl-2-(pyridin-3-yl)quinoline-6-carboxamide | MS (ESI) m/z 409 [(M + H)+]<br>1H-NMR (CDCl3) δ: 9.30 (s, 1H), 8.68 (s, 1H), 8.45 (d, J = 7.8 Hz, 1H), 8.28 (d, J = 8.6 Hz, 1H), 7.80 (d, J = 8.6 Hz, 1H), 7.42 (t, J = 5.2 Hz, 1H), 7.19-7.05 (m, 7H), 5.69 (s, 2H), 5.41 (t, J = 6.5 Hz, 1H), 4.56 (d, J = 6.5 Hz, 2H), 1.72 (s, 3H), 1.56 (s, 3H). |

TABLE 7-continued

| Example | Structural formula | Compound name | Mass spectrometry and NMR |
|---|---|---|---|
| 43 | | 3-amino-N-(4-tert-butylphenyl)-N-(3-methylbut-2-en-1-yl)-6-(4-pyridinyl)thieno[2,3-b]pyridine-2-carboxamide | MS (EI) m/z 470 [(M)+]<br>1H NMR (500 MHz, CDCl3) δ 8.69 (d, J = 5.0 Hz, 2H), 7.96 (d, J = 8.4 Hz, 1H), 7.86 (d, J = 5.5 Hz, 2H), 7.68 (d, J = 8.4 Hz, 1H), 7.42 (d, J = 8.3 Hz, 2H), 7.19 (d, J = 8.3 Hz, 2H), 6.42 (s, 2H), 5.39 (t, J = 6.6 Hz, 1H), 4.40 (d, J = (6.9 Hz, 2H), 1.71 (s, 3H), 1.46 (s, 3H), 1.39 (s, 9H); 13C NMR (126 MHz, CDCl3) δ 165.97, 161.53, 154.55, 152.29, 150.51, 146.53, 145.91, 138.82, 136.24, 129.60, 129.58, 126.53, 124.84, 121.33, 119.65, 116.01, 102.23, 49.21, 34.91, 31.56, 25.85, 17.83. |
| 44 | | 3-amino-6-(4-pyridinyl)thieno[2,3-b]2-pyridinyl)(3,4-dihydro-4,4-dimethyl-1(2H)-quinolyl)methanone | MS (EI), m/z 414 [(M)+]<br>1H NMR (500 MHz, CDCl3) δ 8.69 (s, 2H), 8.01 (dd, J = 8.4, 2.5 Hz, 1H), 7.88 (d, J = 3.6 Hz, 2H), 7.71 (dd, J = 8.4, 2.4 Hz, 1H), 7.37 (d, J = 7.6 Hz, 1H), 7.20-7.11 (m, 2H), 7.14-7.04 (m, 1H), 6.25 (s, 2H), 4.01-3.90 (m, 2H), 1.89-1.85 (m, 2H), 1.40 (s, 3H), 1.39 (s, 3H); 13C NMR (126 MHz, CDCl3) δ 166.83, 161.13, 154.74, 150.51, 146.60, 145.66, 140.47, 136.78, 129.80, 126.36, 126.23, 125.81, 125.39, 125.32, 121.24, 116.02, 103.53, 42.74, 38.69, 33.77, 28.83. |
| 45 | | 3-amino-N-(3-methoxyphenyl)-N-prenyl-6-(4-pyridinyl)thieno[2,3-b]pyridine-2-carboxamide | MS (EI), m/z 444 [(M)+].<br>1H NMR (500 MHz, CDCl3) δ 8.68 (d, J = 4.5 Hz, 2H), 7.96 (d, J = 8.4 Hz, 1H), 7.85 (d, J = 5.7 Hz, 2H), 7.66 (d, J = 8.4 Hz, 1H), 7.31 (t, J = 8.1 Hz, 1H), 6.97 (dd, J = 8.4, 2.0 Hz, 1H), 6.88 (d, J = 7.8 Hz, 1H), 6.84-6.82 (m, 1H), 6.47 (s, 2H), 5.39 (t, J = 6.9 Hz, 1H), 4.42 (d, J = 7.0 Hz, 2H), 3.80 (s, 3H), 1.71 (s, 3H), 1.50 (s, 3H); 13C NMR (126 MHz, CDCl3) δ 165.84, 161.50, 160.46, 154.59, 150.46, 146.64, 145.86, 142.56, 136.36, 130.26, 129.65, 124.79, 122.50, 121.31, 119.54, 115.99, 115.85, 114.53, 101.99, 55.54, 49.00, 25.84, 17.88. |
| 46 | | 3-amino-N-(4-methoxyphenyl)-N-prenyl-6-(4-pyridinyl)thieno[2,3-b]pyridine-2-carboxamide | MS (EI), m/z 444 [(M)+]<br>1H NMR (500 MHz, CDCl3) δ 8.69 (d, J = 5.5 Hz, 2H), 7.97 (d, J = 8.4 Hz, 1H), 7.87 (d, J = 6.1 Hz, 2H), 7.69 (d, J = 8.4 Hz, 1H), 7.19 (d, J = 8.9 Hz, 2H), 6.93 (d, J = 8.9 Hz, 2H), 6.43 (s, 2H), 5.38 (t, J = 7.7 Hz, 1H), 4.40 (d, J = 7.1 Hz, 2H), 3.88 (s, 3H), 1.71 (s, 3H), 1.47 (s, 3H); 13C NMR (126 MHz, CDCl3) δ 166.00, 161.52, 160.03, 154.66, 150.53, 146.53, 145.96, 136.51, 134.04, 131.51, 129.61, 124.81, 121.38, 119.47, 116.09, 114.78, 101.97, 55.58, 48.99, 25.88, 17.87. |
| 47 | | 3-amino-N-metallyl-N-phenyl-6-(4-pyridinyl)thieno[2,3-b]pyridine-2-carboxamide | MS (EI), m/z 400 [(M)+]<br>1H NMR (500 MHz, CDCl3) δ 8.67 (d, J = 5.3 Hz, 2H), 7.97 (d, J = 8.4 Hz, 1H), 7.83 (d, J = 5.6 Hz, 2H), 7.64 (d, J = 8.4 Hz, 1H), 7.40 (d, J = 2.8 Hz, 3H), 7.31 (t, J = 9.6 Hz, 2H), 6.53 (s, 2H), 4.91 (s, 1H), 4.89 (s, 1H), 4.43 (s, 2H), 1.84 (s, 3H); 13C NMR (126 MHz, CDCl3) δ 166.12, 161.35, 154.58, 150.40, 147.08, 145.67, 141.91, 140.84, 129.75, 129.59, 129.35, 128.72, 124.73, 121.21, 115.95, 112.62, 101.39, 56.62, 20.56. |

EXPERIMENTAL EXAMPLES

[Experiment 1] SOD1-Derlin-1-Binding Inhibitory Effect of the Compound of the Present Invention 1. Methods
1-1. Main Reagents, Antibodies, Etc.

With regard to antibodies used in Western blotting, an anti-Flag body (M2) was purchased from Sigma, an anti-HA antibody (3F10) was purchased from Roche, an anti-at-tubulin antibody was purchased from Harlan, an Anti-rat IgG HRP-linked antibody was purchased from Cell Signaling, and an Anti-mouse IgG HRP-linked antibody was purchased from GE healthcare, respectively.

Anti-Flag M2 affinity gel and 1× Flag peptide were purchased from Sigma.

Centrifugal Filters (Amicon Ultra 10K) were purchased from Millipore.

1-2. Method
Cell Culture

As cells, human embryonic kidney-derived, Human Embryonic Kidney 293A (HEK293A) cells were used. The cells were cultured in High Glucose Dulbecco's modified Eagle's medium (DMEM: 4.5 mg/ml glucose, Sigma) supplemented with complement-inactivated 10% fetal bovine serum (FBS, Vitromex) and 100 units/mL Penicillin G (Meiji), which was placed in an incubator set at conditions of 37° C. and 5% $CO_2$.

Transfection

Transfection into the HEK293A cells was carried out using PEI-Max (Polyscience) at a ratio of 3 μL of PEI-Max to 1 μg of plasmid. DMEM was mixed with PEI-Max, and the mixture was then left at rest for 5 minutes. Thereafter, the reaction mixture was added to the plasmid DNA dissolved in DMEM, and the thus obtained mixture was further left at rest for 15 minutes. After seeding, the culture was carried out for 12 to 24 hours, and the resultant was then added to a culture medium of cells, in which the medium had been exchanged with DMEM supplemented only with 10% FBS.

The transfected plasmids are as follows:
pcDNA3.0-Derlin-1-HA, pcDNA3.0-Flag-SOD1 G93A, and 123 types of other mutants.

The previously reported plasmids were used as plasmids mentioned above (see Nishitoh et al., Genes Dev 22, 1451-1464, (2008): Fujisawa et al., Ann Neurol 72, 739-749, (2012)).

Cell Lysis

In the lysis of HEK293A cells for use in a co-immunoprecipitation experiment, an IP lysis buffer (20 mM Tris-HCl (pH 7.5), 150 mM NaCl, 10 mM EDTA (pH 8.0), 1% Triton-X 100, 5 μg/mL leupeptin, and 1 mM phenylmethylsulfonyl fluoride) was used.

Cell-Based Co-Immunoprecipitation Assay

After the transfection on a 24-well plate, the cells were cultured for 12 hours or 24 hours, and the obtained cell culture was exchanged with 200 μL of medium. Thereafter, 1% DMSO or various types of compounds having each different concentration were added into the culture. Thirty-six hours or twenty-four hours later, the cells were incubated in the IP lysis buffer (300 μL/well) at 4° C. for 25 minutes, so that the cells were lysed. The cell lysate was centrifuged at 4° C. at 15000 rpm for 10 minutes, and a supernatant was then recovered. To this supernatant, Anti-Flag M2 affinity gel was added in a liquid amount of 20 μL, and they were allowed to react with each other by subjecting the obtained mixture to inversion mixing at 4° C. for 25 minutes. After completion of the reaction, a supernatant was removed, and the residue was washed twice with High salt wash buffer (1% Triton X 100, 500 mM NaCl, 20 mM Tris-HCl (pH 7.5), and 5 mM EGTA), and was then washed once with Low salt wash buffer (150 mM NaCl, 20 mM Tris-HCl (pH 7.5), and 5 mM EGTA). Finally, 50 μL of a 2×SDS sample buffer was added to the resultant, and the obtained mixture was then boiled at 98° C. for 3 minutes to obtain an SDS-PAGE sample. Regarding the lysate, a 2×SDS sample buffer was added in an amount equal to the supernatant, and the obtained mixture was then boiled at 98° C. for 3 minutes to obtain an SDS-PAGE sample.

Western Blotting Analysis

After completion of SDS-PAGE, a protein was transferred from the gel into a polyvinylidene difluoride membrane (PVDF) (0.2 m, Pall), and was then blocked with TBS-T (150 mM NaCl, 50 mM Tris-HCl (pH 8.0), and 0.05% Tween 20) supplemented with 5% skimmed milk at room temperature for 2 hours or more. Thereafter, a primary antibody diluted with TBS-T supplemented with 5% bovine serum albumin and 0.1% $NaN_3$ was allowed to bind to each molecule on the PVDF membrane at 4° C. for 12 hours or more. After completion of the reaction, a secondary antibody (HRP-linked 2nd antibody) diluted with TBS-T supplemented with 5% skimmed milk was allowed to bind to the primary antibody at room temperature for 1 hour. Thereafter, the resultant was washed with TBS-T for 15 minutes, 3 or more times, and detection was then carried out using an enhanced chemiluminescence (ECL) system.

Mice

Wild-type mice (C57BL/6) and SOD1 G93A transgenic mice (G1L/+ line, backcrossed to C57BL/6) were purchased from The Jackson Laboratory, and were then mated and/or bred. All assays were carried out using only male mice.

Intracerebroventricular (i.c.v.) Administration

Using Brain infusion kit 3 (Alzet) and an osmotic pump (Model 2006, Alzet), the compound was continuously administered into the cerebral ventricle of the SOD1 G93A transgenic mice (average onset: 28.1+1.3-week-old (Nishitoh et al., Genes Dev 22, 1451-1464, 2008)), from the time at which the mice were 22 weeks old (0.15 μL/h, 6 weeks/pump). As a preparation stage, 50% DMSO/PBS or each compound was filled into the pump, and was then immersed in 0.9% NaCl, so that priming was carried out 37° C. for 60 hours or more. Upon installation of the pump, the mice were anesthetized by intraperitoneal administration of 0.01 μL/g xylazine (1 mg/ml, Sigma) and 0.007 μL/g Pentobarbital Sodium Salt (5.4 mg/ml, Nacalai). The head portion of each mouse was dehaired, and the mouse was then fixed on a stereotaxic instrument equipped with a manipulator (NARISHIGE). Thereafter, the skin was cut, and the skull was exposed. The coordinate of Bregma was set at 0, and the position that was 1.1 mm to the right, 0.5 mm backward, and 2.5 mm downward was set at the coordinate of the administered cerebral ventricle. The pump was arranged under the dorsal skin, a cannula was then fixed using an adhesive, and the skin on the head portion of the mouse was closed using the adhesive. The pump was exchanged with a new one every 6 weeks, until it became difficult to perform surgery due to the onset of the pathologic conditions of ALS. Upon the exchange of the pump, the mouse was anesthetized, using 4% Isoflurane (Wako Pure Chemical Industries, Ltd.) for introduction, and 2% Isoflurane for maintenance. The dorsal surface of the pump-inserted site was dehaired, and the skin was excised to remove the pump. The removed pump was exchanged with a new pump that had previously been filled with 50% DMSO/PBS or each compound. After the exchange of the pump, the excised skin was closed with Wound clip (Alzet).

Behavior Analysis

From the week at which the mice became 25 weeks old, motor function was measured three times a week according to a rotarod test. ROTA-ROD (Muromachi Kikai Co., Ltd.) was set at a reached rotation speed of 40 rpm and an acceleration time of 180 seconds. The period of time required until the target mouse was fallen during 300 seconds at longest was recorded. An interval of 180 seconds was provided between two trials. Two measurements were carried out in each trial, and better results were determined to be the results of the day. An average value in a week was calculated. When the results of the current week were lower than the results of the previous week for two continuous weeks, the age in weeks of the mouse that was two weeks ago (peak) was defined as an onset of the mouse (a period of time required until the onset of the pathologic conditions).

Count Assay of Motor Neurons

A 31-week-old mouse was subjected to perfusion fixation using 4% paraformaldehyde/PBS, and cerebrospinal tissues were then removed from the mouse. The recovered cerebrospinal tissues were immersed in 4% paraformaldehyde/PBS, and were then fixed at 4° C. for 24 hours or more. Thereafter, the cerebrospinal tissues were transferred into 30% sucrose solution/MilliQ, and were then replaced at 4° C. for 24 hours or more. The lumbar cord region was cut, and was stood vertically to Cryomold No. 1 (SAKURA) on dry ice. The lumbar cord region was fixed by filling the Cryomold No. 1 with Cryomount 1 (low viscosity, MUTO PURE CHEMICALS CO., LTD.) to produce a frozen spinal tissue sample. Using CM3050 S Cryostat (Leica) set at −20° C., a 40-μm section was produced. The section was attached onto a gelatin-coated slide grass (MAS coat, MATSUNAMI), and was sufficiently dried. After that, the section was left in 5% acetic acid/95% ethanol at 60° C. overnight. The section was contacted with 95% ethanol, and then with 70% ethanol for 5 minutes each, and was then rinsed with water. Thereafter, the section was immersed in 0.1% Cresyl Violet Acetate (WALDECK; 1A-400)/10% acetic acid/MilliQ, was then heated in a microwave until immediately before boiling, and was then returned to room temperature, so that Nissl staining was carried out. The resulting section was rinsed with water again, and was then immersed in 70% ethanol, and thereafter, separation status was confirmed. The section was immersed in 95% ethanol, and then, in 100% ethanol for 5 minutes each, was then subjected to Xylene (Wako Pure Chemical Industries, Ltd.) dehydration series, and was then sealed with Mount Quick (Daido Sangyo Co., Ltd.). Using 20× objective lens, the stained section was observed under a bright field microscope (Leica). As a result, it could be confirmed that neurons each having a diameter of 20 μm or more are present in the spinal cord anterior horn, and the neurons, in which the staining of the cytoplasm could be confirmed while being distinguished from the nucleus, were counted as motor neurons.

2. Results

Cell-Based Co-Immunoprecipitation Assay

With regard to the compounds of the present invention (Example Compound 1 to Example Compound 47), whether or not the present compound can inhibit the binding between ALS-related mutant SOD1 and Derlin-1 in a cell by being added into a cell culture solution was examined according to a co-immunoprecipitation experiment. In this experimental system, not only whether or not the present compound can dissociate the previously formed mutant SOD1-Derlin-1 complex, but also whether or not the present compound can previously inhibit the binding between mutant SOD1 and Derlin-1, which has been newly synthesized in a cell, can be confirmed.

Cells, in which Flag-SOD1 G93A (ALS-related mutant) and Derlin-1-HA had been allowed to overexpress, were cultured, and the compound of the present invention was then added into the culture solution. After completion of the culture, using an anti-Flag antibody, immunoprecipitation was carried out from the cell lysate. The experimental results obtained using Example Compound 1 (5 μM, 10 μM, and 20 μM) and Example Compound 4 (0.625 μM, 1.25 μM, 2.5 μM, and 5 μM) are shown in FIG. 1. When Example Compound 1 and Example Compound 4 were added, the band of the blotting with the anti-HA antibody with respect to the immunoprecipitate obtained with the anti-Flag antibody became thinner than the second lane, to which the compound was not added (IB:HA). That is, it was demonstrated that when Example Compound 1 and Example Compound 4 were added to the cell culture solution, the binding between mutant SOD1 and Derlin-1 was inhibited, and the amount of Derlin-1, which bound to the mutant SOD1 and was co-precipitated, was reduced.

In the above-described SOD1-Derlin-1-binding inhibition experiment, SOD1 G93A that is a representative mutant SOD1 associated with the onset of the pathologic conditions of ALS was used. According to previous studies, however, it has become clear that 122 types of ALS-related mutant SOD1s bind to Derlin-1 (Fujisawa et al., Ann Neurol 72, 739-749, (2012)). Hence, whether or not Example Compound 1 inhibits the binding between multiple types of these mutant SODs and Derlin-1 was examined at a cell level according to a co-immunoprecipitation experiment. As a result, it was confirmed that Example Compound 1 inhibits the binding between all of the mutant SODs and Derlin-1 (FIG. 2 to FIG. 9). Moreover, it was also confirmed that Example Compound 1 did not exhibit inhibitory activity on dimerization of SOD1 or complex formation by Derlin-1 under conditions for inhibiting the binding between mutant SOD1 and Derlin-1. Accordingly, it was demonstrated that Example Compound 1 does not have inhibitory activity on interaction between non-specific proteins, but has selectivity to the binding between mutant SOD1 and Derlin-1 as a target.

Table 8 to Table 13 show the results of cell-based co-immunoprecipitation assays regarding the Example Compounds 1 to 47 of the present invention. With regard to the activity value (score), a compound exhibiting no inhibitory activity is set at 0, a compound exhibiting inhibitory activity is set at 1, a compound exhibiting significant inhibitory activity is set at 2, and a compound having higher inhibitory activity than the compound of Example 1 is set at 3 (wherein all of Example Compounds 1 to 47 were found to have inhibitory activity).

TABLE 8

| Example | Structural formula | Assay concentration (μM) | Activity value (score) | Effects on model mice |
|---|---|---|---|---|
| 1 | | 20 | 2 | Significant effects |
| 2 | | 20 | 2 | |
| 3 | | 20 | 2 | |
| 4 | | 5 | 2 | |
| 5 | | 10 | 2 | |
| 6 | | 2.6 | 1 | |

TABLE 8-continued

| Example | Structural formula | Assay concentration (μM) | Activity value (score) | Effects on model mice |
|---|---|---|---|---|
| 7 | | 2.6 | 1 | |
| 8 | | 5 | 1 | |

TABLE 9

| Example | Structural formula | Assay concentration (μM) | Activity value (score) | Effects on model mice |
|---|---|---|---|---|
| 9 | | 5 | 1 | |
| 10 | | 20 | 2 | |
| 11 | | 20 | 2 | |

TABLE 9-continued
| Example | Structural formula | Assay concentration (μM) | Activity value (score) | Effects on model mice |
|---|---|---|---|---|
| 12 | 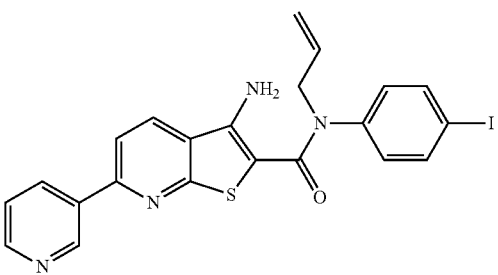 [SMILES: C=CCN(C(=O)c1sc2nc(-c3cccnc3)ccc2c1N)c1ccc(I)cc1] | 20 | 2 | |
| 13 | 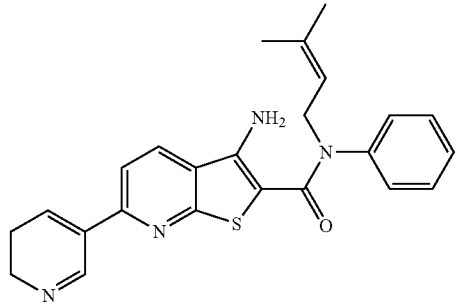 [SMILES: CC(C)=CCN(C(=O)c1sc2nc(C3=CCCN=C3)ccc2c1N)c1ccccc1] | 20 | 2 | |
| 14 | 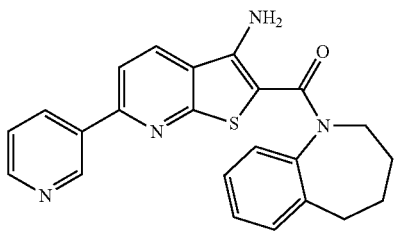 [SMILES: Nc1c(C(=O)N2CCCCc3ccccc32)sc2nc(-c3cccnc3)ccc12] | 20 | 2 | |
| 15 | 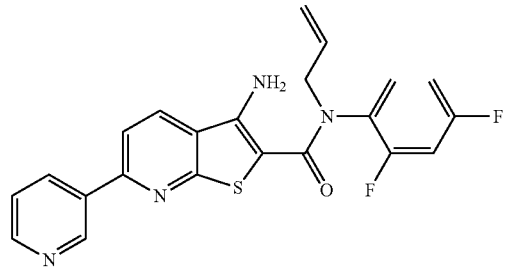 [SMILES: C=CCN(C(=C)/C(F)=C\C(=C)F)C(=O)c1sc2nc(-c3cccnc3)ccc2c1N] | 20 | 2 | |
| 16 | 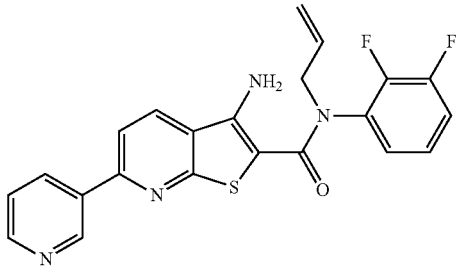 [SMILES: C=CCN(C(=O)c1sc2nc(-c3cccnc3)ccc2c1N)c1cccc(F)c1F] | 20 | 2 | |

TABLE 10

| Example | Structural formula | Assay concentration (μM) | Activity value (score) | Effects on model mice |
|---|---|---|---|---|
| 17 | | 20 | 2 | |
| 18 | | 20 | 2 | |
| 19 | | 20 | 2 | |
| 20 | | 20 | 2 | |
| 21 | | 20 | 2 | |

TABLE 10-continued

| Example | Structural formula | Assay concentration (μM) | Activity value (score) | Effects on model mice |
|---------|-------------------|--------------------------|------------------------|------------------------|
| 22 | (3-amino-6-(pyridin-4-yl)thieno[2,3-b]pyridine-2-carboxamide with N-allyl, N-(3,5-difluorophenyl) substituents) | 20 | 2 | |
| 23 | (3-amino-6-(pyridin-4-yl)thieno[2,3-b]pyridine-2-carboxamide with N-allyl, N-(3-pentafluorosulfanylphenyl) substituents) | 20 | 2 | |
| 24 | (3-amino-6-(pyridin-3-yl)thieno[2,3-b]pyridine-2-carboxamide with N-(naphthalen-1-yl) substituent) | 20 | 1 | |

TABLE 11

| Example | Structural formula | Assay concentration (μM) | Activity value (score) | Effects on model mice |
|---------|-------------------|--------------------------|------------------------|------------------------|
| 25 | (3-amino-6-(pyridin-3-yl)thieno[2,3-b]pyridine-2-carboxamide with N-(2,6-dimethylphenyl) substituent) | 20 | 1 | |
| 26 | (3-amino-6-(pyridin-3-yl)thieno[2,3-b]pyridine-2-carboxamide with N-(4-benzyloxyphenyl) substituent) | 20 | 1 | |

TABLE 11-continued

| Example | Structural formula | Assay concentration (μM) | Activity value (score) | Effects on model mice |
|---|---|---|---|---|
| 27 | | 20 | 1 | |
| 28 | | 20 | 1 | |
| 29 | | 20 | 1 | |
| 30 | | 20 | 1 | |
| 31 | | 20 | 1 | |
| 32 | | 20 | 1 | |
| 33 | | 20 | 1 | |

TABLE 12

| Example | Structural formula | Assay concentration (μM) | Activity value (score) | Effects on model mice |
|---|---|---|---|---|
| 34 | | 20 | 1 | |
| 35 | | 20 | 1 | |
| 36 | | 20 | 1 | |
| 37 | | 20 | 2 | |

TABLE 12-continued

| Example | Structural formula | Assay concentration (μM) | Activity value (score) | Effects on model mice |
|---------|-------------------|--------------------------|------------------------|------------------------|
| 38 | | 20 | 2 | |
| 39 | | 20 | 1 | |
| 40 | | 20 | 1 | |

TABLE 13

| Example | Structural formula | Assay concentration (μM) | Activity value (score) | Effects on model mice |
|---------|-------------------|--------------------------|------------------------|------------------------|
| 41 | | 20 | 3 | |

TABLE 13-continued

| Example | Structural formula | Assay concentration (μM) | Activity value (score) | Effects on model mice |
|---------|--------------------|--------------------------|------------------------|----------------------|
| 42 | | 20 | 1 | |
| 43 | | 20 | 1 | |
| 44 | | 20 | 1 | |
| 45 | | 20 | 1 | |
| 46 | | 20 | 2 | |

TABLE 13-continued

| Example | Structural formula | Assay concentration (μM) | Activity value (score) | Effects on model mice |
|---------|--------------------|---------------------------|-------------------------|-----------------------|
| 47 | 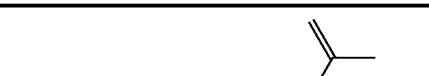 | 20 | 2 | |

Studies Regarding Effect of Improving Pathologic Conditions of ALS Model Mice by Inhibiting Binding of Mutant SOD1 and Derlin-1

Figure 10B:
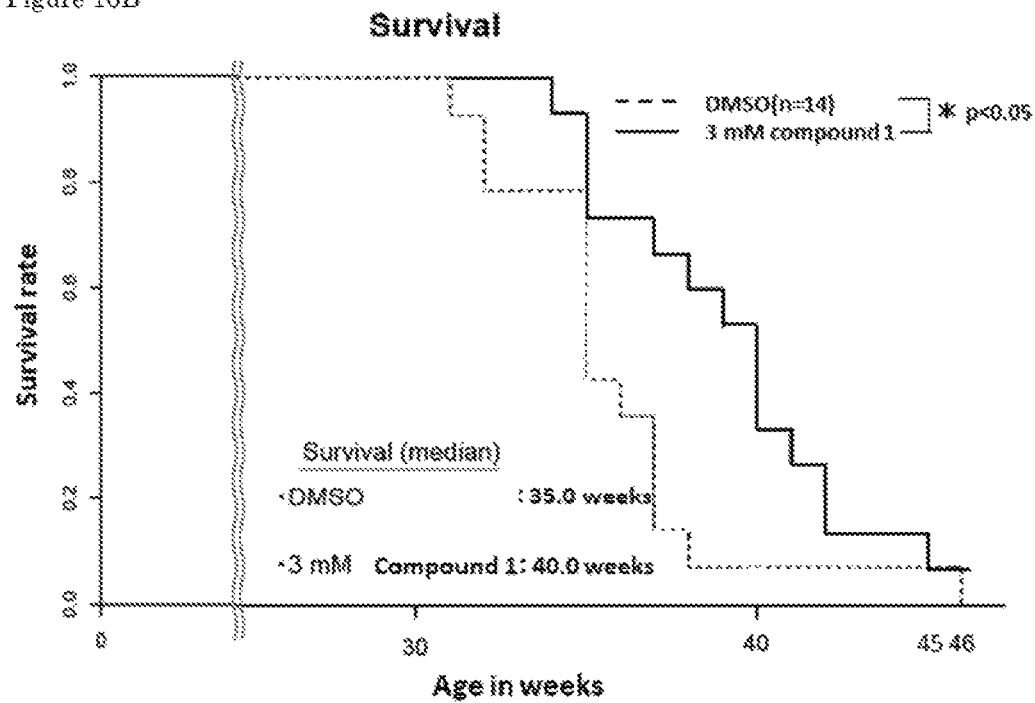

In order to verify the importance of the binding between mutant SOD1 and Derlin-1 on the pathologic conditions of ALS and the possibility of the compound of the present invention as a therapeutic agent, Example Compound 1 was administered to ALS model mice, and its pathologic condition-improving effect was examined. In this case, it is necessary to allow the compound to act on the central nervous system as a target. In general, when a drug is allowed to reach the central nervous system through the blood flow, the permeability of the drug through the blood brain barrier (BBB) is problematic. Thus, in order to eliminate such problem regarding the BBB permeation and to effectively deliver the compound inhibiting the binding between mutant SOD1 and Derlin-1 to the central nervous system, the compound was directly administered into cerebrospinal fluid. In addition, taking into consideration the fact that the pathologic conditions of ALS are tardive and/or progressive, it has been considered that continuous administration of a compound having a constant concentration would lead to effective exhibition of the activity of the compound. Thus, as a method of administering the compound, continuous administration of the compound into mouse cerebral ventricle utilizing an osmotic pump was selected (DeVos and Miller, J Vis Exp, e50326, (2013): Storkebaum et al., Nat Neurosci 8, 85-92, (2005): Haji et al., Exp Neurol 237, 296-303, (2012): Audet et al., PLoS One 7, e34932, (2012)). As ALS model mice, male SOD1 G93A transgenic mice were used, and Example Compound 1 (control: DMSO, 3 mM Compound 1) was continuously administered into the cerebral ventricle of each mouse from the time at which the mice were 22 weeks old before the onset of the pathologic conditions of ALS, so that the influence of the compound on the motor function and survival period of the mice was examined. With regard to a period of time required until the onset of the pathologic conditions (Onset), which was defined from the motor function of the mice according to the rotarod test, the onset was significantly delayed in an Example Compound 1 administration group (FIG. 10A). On the other hand, with regard to survival period (Survival), it became clear that a significant effect of extending the survival period (approximately 14%) was obtained in the Example Compound 1 administration group, as with the Onset (FIG. 10B).

In order to confirm the influence of the compound that inhibits the binding between ALS-related mutant SOD1 and Derlin-1 on motor neuron death in the ALS model mice, motor neurons were detected by Nissl staining in the spinal cord of mice with 31 weeks old, which was the average onset period of a control group (FIG. 11). The number of motor neurons in the Example Compound 1 administration mouse group. As a result, it became clear that the number of motor neurons was significantly high (FIG. 12).

From the aforementioned results, it is considered that the compound of the present invention that inhibits the binding between ALS-related mutant SOD1 and Derlin-1 suppressed motor neuron death in vivo, and exhibited the effect of improving the pathologic conditions of ALS.

INDUSTRIAL APPLICABILITY

The compound according to the present invention has the function of inhibiting the binding between ALS-related mutant SOD1 and Derlin-1, and can be used as a therapeutic agent for ALS, and also, as a lead for the development of further therapeutic agents. Therefore, it is expected that the present compound can be used in the fields of medicine and drug discovery.

The invention claimed is:

1. A compound represented by the following formula (1) or a salt thereof, or a solvate or hydrate thereof:

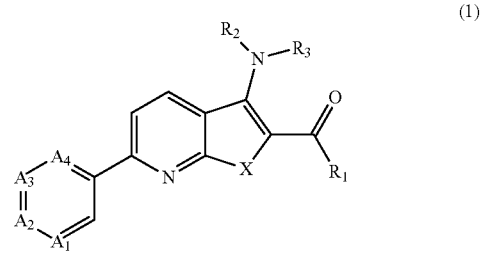

(1)

wherein X represents a sulfur atom or —CH=CH—; $A_1$ to $A_4$ each independently represent a carbon atom or a nitrogen atom, and at least one of $A_1$ to $A_4$ is a nitrogen atom; $R_1$ represents any one of a 1,2,3,4-tetrahydroquinolyl group (or a 3,4-dihydro-1(2H)-quinolyl group), a 3,4-dihydro-4,4-dimethyl-1(2H)-quinolyl group, a 2,3,4,5-tetrahydro-1H-1-benzazepinyl group, or a substituent represented by the following formula (2):

wherein R₄ represents a 2,3,4-trifluorophenyl group, a 4-iodophenyl group, a 2,3-difluorophenyl group, a 3,5-difluorophenyl group, a 5-fluoro-2-methylphenyl group, a 3-pentafluorosulfanylphenyl group, a 2,6-dimethylphenyl group, a 4-benzyloxyphenyl group, a 3,5-bis(trifluoromethyl)biphenyl group, a 4-tert-butylphenyl group, a 3-methoxyphenyl group, an unsubstituted or substituted pyridyl group, or an unsubstituted or substituted naphthyl group; R₅ represents a hydrogen atom, a lower alkyl group, a lower alkenyl group, a lower alkynyl group optionally containing an oxygen atom and/or a double bond, or an unsubstituted or substituted aromatic lower alkyl group; R₂ represents a hydrogen atom, a lower alkyl group, a lower acyl group, or an unsubstituted or substituted aromatic lower alkyl group; and R₃ represents a hydrogen atom, or R₂ and R₃ may bind to each other to form a ring.

2. The compound according to claim 1, which is represented by the following formula (1a), or a salt thereof, or a solvate or hydrate thereof:

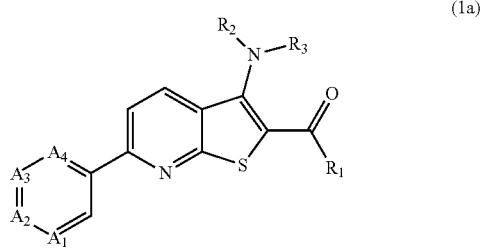

wherein A₁ to A₄ each independently represent a carbon atom or a nitrogen atom, and at least one of A₁ to A₄ is a nitrogen atom; R₁ represents any one of a 1,2,3,4-tetrahydroquinolyl group (or a 3,4-dihydro-1(2H)-quinolyl group), a 3,4-dihydro-4,4-dimethyl-1(2H)-quinolyl group, a 2,3,4,5-tetrahydro-1H-1-benzazepinyl group, or a substituent represented by the following formula (2):

wherein R₄ represents a 2,3,4-trifluorophenyl group, a 4-iodophenyl group, a 2,3-difluorophenyl group, a 3,5-difluorophenyl group, a 5-fluoro-2-methylphenyl group, a 3-pentafluorosulfanylphenyl group, a 2,6-dimethylphenyl group, a 4-benzyloxyphenyl group, a 3,5-bis(trifluoromethyl)biphenyl group, a 4-tert-butylphenyl group, a 3-methoxyphenyl group, an unsubstituted or substituted pyridyl group, or an unsubstituted or substituted naphthyl group; R₅ represents a hydrogen atom, a lower alkyl group, a lower alkenyl group, a lower alkynyl group optionally containing an oxygen atom and/or a double bond, or an unsubstituted or substituted aromatic lower alkyl group; R₂ represents a hydrogen atom, a lower alkyl group, a lower acyl group, or an unsubstituted or substituted aromatic lower alkyl group; and R₃ a hydrogen atom, or R₂ and R₃ may bind to each other to form a ring.

3. The compound according to claim 2, or a salt thereof, or a solvate or hydrate thereof, wherein R₂ and R₃ each represent a hydrogen atom.

4. The compound according to claim 2 or a salt thereof, or a solvate or hydrate thereof, wherein A₁ represents a nitrogen atom, A₂, A₃ and A₄ each represent a carbon atom, and R₁ represents a 2,3,4,5-tetrahydro-1H-1-benzazepinyl group, a 1,2,3,4-tetrahydroquinolyl group (3,4-dihydro-1(2H)-quinolyl group), or a 3,4-dihydro-4,4-dimethyl-1(2H)-quinolyl group.

5. The compound according to claim 2 or a salt thereof, or a solvate or hydrate thereof, wherein A₂ represents a nitrogen atom, A₁, A₃ and A₄ each represent a carbon atom, and R₁ represents a 3,4-dihydro-4,4-dimethyl-1(2H)-quinolyl group.

6. The compound according to claim 2 or a salt thereof, or a solvate or hydrate thereof, wherein A₁ represents a nitrogen atom, A₂, A₃ and A₄ each represent a carbon atom, R4 represents a 4-pyridyl group, a 2-iodo-4-pyridyl group, a 2,3,4-trifluorophenyl group, a 4-iodophenyl group, a 2,3-difluorophenyl group, a 3,5-difluorophenyl group, a 5-fluoro-2-methylphenyl group, a 3-pentafluorosulfanylphenyl group, a 2,6-dimethylphenyl group, a 4-benzyloxyphenyl group, a 4-trifluoromethylphenyl group, a 3,5-bis(trifluoromethyl)biphenyl group, or a 1-naphthyl group, and R₅ represents a hydrogen atom, a 1-propyl group, a 2-butenyl group, a 3-methyl-2-butenyl group, a 2-propenyl group, a 2-methyl-2-propenyl group, a 2-cyclopentylideneethyl group, a 2-propynyl group, a 2-butynyl group, a (Z)-4-(prop-2-yloxy)but-2-enyl group, an (E)-4-(prop-2-yloxy)but-2-enyl group, or a benzyl group.

7. The compound according to claim 2 or a salt thereof, or a solvate or hydrate thereof, wherein A₂ represents a nitrogen atom, A₁, A₃ and A₄ each represent a carbon atom, R₄ represents a 4-pyridyl group, a 3,5-difluorophenyl group, a 3-trifluoromethylphenyl group, a 3-methoxyphenyl group, a 4-tert-butylphenyl group, a 3-pentafluorosulfanylphenyl group, or a 3,5-bis(trifluoromethyl)biphenyl group, and R₅ represents a hydrogen atom, a 2-propenyl group, a 3-methyl-2-butenyl group, or a 2-methyl-2-propenyl group.

8. The compound according to claim 2 or a salt thereof, or a solvate or hydrate thereof, wherein A₄ represents a nitrogen atom, A₁, A₂ and A₃ each represent a carbon atom, R₄ represents a 4-pyridyl group, and R₅ represents a hydrogen atom.

9. The compound according to claim 2 or a salt thereof, or a solvate or hydrate thereof, wherein A₁ and A₃ each represent a nitrogen atom, A₂ and A₄ each represent a carbon atom, R₄ represents a 4-pyridyl group, and R₅ represents a hydrogen atom.

10. The compound according to claim 2 or a salt thereof, or a solvate or hydrate thereof, wherein the compound represented by the formula (1a) is selected from the group consisting of N-allyl-3-amino-N-phenyl-6-(3-pyridinyl)thieno[2,3-b]pyridine-2-carboxamide, N-propargyl-3-amino-N-phenyl-6-(3-pyridinyl)thieno[2,3-b]pyridine-2-carboxamide, (3-amino-6-(3-pyridinyl)thieno[2,3-b]2-pyridinyl)(3,4-dihydro-1(2H)-quinolinyl)methanone, 3-amino-N-(4-pyridinyl)-6-(3-pyridinyl)thieno[2,3-b]pyridine-2-carboxamide, 3-amino-N-(trans-2-butenyl)-N-phenyl-6-(3-pyridinyl)thieno[2,3-b]pyridine-2-carboxamide, 3-amino-N-(4-pyridinyl)-6-(2-pyridinyl)thieno[2,3-b]pyridine-2-carboxamide, 3-amino-N-(4-(3',5'-bis(trifluoromethyl)biphenyl)-6-(4-pyridinyl)thieno[2,3-b]pyridine-2-carboxamide, N-allyl-3-amino-N-(2,5-difluorophenyl)-6-(4-pyridinyl)thieno[2,3-b]pyridine-2-carboxamide, 3-amino-N-(2-butynyl)-N-phenyl-6-(3-pyridinyl)thieno[2,3-b]pyridine-2-carboxamide, N-n-propyl-3-amino-N-phenyl-6-(3-pyridinyl)thieno[2,3-b]pyridine-2-carboxamide, N-n-propyl-3-amino-N-(2,3,4-trifluorophenyl)-6-(3-pyridinyl)thieno[2,3-b]pyridine-2-carboxamide, N-allyl-3-amino-N-(4-iodophenyl)-6-(3-pyridinyl)thieno[2,3-b]pyridine-2-carboxamide, N-(3-methyl-2-butenyl)-3-amino-N-phenyl-6-(3-pyridinyl)thieno[2,3-b]pyridine-2-carboxamide, [3-amino-6-(3-pyridinyl)thieno[2,3-b]2-pyridinyl](2,3,4,5-tetrahydro-1H-benzo[b]azepin-1-yl)methanone, N-allyl-3-amino-N-(2,3-difluorophenyl)-6-(3-pyridinyl)thieno[2,3-b]pyridine-2-carboxamide, N-allyl-3-amino-N-(5-fluoro-2-methylphenyl)-6-(3-pyridinyl)thieno[2,3-b]pyridine-2-carboxamide, N-allyl-3-amino-N-(3,5-difluorophenyl)-6-(3-pyridinyl)thieno[2,3-b]pyridine-2-carboxamide, N-allyl-3-amino-N-(3-(pentafluoro-λ$^6$-sulfanyl)phenyl)-6-(3-pyridinyl)thieno[2,3-b]pyridine-2-carboxamide, N-allyl-3-amino-N-(3,5-difluorophenyl)-6-(4-pyridinyl)thieno[2,3-b]pyridine-2-carboxamide, N-allyl-3-amino-N-(3-(pentafluoro-λ$^6$-sulfanyl)phenyl)-6-(4-pyridinyl)thieno[2,3-b]pyridine-2-carboxamide, 3-amino-N-(1-naphthyl)-N-phenyl-6-(3-pyridinyl)thieno[2,3-b]pyridine-2-carboxamide, 3-amino-N-(2,6-dimethylphenyl)-6-(3-pyridinyl)thieno[2,3-b]pyridine-2-carboxamide, 3-amino-N-[4-(benzyloxy)phenyl]-6-(3-pyridinyl)thieno[2,3-b]pyridine-2-carboxamide, 3-amino-N-(4-iodophenyl)-6-(3-pyridinyl)thieno[2,3-b]pyridine-2-carboxamide, 3-amino-N-(2-iodo-4-pyridinyl)-6-(3-pyridinyl)thieno[2,3-b]pyridine-2-carboxamide, 3-amino-6-(3-pyridinyl)-N-(4-(trifluoromethyl)phenyl)thieno[2,3-b]pyridine-2-carboxamide, 3-amino-N-(3',5'-bis(trifluoromethyl)-[1,1'-biphenyl]-4-yl)-6-(3-pyridinyl)thieno[2,3-b]pyridine-2-carboxamide, 3-amino-N-(4-pyridinyl)-6-(4-pyridinyl)thieno[2,3-b]pyridine-2-carboxamide, 3-amino-N-(4-pyridinyl)-6-(5-pyrimidinyl)thieno[2,3-b]pyridine-2-carboxamide, 3-amino-N-(4-fluorophenyl)-N-(2-methylprop-2-en-1-yl)-6-(3-pyridinyl)thieno[2,3-b]pyridine-2-carboxamide, 3-amino-N-(4-fluorophenyl)-N-(prop-2-yn-1-yl)-6-(3-pyridinyl)thieno[2,3-b]pyridine-2-carboxamide, 3-amino-N-phenyl-N—((Z)-4-(prop-2-yloxy)but-2-enyl)-6-(3-pyridinyl)thieno[2,3-b]pyridine-2-carboxamide, 3-amino-N-benzyl-N-phenyl-6-(3-pyridinyl)thieno[2,3-b]pyridine-2-carboxamide, 3-amino-N-((E)-4-(pent-4-ynyloxy)but-2-enyl)-N-phenyl-6-(3-pyridinyl)thieno[2,3-b]pyridine-2-carboxamide, 3-amino-N-prenyl-N-(4-pyridinyl)-6-(3-pyridinyl)thieno[2,3-b]pyridine-2-carboxamide, 3-amino-N-(2-cyclopentylideneethyl)-N-phenyl-6-(3-pyridinyl)thieno[2,3-b]pyridine-2-carboxamide, 3-amino-6-(3-pyridinyl)thieno[2,3-b]2-pyridinyl)(3,4-dihydro-4,4-dimethyl-1(2H)-quinolinyl)methanone, 3-amino-N-(4-tert-butylphenyl)-N-(3-methylbut-2-en-1-yl)-6-(4-pyridinyl)thieno[2,3-b]pyridine-2-carboxamide, 3-amino-6-(4-pyridinyl)thieno[2,3-b]2-pyridinyl)(3,4-dihydro-4,4-dimethyl-1(2H)-quinolyl)methanone, 3-amino-N-(3-methoxyphenyl)-N-prenyl-6-(4-pyridinyl)thieno[2,3-b]pyridine-2-carboxamide, 3-amino-N-(4-methoxyphenyl)-N-prenyl-6-(4-pyridinyl)thieno[2,3-b]pyridine-2-carboxamide, and 3-amino-N-metallyl-N-phenyl-6-(4-pyridinyl)thieno[2,3-b]pyridine-2-carboxamide.

11. The compound according to claim 1, which is represented by the following formula (1b), or a salt thereof, or a solvate or hydrate thereof:

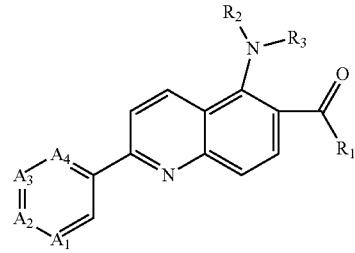

(1b)

wherein $A_1$ to $A_4$ each independently represent a carbon atom or a nitrogen atom, and at least one of $A_1$ to $A_4$ is a nitrogen atom; $R_1$ represents a substituent represented by the following formula (2):

(2)

wherein $R_4$ represents a 2,3,4-trifluorophenyl group, a 4-iodophenyl group, a 2,3-difluorophenyl group, a 3,5-difluorophenyl group, a 5-fluoro-2-methylphenyl group, a 3-pentafluorosulfanylphenyl group, a 2,6-dimethylphenyl group, a 4-benzyloxyphenyl group, a 3,5-bis(trifluoromethyl)biphenyl group, a 4-tert-butylphenyl group, or a 3-methoxyphenyl group; and $R_5$ represents a hydrogen atom, a lower alkyl group, a lower alkenyl group, or a lower alkynyl group; $R_2$ represents a hydrogen atom, a lower alkyl group, a lower acyl group, or an unsubstituted or optionally substituted aromatic lower alkyl group; and $R_3$ represents a hydrogen atom, or $R_2$ and $R_3$ may bind to each other to form a ring.

12. The compound according to claim 11 or a salt thereof, or a solvate or hydrate thereof, wherein $A_1$ represents a nitrogen atom, $A_2$, $A_3$ and $A_4$ each represent a carbon atom, $R_2$ and $R_3$ each represent a hydrogen atom, $R_4$ represents an unsubstituted phenyl group, and $R_5$ represents a 3-methyl-2-butenyl group.

13. The compound according to claim 11 or a salt thereof, or a solvate or hydrate thereof, wherein the compound represented by the formula (1b) is 5-amino-N-phenyl-N-prenyl-2-(pyridin-3-yl)quinoline-6-carboxamide.

14. A compound represented by the following formula (1a) or a salt thereof, or a solvate or hydrate thereof:

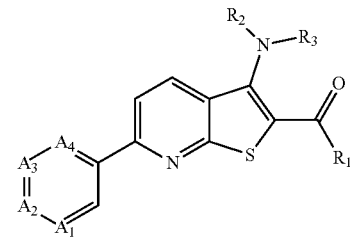

(1a)

wherein $A_1$ represents a nitrogen atom, $A_2$, $A_3$ and $A_4$ each represent a carbon atom, and at least one of $A_1$ to $A_4$ is a nitrogen atom; $R_1$ represents any one of a 1,2,3,4-tetrahydroquinolyl group (or a 3,4-dihydro-1(2H)-quinolyl group), a 3,4-dihydro-4,4-dimethyl-1(2H)-quinolyl group, a 2,3,4,5-tetrahydro-1H-1-benzazepinyl group, or a substituent represented by the following formula (2):

wherein $R_4$ represents a 4-pyridyl group, a 2-iodo-4-pyridyl group, an unsubstituted phenyl group, a 4-fluorophenyl group, a 2,3,4-trifluorophenyl group, a 4-iodophenyl group, a 2,4-difluorophenyl group, a 2,3-difluorophenyl group, a 2,5-difluorophenyl group, a 3,5-difluorophenyl group, a 5-fluoro-2-methylphenyl group, a 3-pentafluorosulfanylphenyl group, a 2,6-dimethylphenyl group, a 4-benzyloxyphenyl group, a 4-trifluoromethylphenyl group, a 3,5-bis(trifluoromethyl)biphenyl group, or a 1-naphthyl group, and $R_5$ represents a hydrogen atom, a 1-propyl group, a 2-butenyl group, a 3-methyl-2-butenyl group, a 2-propenyl group, a 2-methyl-2-propenyl group, a 2-cyclopentylideneethyl group, a 2-propynyl group, a 2-butynyl group, a (Z)-4-(prop-2-yloxy)but-2-enyl group, an (E)-4-(prop-2-yloxy)but-2-enyl group, or a benzyl group; $R_2$ represents a hydrogen atom, a lower alkyl group, a lower acyl group, or an unsubstituted or substituted aromatic lower alkyl group; and $R_3$ a hydrogen atom, or $R_2$ and $R_3$ may bind to each other to form a ring.

15. A compound represented by the following formula (1a) or a salt thereof, or a solvate or hydrate thereof:

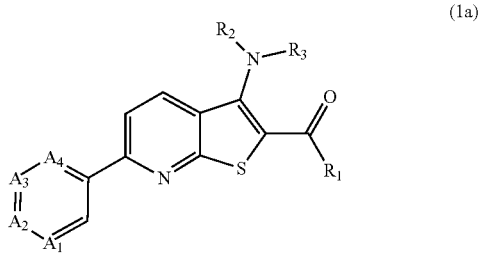

wherein the compound represented by the formula (1a) is selected from the group consisting of N-allyl-3-amino-N-phenyl-6-(3-pyridinyl)thieno[2,3-b]pyridine-2-carboxamide, N-propargyl-3-amino-N-phenyl-6-(3-pyridinyl)thieno[2,3-b]pyridine-2-carboxamide, (3-amino-6-(3-pyridinyl)thieno[2,3-b]2-pyridinyl)(3,4-dihydro-1(2H)-quinolinyl)methanone, 3-amino-N-(4-pyridinyl)-6-(3-pyridinyl)thieno[2,3-b]pyridine-2-carboxamide, 3-amino-N-(trans-2-butenyl)-N-phenyl-6-(3-pyridinyl)thieno[2,3-b]pyridine-2-carboxamide, 3-amino-N-(4-pyridinyl)-6-(2-pyridinyl)thieno[2,3-b]pyridine-2-carboxamide, 3-amino-N-(4-(3',5'-bis(trifluoromethyl)biphenyl)-6-(4-pyridinyl)thieno[2,3-b]pyridine-2-carboxamide, N-allyl-3-amino-N-(2,5-difluorophenyl)-6-(4-pyridinyl)thieno[2,3-b]pyridine-2-carboxamide, 3-amino-N-(2-butynyl)-N-phenyl-6-(3-pyridinyl)thieno[2,3-b]pyridine-2-carboxamide, N-n-propyl-3-amino-N-phenyl-6-(3-pyridinyl)thieno[2,3-b]pyridine-2-carboxamide, N-n-propyl-3-amino-N-(2,3,4-trifluorophenyl)-6-(3-pyridinyl)thieno[2,3-b]pyridine-2-carboxamide, N-allyl-3-amino-N-(4-iodophenyl)-6-(3-pyridinyl)thieno[2,3-b]pyridine-2-carboxamide, N-(3-methyl-2-butenyl)-3-amino-N-phenyl-6-(3-pyridinyl)thieno[2,3-b]pyridine-2-carboxamide, [3-amino-6-(3-pyridinyl)thieno[2,3-b]2-pyridinyl](2,3,4,5-tetrahydro-1H-benzo[b]azepin-1-yl)methanone, N-allyl-3-amino-N-(2,4-difluorophenyl)-6-(3-pyridinyl)thieno[2,3-b]pyridine-2-carboxamide, N-allyl-3-amino-N-(2,3-difluorophenyl)-6-(3-pyridinyl)thieno[2,3-b]pyridine-2-carboxamide, N-allyl-3-amino-N-(2,5-difluorophenyl)-6-(3-pyridinyl)thieno[2,3-b]pyridine-2-carboxamide, N-allyl-3-amino-N-(5-fluoro-2-methylphenyl)-6-(3-pyridinyl)thieno[2,3-b]pyridine-2-carboxamide, N-allyl-3-amino-N-(3,4-difluorophenyl)-6-(4-pyridinyl)thieno[2,3-b]pyridine-2-carboxamide, N-allyl-3-amino-N-(3,5-difluorophenyl)-6-(3-pyridinyl)thieno[2,3-b]pyridine-2-carboxamide, N-allyl-3-amino-N-(3-(pentafluoro-$\lambda^6$-sulfanyl)phenyl)-6-(3-pyridinyl)thieno[2,3-b]pyridine-2-carboxamide, N-allyl-3-amino-N-(3,5-difluorophenyl)-6-(4-pyridinyl)thieno[2,3-b]pyridine-2-carboxamide, N-allyl-3-amino-N-(3-(pentafluoro-$\lambda^6$-sulfanyl)phenyl)-6-(4-pyridinyl)thieno[2,3-b]pyridine-2-carboxamide, 3-amino-N-(1-naphthyl)-N-phenyl-6-(3-pyridinyl)thieno[2,3-b]pyridine-2-carboxamide, 3-amino-N-(2,6-dimethylphenyl)-6-(3-pyridinyl)thieno[2,3-b]pyridine-2-carboxamide, 3-amino-N-[4-(benzyloxy)phenyl]-6-(3-pyridinyl)thieno[2,3-b]pyridine-2-carboxamide, 3-amino-N-(4-iodophenyl)-6-(3-pyridinyl)thieno[2,3-b]pyridine-2-carboxamide, 3-amino-N-(2-iodo-4-pyridinyl)-6-(3-pyridinyl)thieno[2,3-b]pyridine-2-carboxamide, 3-amino-6-(3-pyridinyl)-N-(4-(trifluoromethyl)phenyl)thieno[2,3-b]pyridine-2-carboxamide, 3-amino-N-(3',5'-bis(trifluoromethyl)-[1,1'-biphenyl]-4-yl)-6-(3-pyridinyl)thieno[2,3-b]pyridine-2-carboxamide, 3-amino-N-(4-pyridinyl)-6-(4-pyridinyl)thieno[2,3-b]pyridine-2-carboxamide, 3-amino-N-(4-pyridinyl)-6-(5-pyrimidinyl)thieno[2,3-b]pyridine-2-carboxamide, 3-amino-N-(4-fluorophenyl)-N-(2-methylprop-2-en-1-yl)-6-(3-pyridinyl)thieno[2,3-b]pyridine-2-carboxamide, 3-amino-N-(4-fluorophenyl)-N-(prop-2-yn-1-yl)-6-(3-pyridinyl)thieno[2,3-b]pyridine-2-carboxamide, 3-amino-N-phenyl-N—((Z)-4-(prop-2-yloxy)but-2-enyl)-6-(3-pyridinyl)thieno[2,3-b]pyridine-2-carboxamide, 3-amino-N-benzyl-N-phenyl-6-(3-pyridinyl)thieno[2,3-b]pyridine-2-carboxamide, 3-amino-N-((E)-4-(pent-4-ynyloxy)but-2-enyl)-N-phenyl-6-(3-pyridinyl)thieno[2,3-b]pyridine-2-carboxamide, 3-amino-N-prenyl-N-(4-pyridinyl)-6-(3-pyridinyl)thieno[2,3-b]pyridine-2-carboxamide, 3-amino-N-(2-cyclopentylideneethyl)-N-phenyl-6-(3-pyridinyl)thieno[2,3-b]pyridine-2-carboxamide, 3-amino-6-(3-pyridinyl)thieno[2,3-b]2-pyridinyl)(3,4-dihydro-4,4-dimethyl-1(2H)-quinolinyl)methanone, 3-amino-N-(4-tert-butylphenyl)-N-(3-methylbut-2-en-1-yl)-6-(4-pyridinyl)thieno[2,3-b]pyridine-2-carboxamide, 3-amino-6-(4-pyridinyl)thieno[2,3-b]2-pyridinyl)(3,4-dihydro-4,4-dimethyl-1(2H)-quinolyl)methanone, 3-amino-N-(3-methoxyphenyl)-N-prenyl-6-(4-pyridinyl)thieno[2,3-b]pyridine-2-carboxamide, 3-amino-N-(4-methoxyphenyl)-N-prenyl-6-(4-pyridinyl)thieno[2,3-b]pyridine-2-carboxamide, and 3-amino-N-metallyl-N-phenyl-6-(4-pyridinyl)thieno[2,3-b]pyridine-2-carboxamide.

16. A compound represented by the following formula (1b) or a salt thereof, or a solvate or hydrate thereof:

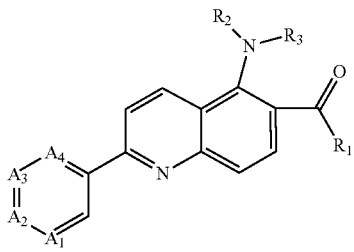

(1b)

wherein $A_1$ to $A_4$ each independently represent a carbon atom or a nitrogen atom, and at least one of $A_1$ to $A_4$ is a nitrogen atom; $R_1$ represents any one of a substituent represented by the following formula (2):

(2)

wherein $R_4$ represents an unsubstituted phenyl group, a 4-fluorophenyl group, a 2,3,4-trifluorophenyl group, a 4-iodophenyl group, a 2,4-difluorophenyl group, a 2,3-difluorophenyl group, a 2,5-difluorophenyl group, a 3,5-difluorophenyl group, a 3,4-difluorophenyl group, a 5-fluoro-2-methylphenyl group, a 3-pentafluorosulfanylphenyl group, a 2,6-dimethylphenyl group, a 4-benzyloxyphenyl group, a 3,5-bis(trifluoromethyl)biphenyl group, a 4-tert-butylphenyl group, a 3-methoxyphenyl group, or a 4-methoxyphenyl group; and $R_5$ represents a hydrogen atom, a lower alkyl group, a lower alkenyl group, or a lower alkynyl group; $R_2$ represents a hydrogen atom, a lower alkyl group, a lower acyl group, or an unsubstituted or optionally substituted aromatic lower alkyl group; and $R_3$ represents a hydrogen atom, or $R_2$ and $R_3$ may bind to each other to form a ring.

17. A medicament or a pharmaceutical composition comprising:
as an active ingredient, the compound according to claim 1 or a salt thereof, or a solvate or hydrate thereof, and a pharmaceutically acceptable carrier.

18. A method of treating ALS, comprising:
administering a therapeutically effective amount of the medicament or a pharmaceutical composition comprising as an active ingredient, a compound represented by the following formula (1) or a salt thereof, or a solvate or hydrate thereof, to a subject in need of treatment of ALS:

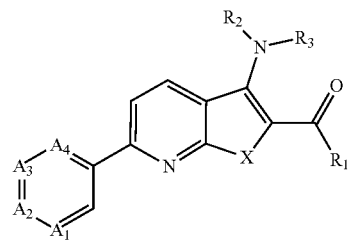

(1)

wherein X represents a sulfur atom or —CH=CH—; $A_1$ to $A_4$ each independently represent a carbon atom or a nitrogen atom, and at least one of $A_1$ to $A_4$ is a nitrogen atom; $R_1$ represents any one of a 1,2,3,4-tetrahydroquinolyl group (or a 3,4-dihydro-1(2H)-quinolyl group), a 3,4-dihydro-4,4-dimethyl-1(2H)-quinolyl group, a 2,3,4,5-tetrahydro-1H-1-benzazepinyl group, or a substituent represented by the following formula (2):

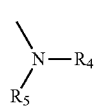

(2)

wherein R4 represents an unsubstituted phenyl group, a 4-fluorophenyl group, a 2,3,4-trifluorophenyl group, a 4-iodophenyl group, a 2,4-difluorophenyl group, a 2,3-difluorophenyl group, a 3,5-difluorophenyl group, a 3,4-difluorophenyl group, a 5-fluoro-2-methylphenyl group, a 3-pentafluorosulfanylphenyl group, a 2,6-dimethylphenyl group, a 4-benzyloxyphenyl group, a 3,5-bis(trifluoromethyl)biphenyl group, a 3-trifluoromethylphenyl group, a 4-trifluoromethylphenyl group, a 4-tert-butylphenyl group, a 3-methoxyphenyl group, and a 4-methoxyphenyl group, an unsubstituted or substituted pyridyl group, or an unsubstituted or substituted naphthyl group; R5 represents a hydrogen atom, a lower alkyl group, a lower alkenyl group, a lower alkynyl group optionally containing an oxygen atom and/or a double bond, or an unsubstituted or substituted aromatic lower alkyl group; R2 represents a hydrogen atom, a lower alkyl group, a lower acyl group, or an unsubstituted or substituted aromatic lower alkyl group; and R3 represents a hydrogen atom, or R2 and R3 may bind to each other to form a ring.

* * * * *